US005955329A

United States Patent [19]
Yuan et al.

[11] Patent Number: 5,955,329
[45] Date of Patent: Sep. 21, 1999

[54] ENGINEERING PLANT THIOESTERASES FOR ALTERED SUBSTRATE SPECIFICITY

[75] Inventors: Ling Yuan, Davis; Katayoon Dehesh, Vacaville; Jean Kridl, Davis; Vic Knauf, Winters, all of Calif.

[73] Assignee: Calgene, Inc., Davis, Calif.

[21] Appl. No.: 08/440,845

[22] Filed: May 15, 1995

[51] Int. Cl.⁶ .......................... C12N 15/00; C07H 21/04
[52] U.S. Cl. ..................... 435/172.1; 435/172.3; 435/196; 435/69.1; 435/320.1; 435/252.3; 435/252.33; 435/410; 536/23.1; 536/23.2; 536/23.6
[58] Field of Search .................. 435/69.1, 172.3, 435/196, 240.4, 172.1, 252.3, 252.33, 320.1, 410; 536/23.2, 23.6, 23.1

[56] References Cited

U.S. PATENT DOCUMENTS

| | | | |
|---|---|---|---|
| 5,344,771 | 9/1994 | Davies et al. | 435/172.2 |
| 5,455,167 | 10/1995 | Voelker et al. | 435/320.1 |
| 5,512,482 | 4/1996 | Voelker et al. | 435/320.1 |

FOREIGN PATENT DOCUMENTS

| | | |
|---|---|---|
| WO 92/11373 | 7/1992 | WIPO . |
| WO 92/20236 | 11/1992 | WIPO . |
| WO 94/10288 | 5/1994 | WIPO . |
| WO 95/06740 | 3/1995 | WIPO . |

OTHER PUBLICATIONS

Jenks, W. P. "Catalysis in Chemistry and Enzymology" Dover Edition, Dover Publication, New York, pp. 615–623, 1987.
Armstrong, R. N. "Structure–Function Relationship in enzymic catalysis. Can chimeric enzymes contribute?" Chem. Rev. 90, 1309–1325, 1990.
Dormann et al. (B) "Cloning and expression in *Escherichia coli* of a novel thioesterase from *Arabidopsis thaliana* . . . " Arch. Biochem. Biophys. 316(1), 612–618, Jan. 10, 1995.
Dormann et al. (A) "Cloning and expression in *Escherichia coli* of cDNA coding for the oleoyl–acyl carrier protein . . . " Biochemica et Biophysica Acta 1212, 134–136, 1994.
Knutzon et al. "Isolation and characterization of two safflower oleoyl–acyl carrier protein thioesterase cDNA clones" Plant Physiol. 100, 1751–1758, 1992.
Loader et al. "Isolation and characterization of two *Brassica napus* embryo acy–ACP thioesterase cDNA clones" Plant Mol. Biol. 23, 769–778, Nov. 1993.
Voelker et al. "Fatty acid biosynthesis redirected to medium chains in transgenic oilseed plants" Science 257, 72–74, Jul. 3, 1992.

Yuan, et al., "The catalytic cysteine and histidine in the plant acyl–acyl carrier protein thioesterases" *Journal of Biological Chemistry 271* vol. 7:3417–3419 (1996).
Yuan, et al., "Modification of the substrate specificity of an acyl–acyl carrier protein thioesterase by protein engineering", *Proceedings of the National Academy of Sciences of the United States of America 92* vol. 23:10639–10643 (1995).
Topfer, R, et al., "Modification of plant lipid synthesis", *Science* vol. 268:681–686 (1995).
Tai, M–H et al., "Roles of Ser–101 ASP–236 and HIS–237 in Catalysis of Thioesterase II and of the C–terminal region of the Enzyme in its interaction with Fatty Acid Synthase". *Proceeds of the National Academy of Science USA 90* vol. 5:1852–1856 (1993).
Kim, et al., "Chimeric restriction endonuclease" *Proc. Natl. Acad. Sci. USA Vo. 91*, pp. 883–887, Feb. 1994.
Hjelmstad, et al., "Chimeric Enzymes" *The Journal of Biological Chemistry*, vol. 269, No. 33, pp. 20995–21002 (1994).
Jones, et al., "Palmitoyl–Acyl Carrier Protein (ACP) Thioesterase and the Evolutionary Origin of Plant Acyl–ACP Thioesterases" *The Plant Cell*, vol. 7, pp. 359–371, Mar. 1995.
Lawson, et al., "Structure of a Myristoyl–ACP–Specific Thioesterase from *Vibrio harveyi*", Biochemistry, 1994, 33 9382–9388.

*Primary Examiner*—Robert A. Wax
*Assistant Examiner*—Nashaat T. Nashed

[57] ABSTRACT

Methods of altering substrate specificity of plant acyl-ACP thioesterases, and engineered plant acyl-ACP thioesterases so produced are provided. The C-terminal two thirds portion of plant thioesterases is identified as desirable for such modifications. DNA sequences and constructs for expression of engineered thioesterases, as well as the novel thioesterases produced therefrom are also provided. Such DNA sequences may be used for expression of the engineered thioesterases in host cells, particularly seed cells of oilseed crop plants, for the modification of fatty acid composition. A C12 preferring plant acyl-ACP thioesterase described herein may be altered to obtain a plant thioesterase having approximately equal activity on C14 and C12 substrates. Further modification of the C12 enzyme yields a thioesterase having greater activity on C14 as compared to C12 substrates. Also provided in the instant invention are novel plant acyl-ACP thioesterase sequences from *Cuphea palustris* and mangosteen (*Garcinia mangifera*), which demonstrate desirable thioesterase activity profiles for plant genetic engineering applications.

24 Claims, 30 Drawing Sheets

FIGURE 1C

```
T CTA GAG TGG AAG CCG AAT CCA CCC CAG TTG CTT GAT GAC CAT          49
  Leu Glu Trp Lys Pro Asn Pro Pro Gln Leu Leu Asp Asp His
  1               5                   10                  15

TTT GGG CCG CAT GGG TTA GTT TTC AGG CGC ACC TTT GCC ATC AGA TCG    97
Phe Gly Pro His Gly Leu Val Phe Arg Arg Thr Phe Ala Ile Arg Ser
        20                  25                  30

TAT GAG GTG GGA CCT GAC CGC TCC ACA TCT ATA GTG GCT GTT ATG AAT   145
Tyr Glu Val Gly Pro Asp Arg Ser Thr Ser Ile Val Ala Val Met Asn
            35                  40                  45

CAC TTG CAG GAG GCT GCA CTT AAT CAT GCG AAG AGT GTG GGA ATT CTA   193
His Leu Gln Glu Ala Ala Leu Asn His Ala Lys Ser Val Gly Ile Leu
                50                  55                  60

GGA GAT GGA TTC GGT ACG ACG CTA GAG ATG AGT AAG AGA GAT CTG ATA   241
Gly Asp Gly Phe Gly Thr Thr Leu Glu Met Ser Lys Arg Asp Leu Ile
65                  70                  75                  80

TGG GTT GTG AAA CGC ACG CAT GTT GCT GTG GAA CGG TAC CCT GCT TGG   289
Trp Val Val Lys Arg Thr His Val Ala Val Glu Arg Tyr Pro Ala Trp
                85                  90                  95

GGT GAT ACT GTT GAA GTA GAG TGC TGG GTT GGT GCA TCG GGA AAT AAT   337
Gly Asp Thr Val Glu Val Glu Cys Trp Val Gly Ala Ser Gly Asn Asn
                100                 105                 110
```

FIGURE 3A

```
GGC AGG CGC CAT GAT TTC GTC CGG GAC TGC AAA ACA GGC GAA ATT     385
Gly Arg Arg His Asp Phe Val Arg Asp Cys Lys Thr Gly Glu Ile
115                 120                 125

CTT ACA AGA TGT ACC AGT CTT TCG GTG ATG ATG AAT ACA AGG ACA AGG 433
Leu Thr Arg Cys Thr Ser Leu Ser Val Met Met Asn Thr Arg Thr Arg
        130                 135                 140

AGG TTG TCC AAA ATC CCT GAA GAA GTT AGA GGG GAG ATA GGG CCT GCA 481
Arg Leu Ser Lys Ile Pro Glu Glu Val Arg Gly Glu Ile Gly Pro Ala
145                 150                 155                 160

TTC ATT GAT AAT GTG GCT GTC AAA GAC GAG GAA ATT AAG AAA CCA CAG 529
Phe Ile Asp Asn Val Ala Val Lys Asp Glu Glu Ile Lys Lys Pro Gln
                165                 170                 175

AAG CTC AAT GAC AGC ACT GCA GAT TAC ATC CAA GGA GGA TTG ACT CCT 577
Lys Leu Asn Asp Ser Thr Ala Asp Tyr Ile Gln Gly Gly Leu Thr Pro
            180                 185                 190

CGA TGG AAT GAT TTG GAT ATC AAT CAG CAC GTT AAC ATC AAA TAC     625
Arg Trp Asn Asp Leu Asp Ile Asn Gln His Val Asn Ile Lys Tyr
        195                 200                 205

GTT GAC TGG ATT CTT GAG ACT GTC CCA GAC TCA ATC TTT GAG AGT CAT 673
Val Asp Trp Ile Leu Glu Thr Val Pro Asp Ser Ile Phe Glu Ser His
210                 215                 220
```

FIGURE 3B

```
CAT ATT TCC AGC TTC ACT ATT GAA TAC AGG AGA GAG TGC ACG AGG GAT    721
His Ile Ser Ser Phe Thr Ile Glu Tyr Arg Arg Glu Cys Thr Arg Asp
225                 230                 235                 240

AGC GTG CTG CAG TCC CTG ACC ACT GTC TCC GGT GGC TCG TCG GAA GCT    769
Ser Val Leu Gln Ser Leu Thr Thr Val Ser Gly Gly Ser Ser Glu Ala
        245                 250                 255

GGG TTA GTG TGC GAG CAC TTG CTC CAG CTT GAA GGT GGG TCT GAG GTA    817
Gly Leu Val Cys Glu His Leu Leu Gln Leu Glu Gly Gly Ser Glu Val
            260                 265                 270

TTG AGG GCA AAA ACA GAG TGG AGG CCT AAG CTT ACC GAT AGT TTC AGA    865
Leu Arg Ala Lys Thr Glu Trp Arg Pro Lys Leu Thr Asp Ser Phe Arg
                275                 280                 285

GGG ATT AGT GTG ATA CCC GCA GAA TCG AGT GTC TAACTAACGA AAGAAGCATC   918
Gly Ile Ser Val Ile Pro Ala Glu Ser Ser Val
                    290                 295

TGATGAAGTT TCTCCTGTGC TGTTGTTCGT GAGGATGCTT TTTAGAAGCT GCAGTTTGCA   978

TTGCTTGTGC AGAATCATGG CCTGTGGTTT TAGATATATA TTCAAAATTG TCCTATAGTC  1038

AAGAAACTTA ATATCAGAAA AATAACTCAA TGAGTCAAGG TTATCGAAGT AGTCATGTAA  1098

GCTTTGAAAT ATGTTGTGTA TTCCTCGGCT TTATGTAATC TGTAAGCTCT TTCTCTTGC   1157
```

FIGURE 3C

```
CCAAG ATG TTG AAG CTC TCT TCT TCC CGA AGC CCA TTG GCC CGC ATT CCC    50
      Met Leu Lys Leu Ser Ser Ser Arg Ser Pro Leu Ala Arg Ile Pro
                    5                  10                  15

ACC CGG CCC AGG CCC AAC TCC ATT CCT CCC CGG ATA ATT GTG GTT TCC      98
Thr Arg Pro Arg Pro Asn Ser Ile Pro Pro Arg Ile Ile Val Val Ser
                20                  25                  30

TCC TCA TCC AGC AAG GTT AAT CCA CTC AAA ACA GAG GCG GTG GTT TCT     146
Ser Ser Ser Ser Lys Val Asn Pro Leu Lys Thr Glu Ala Val Val Ser
            35                  40                  45

TCG GGG CTG GCT GAC CGG CTC CGG CTG GGC AGC TTG ACC GAG GAC GGG     194
Ser Gly Leu Ala Asp Arg Leu Arg Leu Gly Ser Leu Thr Glu Asp Gly
        50                  55                  60

CTT TCG TAT AAG GAG AAG TTC ATA GTG AGA TGC TAT GAG GTT GGG ATT     242
Leu Ser Tyr Lys Glu Lys Phe Ile Val Arg Cys Tyr Glu Val Gly Ile
    65                  70                  75

AAC AAG ACC GCT ACT GTT GAG ACT ATT GCC AAC CTC TTG CAG GAG GTT     290
Asn Lys Thr Ala Thr Val Glu Thr Ile Ala Asn Leu Leu Gln Glu Val
80                  85                  90                  95
```

FIGURE 4A

```
GGA TGC AAT CAC GCC CAA AGC GTT GGA TAT TCG ACG GGT GGG TTT TCG       338
Gly Cys Asn His Ala Gln Ser Val Gly Tyr Ser Thr Gly Gly Phe Ser
                100                 105                 110

ACA ACC CCT ACC ATG AGA AAA TTG CGT ATA TGG GTT ACT GCT CGC           386
Thr Thr Pro Thr Met Arg Lys Leu Arg Ile Trp Val Thr Ala Arg
         115                 120                 125

ATG CAC ATC GAA ATC TAC AAA TAT TAT CCA GCT TGG AGT GAT GTG GTG GAA   434
Met His Ile Glu Ile Tyr Lys Tyr Tyr Pro Ala Trp Ser Asp Val Val Glu
     130                 135                 140

ATA GAG TCG TGG GGC CAG GGT GAA GGA AAA ATC GGA ACC AGA CGT GAT       482
Ile Glu Ser Trp Gly Gln Gly Glu Gly Lys Ile Gly Thr Arg Arg Asp
     145                 150                 155

TGG ATT CTG AGA GAC TAT GCC ACT GGT CAA GTT ATT GGC CGA GCT ACT       530
Trp Ile Leu Arg Asp Tyr Ala Thr Gly Gln Val Ile Gly Arg Ala Thr
     160                 165                 170             175

AGC AAG TGG GTA ATG ATG AAC CAA GAC ACC AGG CGA CTT CAA AAA GTC       578
Ser Lys Trp Val Met Met Asn Gln Asp Thr Arg Arg Leu Gln Lys Val
         180                 185                 190

GAT GTT GAT CGT GAT GAG TAC TTG GTT CAC TGT CCA AGA GAA CTC           626
Asp Val Asp Arg Asp Glu Tyr Leu Val His Cys Pro Arg Glu Leu
         195                 200                 205
```

FIGURE 4B

```
AGA TTG GCA TTT CCA GAG GAA AAT AGC AGC TTG AAG AAA ATT TCA                        674
Arg Leu Ala Phe Pro Glu Glu Asn Ser Ser Leu Lys Lys Ile Ser
210                             215                 220

AAA CTT GAA GAT CCT TCT CAA TAT TCG AAG CTG GGG CTT GTG CCT AGA                    722
Lys Leu Glu Asp Pro Ser Gln Tyr Ser Lys Leu Gly Leu Val Pro Arg
225                 230                 235

AGA GCA GAT CTG GAC ATG AAT CAA CAT GTT AAT AAT GTC ACC TAT ATT                    770
Arg Ala Asp Leu Asp Met Asn Gln His Val Asn Asn Val Thr Tyr Ile
240                 245                 250                 255

GGA TGG GTG TTG GAG AGC ATG CCT CAA GAA ATC ATT GAT ACC CAT GAA                    818
Gly Trp Val Leu Glu Ser Met Pro Gln Glu Ile Ile Asp Thr His Glu
                260                 265                 270

CTG CAA ACC ATA ACA TTA GAC TAC AGA CGG GAA TGC CAA CAT GAT GAT                    866
Leu Gln Thr Ile Thr Leu Asp Tyr Arg Arg Glu Cys Gln His Asp Asp
275                 280                 285

GTG GTT GAT TCC ACT AGT TTG ACT CCA GAG CCT TCT GAA GAT GCT GAA GCA                914
Val Val Asp Ser Leu Thr Ser Pro Glu Pro Ser Glu Asp Ala Glu Ala
290                 295                 300

GTT TTC AAC CAT AAT GGA ACA AAT GGG TCT GCA AAT GTG AGC GCC AAC                    962
Val Phe Asn His Asn Gly Thr Asn Gly Ser Ala Asn Val Ser Ala Asn
305                 310                 315
```

FIGURE 4C

```
GAC CAT GGA TGC CGC AAC TTT CTG CAT CTA AGA TTG TCG GGC AAT    1010
Asp His Gly Cys Arg Asn Phe Leu His Leu Arg Leu Ser Gly Asn
320                     325                     330       335

GGA CTT GAA ATC AAC CGT GGT CGT ACT GAG AGA AAG AAA CCT ACA    1058
Gly Leu Glu Ile Asn Arg Gly Arg Thr Glu Arg Lys Lys Pro Thr
        340                     345                     350

AGA TGAGGCAATA AAGTACATTA TGTACTTTAT CGTTGCTTTA GCCGGCTTCT     1111
Arg

GGATGGTGAT TTCTTTCTGC ATTCCTTCTT TCCTTTTTGT TTTCCTAGGG TATCCTTCGC    1171

TTCTTGCCTG TAAGAGTATT ATGTTTTCCG TTTGCCCTGA AGTTGTAAAT TTGTCGAGGA    1231

ACTCGAGTCA TTGTTTGAAT CGAGGATGGT GAGAAGTGTA CTTGTTTGTT GTATTCCATT    1291

CTTCCTGAT                                                            1300
```

FIGURE 4D

```
CACTCAAGAA AAAGGGCACC AATTGAACGC TACAACGGAG TAACCAAAG ATG TTT AAG    58
                                                     Met Phe Lys

ATC TCC TCT TCC CTG AGC CCA GTG GAC CAA ATC CCC CCC ATT TCC CCA    106
Ile Ser Ser Ser Leu Ser Pro Val Asp Gln Ile Pro Pro Ile Ser Pro
  5                          10                         15

CTG CCC AGG CCC AGG CCC ATT ACC CCC AGG CCC CGT GTT TTG GCC GTC    154
Leu Pro Arg Pro Arg Pro Ile Thr Pro Arg Pro Arg Val Leu Ala Val
 20                          25                         30                    35

TCT TCT TCC TCT GGA AAG ATC GTT AAT AAT CCC CTT AAA GCG GAG ACT    202
Ser Ser Ser Ser Gly Lys Ile Val Asn Asn Pro Leu Lys Ala Glu Thr
             40                          45                         50

ACG GAG GCG GTT TCC GGG GAG TTA GCG CGC CGT TTC CGG CTT GGG AGG    250
Thr Glu Ala Val Ser Gly Glu Leu Ala Arg Arg Phe Arg Leu Gly Arg
         55                          60                         65

TTG GCT GAG GAC GGG TTT TCG TAT AAG GAG AAG TTT ATA GTG AGG TGT    298
Leu Ala Glu Asp Gly Phe Ser Tyr Lys Glu Lys Phe Ile Val Arg Cys
     70                          75                         80

TAT GAG GTT GGA ATT AAC AAG ACC GCC ACT GTT GAG ACT CTT GCC AAT    346
Tyr Glu Val Gly Ile Asn Lys Thr Ala Thr Val Glu Thr Leu Ala Asn
 85                          90                         95
```

FIGURE 5A

```
CTC TTA CAG GAG GTT GGA GGC AAT CAC GCC CAA AGT GTT GGA TTT TCG   394
Leu Leu Gln Glu Val Gly Gly Asn His Ala Gln Ser Val Gly Phe Ser
100                 105                 110                 115

ACG GAT GGG TTT GCG ACA ACC CAT TCC ATG AGA AAG ATG CAT CTG ATA   442
Thr Asp Gly Phe Ala Thr Thr His Ser Met Arg Lys Met His Leu Ile
        120                 125                 130

TGG GTT ACA GCT CGC ATG CAC ATA GAA TAC AAA TAT CCA GCT TGG       490
Trp Val Thr Ala Arg Met His Ile Glu Tyr Lys Tyr Pro Ala Trp
135                 140                 145

AGT GAT GTG ATA GAA GTA GAG ACG TGG ATT GGG GCC GAA GGA AGA ATT   538
Ser Asp Val Ile Glu Val Glu Thr Trp Ile Gly Ala Glu Gly Arg Ile
        150                 155                 160

GGA ACT AGA CGT AAT TGG ATT ATT AAG GAC TGT GCC ACT GAT GAA GTT   586
Gly Thr Arg Arg Asn Trp Ile Ile Lys Asp Cys Ala Thr Asp Glu Val
165                 170                 175

ATT GGC CGA GCT ACT AGC AAG TGG GTT ATG ATG AAC CAA GAT ACC AGG   634
Ile Gly Arg Ala Thr Ser Lys Trp Val Met Met Asn Gln Asp Thr Arg
        180                 185                 190                 195

CGA CTT GAA AAG GTT TCA GAT GAT CGT GAG GAG CAC TTG GTT TTC       682
Arg Leu Glu Lys Val Ser Asp Asp Arg Glu Glu His Leu Val Phe
        200                 205                 210
```

FIGURE 5B

```
AGT CCG AGA GAG CCA AGA TTG CCA TTT CCG GAT GAA AAT AAT AGC AGC    730
Ser Pro Arg Glu Pro Arg Leu Pro Phe Pro Asp Glu Asn Asn Ser Ser
215                             220                          225

TTG AAG AAA ATT TCC AAA CTT GAC GAT CCT GCT CAA TAT TCC AAG CTA    778
Leu Lys Lys Ile Ser Lys Leu Asp Asp Pro Ala Gln Tyr Ser Lys Leu
230                             235                          240

AGT CTT GAG CCT AGA AGA GGA GAT CTG GAC ATG AAT CAG CAT GTT AAT    826
Ser Leu Glu Pro Arg Arg Gly Asp Leu Asp Met Asn Gln His Val Asn
245                             250                          255

AAC GTC ACC TAT ATT GGA TGG GTG TTG GAG AGC ATG CCT CAA GAA ATC    874
Asn Val Thr Tyr Ile Gly Trp Val Leu Glu Ser Met Pro Gln Glu Ile
260                             265             270          275

ATA GAC ACC CAT GAA CTA CAG ACA ATA ACA TTA GAC TAC CGA AGG GAA    922
Ile Asp Thr His Glu Leu Gln Thr Ile Thr Leu Asp Tyr Arg Arg Glu
                280                          285             290

TGC CAA CAT GAT GAC TTG GTT GAT TCC TTG ACT AGT CCG GAG CCT TCT    970
Cys Gln His Asp Asp Leu Val Asp Ser Leu Thr Ser Pro Glu Pro Ser
         295                          300                    305

GAG TTC TCA GAA ACA ACA AAT GGA TCG GCA AAT GTG AGC CCC AAC GAC    1018
Glu Phe Ser Glu Thr Thr Asn Gly Ser Ala Asn Val Ser Pro Asn Asp
310                             315                          320
```

FIGURE 5C

```
AAT CGA TGC CTC AAC TTT TTG CAT CTA CTG AGA CTG TCA AGT GAT GGG    1066
Asn Arg Cys Leu Asn Phe Leu His Leu Leu Arg Leu Ser Ser Asp Gly
325                     330                     335

AGT GAA ATC AAC CGT GGT CGT ACT GTG TGG AGA AAG AAA CCT GCA AAA    1114
Ser Glu Ile Asn Arg Gly Arg Thr Val Trp Arg Lys Lys Pro Ala Lys
340                     345                     350         355

TGAGGCAATA ATTTACACAC TACTTAATTG TTGCTTTTTC CAGCTTCGTG TGGGTGGTGG   1174

TTTTTTTTGT TGGTTCATTT TTATGGTTTT TGGTTGGCCA TCAATTACGT TGGTGAGAAT   1234

AGTGTTATGG ATTTGGTGTG AGATTCTTTT ACATCAAAGA AACGATGTGA GATTCTTTTA   1294

CATCAAATTT TTCATAAACG                                              1314
```

FIGURE 5D

```
CCACGCGTCC GTGAGTTTGC TGGATACCAT TTTCCCTGCG AAGAAAC ATG GTG GCT          56
                                                  Met Val Ala

GCT GCA GCA AGT TCT GCA TGC TTC CCT GTT CCA TCC CCA GGA GCC TCC         104
Ala Ala Ala Ser Ser Ala Cys Phe Pro Val Pro Ser Pro Gly Ala Ser
         5                   10                  15

CCT AAA CCT GGG AAG TTA GGC AAC TGG TCA TCG AGT TTG AGC CCT TCC         152
Pro Lys Pro Gly Lys Leu Gly Asn Trp Ser Ser Ser Leu Ser Pro Ser
 20                  25                  30                  35

TTG AAG CCC AAG TCA ATC CCC AAT GGC GGA TTT CAG GTT AAG GCA AAT         200
Leu Lys Pro Lys Ser Ile Pro Asn Gly Gly Phe Gln Val Lys Ala Asn
         40                  45                  50

GCC AGT GCG CAT CCT AAG GCT AAC GGT TCT GCA GTA ACT CTA AAG TCT         248
Ala Ser Ala His Pro Lys Ala Asn Gly Ser Ala Val Thr Leu Lys Ser
                 55                  60                  65

GGC AGC CTC AAC ACT CAG GAG GAC ACT TTG TCG TCC TCC CCT CCT CCC         296
Gly Ser Leu Asn Thr Gln Glu Asp Thr Leu Ser Ser Ser Pro Pro Pro
 70                  75                  80

CGG GCT TTT TTT AAC CAG TTG CCT GAT TGG AGT ATG CTT CTG ACT GCA         344
Arg Ala Phe Phe Asn Gln Leu Pro Asp Trp Ser Met Leu Leu Thr Ala
         85                  90                  95

ATC ACA ACC GTC TTC GTG GCA CCA GAG AAG CGG TGG ACT ATG TTT GAT         392
Ile Thr Thr Val Phe Val Ala Pro Glu Lys Arg Trp Thr Met Phe Asp
100                 105                 110                 115
```

FIGURE 6A

```
AGG AAA TCT AAG AGG CCT AAC ATG CTC ATG GAC TCG TTT GGG TTG GAG    440
Arg Lys Ser Lys Arg Pro Asn Met Leu Met Asp Ser Phe Gly Leu Glu
            120                 125                 130

AGA GTT CAG GTC GAT GGG CTC GTG TTC AGA CAG AGT TTT TCG ATT AGG    488
Arg Val Gln Val Asp Gly Leu Val Phe Arg Gln Ser Phe Ser Ile Arg
            135                 140                 145

TCT TAT GAA ATA TGC GCT GAT CGA ACA GCC TCT ATA GAG ACG GTG ATG    536
Ser Tyr Glu Ile Cys Ala Asp Arg Thr Ala Ser Ile Glu Thr Val Met
            150                 155                 160

AAC CAC GTC CAG GAA ACA TCA CTC AAT CAA TGT AAG AGT ATA GGT CTT    584
Asn His Val Gln Glu Thr Ser Leu Asn Gln Cys Lys Ser Ile Gly Leu
            165                 170                 175

CTC GAT GAC GGC TTT GGT CGT AGT CCT GAG ATG TGT AAA AGG GAC CTC    632
Leu Asp Asp Gly Phe Gly Arg Ser Pro Glu Met Cys Lys Arg Asp Leu
            180                 185                 190                 195

ATT TGG GTG GTT ACA AGA ATG AAG ATA ATG GTG AAT CGC TAT CCA ACT    680
Ile Trp Val Val Thr Arg Met Lys Ile Met Val Asn Arg Tyr Pro Thr
            200                 205                 210

TGG GGC GAT ACT ATC GAG GTC AGT ACC TGG CTC TCT CAA TCG GGG AAA    728
Trp Gly Asp Thr Ile Glu Val Ser Thr Trp Leu Ser Gln Ser Gly Lys
            215                 220                 225
```

FIGURE 6B

```
ATC GGT ATG GGT CGC GAT TGG CTA ATA AGT GAT TGC AAC ACA GGA GAA     776
Ile Gly Met Gly Arg Asp Trp Leu Ile Ser Asp Cys Asn Thr Gly Glu
230                         235                     240

ATT CTT GTA AGA GCA ACG AGT TAT GCC GTG TAT ATG ATG CAA AAG ACG     824
Ile Leu Val Arg Ala Thr Ser Tyr Ala Val Tyr Met Met Gln Lys Thr
245                         250                     255

AGA AGA TTC TCA AAA CTC CCA CAC GAG GTT CGC CAG GAA TTT GCG CCT     872
Arg Arg Phe Ser Lys Leu Pro His Glu Val Arg Gln Glu Phe Ala Pro
260                         265                     270        275

CAT TTT CTG GAC TCT CCT GCC ATT GAA GAC AAC GAC GGT AAA TTG         920
His Phe Leu Asp Ser Pro Ala Ile Glu Asp Asn Asp Gly Lys Leu
                280                         285                 290

CAG AAG TTT GAT GTG AAG ACT GGT GAT GTC TCC ATT CGC AAG GGT CTA ACT 968
Gln Lys Phe Asp Val Lys Thr Gly Asp Val Ser Ile Arg Lys Gly Leu Thr
            295                         300                 305

CCG GGG TGG TAT GAC TTG GAT GTC AAT CAG CAC GTA AGC AAC GTG AAG    1016
Pro Gly Trp Tyr Asp Leu Asp Val Asn Gln His Val Ser Asn Val Lys
310                         315                     320

TAC ATT GGG TGG ATT CTC GAG AGT ATG CCA ACA GAA GTT TTG GAG ACT    1064
Tyr Ile Gly Trp Ile Leu Glu Ser Met Pro Thr Glu Val Leu Glu Thr
325                         330                     335
```

FIGURE 6C

```
CAG GAG CTA TGT TCT CTC ACC CTT GAA TAT AGG CGG GAA TGC GGA AGG    1112
Gln Glu Leu Cys Ser Leu Thr Leu Glu Tyr Arg Arg Glu Cys Gly Arg
340                 345                 350                 355

GAC AGT GTG CTG GAG TCC GTG ACC TCT ATG GAT CCC TCA AAA GTT GGA    1160
Asp Ser Val Leu Glu Ser Val Thr Ser Met Asp Pro Ser Lys Val Gly
        360                 365                 370

GAC CGG TTT CAG TAC CGG CAC CTT CTG CGG CTT GAG GAT GGG GCT GAT    1208
Asp Arg Phe Gln Tyr Arg His Leu Leu Arg Leu Glu Asp Gly Ala Asp
    375                 380                 385

ATC ATG AAG GGA AGA ACT GAG TGG CGG CCG AAG AAT GCA GGA ACT AAC    1256
Ile Met Lys Gly Arg Arg Thr Glu Trp Arg Pro Lys Asn Ala Gly Thr Asn
390                 395                 400

GGG GCG ATA TCA ACA GGA AAG ACT TGAAATGGAA ACTCTGTCTC TTAGAATAAT    1310
Gly Ala Ile Ser Thr Gly Lys Thr
405                 410

CTCGGGATTC TTCCGGGATG TGCATTTCTT TTCTCTTTTT CATTTCCTGG TGAGCTGAAA    1370

GAAGAGCATG TGGTTGTGGT TGCAAGCAGT AAACTGTGTA GTTCGTTTGT TCGCTTTGCA    1430

TCGAAACCTT TGTATAATAA TATGATCTG                                    1459
```

FIGURE 6D

GAAGAGCCATG TGGTTGTGGT TGCAAGCAGT AAACTGTGTA GTTCGTTTGT TCGCTTTGCA 1430

TCGAAACCTT TGTATAATAA TATGATCTG 1459

FIGURE 6E

```
CCACGGGTCC GCTGAGTTTG CTGGTTACCA TTTTCCCTGC GAACAAAC ATG GTG GCT      57
                                                    Met Val Ala

GCC GCA GCA AGT GCT GCA TTC TTC TCC GTC GCA ACC CCG CGA ACA AAC     105
Ala Ala Ala Ser Ala Ala Phe Phe Ser Val Ala Thr Pro Arg Thr Asn
             5                  10                  15

ATT TCG CCA TCG AGC TTG AGC GTC CCC TTC AAG CCC AAA TCA AAC CAC     153
Ile Ser Pro Ser Ser Leu Ser Val Pro Phe Lys Pro Lys Ser Asn His
 20                  25                  30                  35

AAT GGT GGC TTT CAG GTT AAG GCA AAC GCC AGT GCC CAT CCT AAG GCT     201
Asn Gly Gly Phe Gln Val Lys Ala Asn Ala Ser Ala His Pro Lys Ala
         40                  45                  50

AAC GGT TCT GCA GTA AGT CTA AAG TCT GGC AGC CTC GAG ACT CAG GAG     249
Asn Gly Ser Ala Val Ser Leu Lys Ser Gly Ser Leu Glu Thr Gln Glu
     55                  60                  65

GAC AAA ACT TCA TCG TCG TCC CCT CCT CGG ACT TTC ATT AAC CAG         297
Asp Lys Thr Ser Ser Ser Ser Pro Pro Arg Thr Phe Ile Asn Gln Asn
 70                  75                  80

TTG CCC GTC TGG AGT ATG CTT CTG TCT GCA GTC ACG ACT GTC TTC GGG     345
Leu Pro Val Trp Ser Met Leu Leu Ser Ala Val Thr Thr Val Phe Gly
 85                  90                  95
```

FIGURE 7A

```
GTG GCT GAG AAG CAG TGG CCA ATG CTT GAC CGG AAA TCT AAG AGG CCC    393
Val Ala Glu Lys Gln Trp Pro Met Leu Asp Arg Lys Ser Lys Arg Pro
100             105                 110                 115

GAC ATG CTT GTG GAA CCG CTT GGG GTT GAC AGG ATT GTT TAT GAT GGG    441
Asp Met Leu Val Glu Pro Leu Gly Val Asp Arg Ile Val Tyr Asp Gly
            120                 125                 130

GTT AGT TTC AGA CAG AGT TTT TCG ATT AGA TCT TAC GAA ATA GGC GCT    489
Val Ser Phe Arg Gln Ser Phe Ser Ile Arg Ser Tyr Glu Ile Gly Ala
            135                 140                 145

GAT CGA ACA GCC TCG ATA GAG ACC CTG ATG AAC ATG TTC CAG GAA ACA    537
Asp Arg Thr Ala Ser Ile Glu Thr Leu Met Asn Met Phe Gln Glu Thr
        150                 155                 160

TCT CTT AAT CAT TGT AAG ATT ATC GGT CTT CTC AAT GAC GGC TTT GGT    585
Ser Leu Asn His Cys Lys Ile Ile Gly Leu Leu Asn Asp Gly Phe Gly
        165                 170                 175

CGA ACT CCT GAG ATG TGT AAG AGG GAC CTC ATT TGG GTG GTC ACG AAA    633
Arg Thr Pro Glu Met Cys Lys Arg Asp Leu Ile Trp Val Val Thr Lys
    180                 185                 190                 195

ATG CAG ATC GAG GTG AAT CGC TAT CCT ACT TGG GGT GAT ACT ATA GAG    681
Met Gln Ile Glu Val Asn Arg Tyr Pro Thr Trp Gly Asp Thr Ile Glu
                200                 205                 210
```

FIGURE 7B

```
GTC AAT ACT TGG GTC TCA GCG TCG GGG AAA CAC GGT ATG GGT CGA GAT    729
Val Asn Thr Trp Val Ser Ala Ser Gly Lys His Gly Met Gly Arg Asp
215                     220                 225

TGG CTG ATA AGT GAT TGC CAT ACA GGA GAA ATT CTT ATA AGA GCA ACG    777
Trp Leu Ile Ser Asp Cys His Thr Gly Glu Ile Leu Ile Arg Ala Thr
        230                 235                 240

AGC GTG TGG GCT ATG ATG AAT CAA AAG ACG AGA AGA TTG TCG AAA ATT    825
Ser Val Trp Ala Met Met Asn Gln Lys Thr Arg Arg Leu Ser Lys Ile
245                 250                 255

CCA TAT GAG GTT CGA CAG GAG ATA ATC GAG CCT CAG TTT GTG GAC TCT GCT    873
Pro Tyr Glu Val Arg Gln Glu Ile Ile Glu Pro Gln Phe Val Asp Ser Ala
260                 265                 270                 275

CCT GTC ATT GTA GAC GAT CGA AAA TTT CAC AAG CTT GAT TTG AAG ACC    921
Pro Val Ile Val Asp Asp Arg Lys Phe His Lys Leu Asp Leu Lys Thr
        280                 285                 290

GGT GAT TCC ATT TGC AAT GGT CTA ACT CCA AGG TGG ACT GAC TTG GAT    969
Gly Asp Ser Ile Cys Asn Gly Leu Thr Pro Arg Trp Thr Asp Leu Asp
            295                 300                 305

GTC AAT CAG CAC GTT AAC AAT GTG AAA TAC ATC GGG TGG ATT CTC CAG    1017
Val Asn Gln His Val Asn Asn Val Lys Tyr Ile Gly Trp Ile Leu Gln
310                 315                 320
```

FIGURE 7C

```
AGT GTT CCC ACA GAA GTT TTC GAG ACG CAG GAG CTA TGT GGC CTC ACC    1065
Ser Val Pro Thr Glu Val Phe Glu Thr Gln Glu Leu Cys Gly Leu Thr
325                 330                 335

CTT GAG TAT AGG CGA GAA CGA AGG GAC AGT GTG CTG GAG TCC GTG        1113
Leu Glu Tyr Arg Arg Glu Arg Arg Asp Ser Val Leu Glu Ser Val
340                 345                 350                 355

ACC GCT ATG GAT CCA TCA AAA GAG GGA GAC CGG TCT CTT TAC CAG CAC    1161
Thr Ala Met Asp Pro Ser Lys Glu Gly Asp Arg Ser Leu Tyr Gln His
        360                 365                 370

CTT CTC CGA CTC GAG GAC GGG GCT GAT ATC GTC AAG GGA AGA ACC GAG    1209
Leu Leu Arg Leu Glu Asp Gly Ala Asp Ile Val Lys Gly Arg Thr Glu
375                 380                 385

TGG CGG CCG AAG AAT GCA GGA GCC AAG GGA GCA ATA TTA ACC GGA AAG    1257
Trp Arg Pro Lys Asn Ala Gly Ala Lys Gly Ala Ile Leu Thr Gly Lys
390                 395                 400

ACC TCA AAT GGA AAC TCT ATA TCT TAGAAGGAGG AAGGGACCTT TCCGAGTGT    1311
Thr Ser Asn Gly Asn Ser Ile Ser
405                 410

GTGTTTATTT GCTTTGCTTT GATTCACTCC ATTGTATAAT AATACTACGG TCAGCCGTCT  1371

TTGTATTTGC TAAGACAAAT AGCACAGTCA TTAAGTT                           1408
```

FIGURE 7D

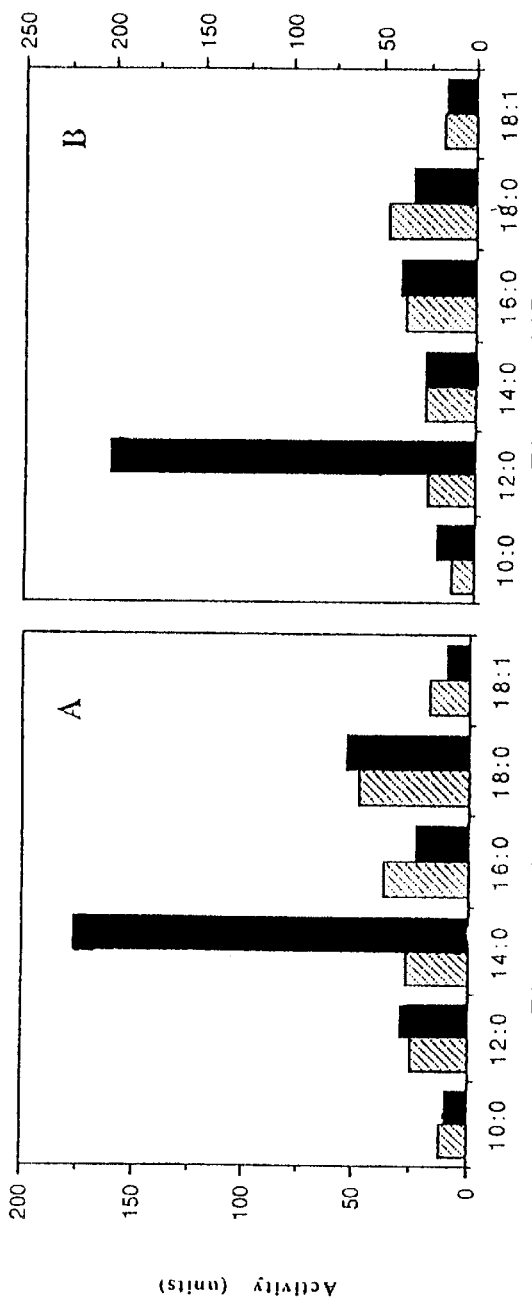
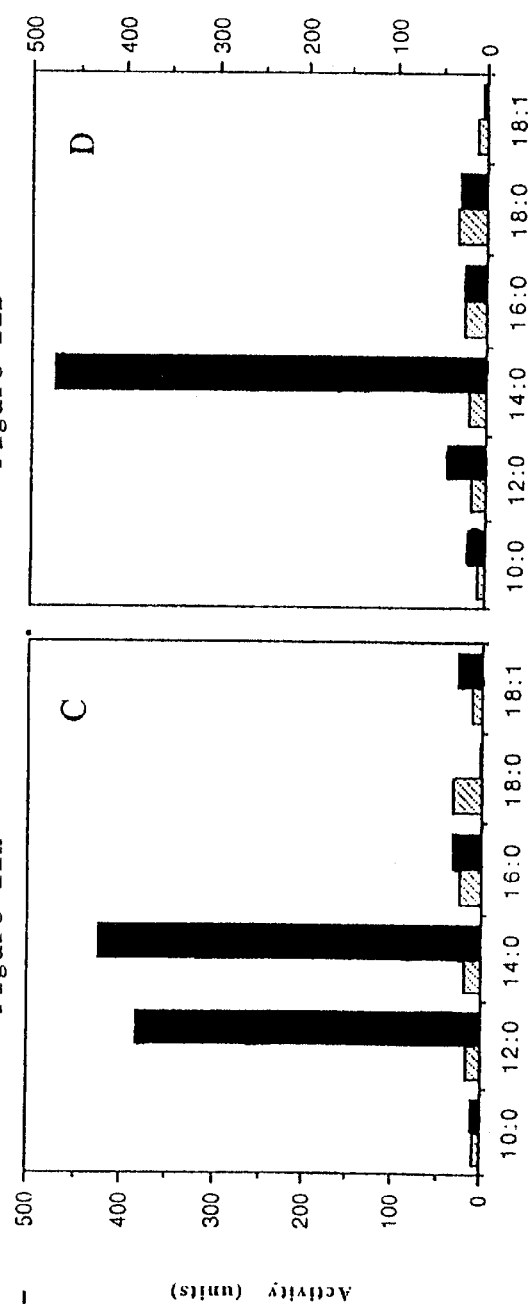
Figure 11A
Figure 11B
Figure 11C
Figure 11D

FIGURE 13

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 382 amino acids
      (B) TYPE: amino acid
      (D) TOPOLOGY: linear (ii) MOLECULE TYPE: protein (xi) SEQUENCE DESCRIPTION: SEQ ID NO: 1:

```
Met Ala Thr Thr Ser Leu Ala Ser Ala Phe Cys Ser Met Lys Ala Val
 1               5                  10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140
```

```
Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
    370                 375                 380
```

(2) INFORMATION FOR SEQ ID NO: 2:

(i) SEQUENCE CHARACTERISTICS:
        (A) LENGTH: 382 residues
        (B) TYPE: amino acid
        (D) TOPOLOGY: linear (ii) MOLECULE TYPE: protein (xi) SEQUENCE DESCRIPTION: SEQ ID NO: 2:

```
Met Ala Thr Thr Ser Leu Ala Ser Ala Phe Cys Ser Met Lys Ala
1                   5                   10                  15

Val Met Leu Ala Arg Asp Gly Arg Gly Met Lys Pro Arg Ser Ser
                20                  25                  30

Asp Leu Gln Leu Arg Ala Gly Asn Ala Gln Thr Ser Leu Lys Met
            35                  40                  45

Ile Asn Gly Thr Lys Phe Ser Tyr Thr Glu Ser Leu Lys Lys Leu
        50                  55                  60

Pro Asp Trp Ser Met Leu Phe Ala Val Ile Thr Thr Ile Phe Ser
    65                  70                  75

Ala Ala Glu Lys Gln Trp Thr Asn Leu Glu Trp Lys Pro Lys Pro
            80                  85                  90

Asn Pro Pro Gln Leu Leu Asp Asp His Phe Gly Pro His Gly Leu
        95                  100                 105

Val Phe Arg Arg Thr Phe Ala Ile Arg Ser Tyr Glu Val Gly Pro
    110                 115                 120
```

```
Asp Arg Ser Thr Ser Ile Val Ala Val Met Asn His Leu Gln Glu
            125                 130                 135

Ala Ala Leu Asn His Ala Lys Ser Val Gly Ile Leu Gly Asp Gly
            140                 145                 150

Phe Gly Thr Thr Leu Glu Met Ser Lys Arg Asp Leu Ile Trp Val
            155                 160                 165

Val Lys Arg Thr His Val Ala Val Glu Arg Tyr Pro Ala Trp Gly
            170                 175                 180

Ser Gly Asn Asn Gly Arg Arg His Asp Phe Leu Val Arg Asp Cys
            185                 190                 195

Asp Thr Val Glu Val Glu Cys Trp Val Gly Ala Lys Thr Gly Glu
            200                 205                 210

Ile Leu Thr Arg Cys Thr Ser Leu Ser Val Met Met Asn Thr Arg
            215                 220                 225

Thr Arg Arg Leu Ser Lys Ile Pro Glu Glu Val Arg Gly Glu Ile
            230                 235                 240

Gly Pro Ala Phe Ile Asp Asn Val Ala Val Lys Asp Glu Glu Ile
            245                 250                 255

Lys Lys Pro Gln Lys Leu Asn Asp Ser Thr Ala Asp Tyr Ile Gln
            260                 265                 270

Gly Gly Leu Thr Pro Arg Trp Asn Asp Leu Asp Ile Asn Gln His
            275                 280                 285

Val Asn Asn Ile Lys Tyr Val Asp Trp Ile Leu Glu Thr Val Pro
            290                 295                 300

Asp Ser Ile Phe Glu Ser His His Ile Ser Ser Phe Thr Ile Glu
            305                 310                 315

Tyr Arg Arg Glu Cys Thr Met Asp Ser Val Leu Gln Ser Leu Thr
            320                 325                 330

Thr Val Ser Gly Gly Ser Ser Glu Ala Gly Leu Val Cys Glu His
            335                 340                 345

Leu Leu Gln Leu Glu Gly Gly Ser Glu Val Leu Arg Ala Lys Thr
            350                 355                 360

Glu Trp Arg Pro Lys Leu Thr Asp Ser Phe Arg Gly Ile Ser Val
            365                 370                 375

Ile Pro Ala Glu Ser Ser Val
            380

(2) INFORMATION FOR SEQ ID NO: 3:

(i) SEQUENCE CHARACTERISTICS:
        (A) LENGTH: 411 residues
        (B) TYPE: amino acid
        (D) TOPOLOGY: linear (ii) MOLECULE TYPE: protein (xi) SEQUENCE DESCRIPTION: SEQ ID NO: 3:

Met Val Ala Ala Ala Ser Ser Ala Cys Phe Pro Val Pro Ser Pro
 1               5                  10                  15

Gly Ala Ser Pro Lys Pro Gly Lys Leu Gly Asn Trp Ser Ser Ser Leu
             20                  25                  30

Ser Pro Ser Leu Lys Pro Lys Ser Ile Pro Asn Gly Gly Phe Gln Val
             35                  40                  45

Lys Ala Asn Ala Ser Ala His Pro Lys Ala Asn Gly Ser Ala Val Thr
             50                  55                  60
```

```
Leu Lys Ser Gly Ser Leu Asn Thr Gln Glu Asp Thr Leu Ser Ser
 65                  70                  75                  80

Pro Pro Pro Arg Ala Phe Phe Asn Gln Leu Pro Asp Trp Ser Met Leu
                 85                  90                  95

Leu Thr Ala Ile Thr Thr Val Phe Val Ala Pro Glu Lys Arg Trp Thr
                100                 105                 110

Met Phe Asp Arg Lys Ser Lys Arg Pro Asn Met Leu Met Asp Ser Phe
                115                 120                 125

Gly Leu Glu Arg Val Val Gln Asp Gly Leu Val Phe Arg Gln Ser Phe
                130                 135                 140

Ser Ile Arg Ser Tyr Glu Ile Cys Ala Asp Arg Thr Ala Ser Ile Glu
145                 150                 155                 160

Thr Val Met Asn His Val Gln Glu Thr Ser Leu Asn Gln Cys Lys Ser
                165                 170                 175

Ile Gly Leu Leu Asp Asp Gly Phe Gly Arg Ser Pro Glu Met Cys Lys
                180                 185                 190

Arg Asp Leu Ile Trp Val Val Thr Arg Met Lys Ile Met Val Asn Arg
                195                 200                 205

Tyr Pro Thr Trp Gly Asp Thr Ile Glu Val Ser Thr Trp Leu Ser Gln
                210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Val Tyr Ala Met Met Asn
                245                 250                 255

Gln Lys Thr Arg Arg Phe Ser Lys Leu Pro His Glu Val Arg Gln Glu
                260                 265                 270

Phe Ala Pro His Phe Leu Asp Ser Pro Ala Ile Glu Asp Asn Asp
                275                 280                 285

Gly Lys Leu Gln Lys Phe Asp Val Lys Thr Gly Asp Ser Ile Arg Lys
                290                 295                 300

Gly Leu Thr Pro Gly Trp Tyr Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
                340                 345                 350

Cys Gly Arg Asp Ser Val Leu Glu Ser Val Thr Ser Met Asp Pro Ser
                355                 360                 365

Lys Val Gly Asp Arg Phe Gln Tyr Arg His Leu Leu Arg Leu Glu Asp
370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr
                405                 410
```

(2) INFORMATION FOR SEQ ID NO: 4:

(i) SEQUENCE CHARACTERISTICS:
        (A) LENGTH: 411 residues
        (B) TYPE: amino acid
        (D) TOPOLOGY: linear (ii) MOLECULE TYPE: protein (xi) SEQUENCE DESCRIPTION: SEQ ID NO: 4:

```
Met Val Ala Ala Ala Ser Ala Ala Phe Phe Ser Val Ala Thr Pro
 1                   5                  10                  15
```

Arg Thr Asn Ile Ser Pro Ser Ser Leu Ser Val Pro Phe Lys Pro Lys
                20                  25                  30

Ser Asn His Asn Gly Gly Phe Gln Val Lys Ala Asn Ala Ser Ala His
                35                  40                  45

Pro Lys Ala Asn Gly Ser Ala Val Ser Leu Lys Ser Gly Ser Leu Glu
    50                  55                  60

Thr Gln Glu Asp Lys Thr Ser Ser Ser Pro Pro Arg Thr Phe
65                  70                  75                  80

Ile Asn Gln Leu Pro Val Trp Ser Met Leu Leu Ser Ala Val Thr Thr
                    85                  90                  95

Val Phe Gly Val Ala Glu Lys Gln Trp Pro Met Leu Asp Arg Lys Ser
                100                 105                 110

Lys Arg Pro Asp Met Leu Val Glu Pro Leu Gly Val Asp Arg Ile Val
            115                 120                 125

Tyr Asp Gly Val Ser Phe Arg Gln Ser Phe Ser Ile Arg Ser Tyr Glu
    130                 135                 140

Ile Gly Ala Asp Arg Thr Ala Ser Ile Glu Thr Leu Met Asn Met Phe
145                 150                 155                 160

Gln Glu Thr Ser Leu Asn His Cys Lys Ile Ile Gly Leu Leu Asn Asp
                165                 170                 175

Gly Phe Gly Arg Thr Pro Glu Met Cys Lys Arg Asp Leu Ile Trp Val
                180                 185                 190

Val Thr Lys Met Gln Ile Glu Val Asn Arg Tyr Pro Thr Trp Gly Asp
            195                 200                 205

Thr Ile Glu Val Asn Thr Trp Val Ser Ala Ser Gly Lys His Gly Met
210                 215                 220

Gly Arg Asp Trp Leu Ile Ser Asp Cys His Thr Gly Glu Ile Leu Ile
225                 230                 235                 240

Arg Ala Thr Ser Val Trp Ala Met Met Asn Gln Lys Thr Arg Arg Leu
                245                 250                 255

Ser Lys Ile Pro Tyr Glu Val Arg Gln Glu Ile Glu Pro Gln Phe Val
                260                 265                 270

Asp Ser Ala Pro Val Ile Val Asp Asp Arg Lys Phe His Lys Leu Asp
            275                 280                 285

Leu Lys Thr Gly Asp Ser Ile Cys Asn Gly Leu Thr Pro Arg Trp Thr
    290                 295                 300

Asp Leu Asp Val Asn Gln His Val Asn Asn Val Lys Tyr Ile Gly Trp
305                 310                 315                 320

Ile Leu Gln Ser Val Pro Thr Glu Val Phe Glu Thr Gln Glu Leu Cys
                325                 330                 335

Gly Leu Thr Leu Glu Tyr Arg Arg Glu Cys Gly Arg Asp Ser Val Leu
                340                 345                 350

Glu Ser Val Thr Ala Met Asp Pro Ser Lys Glu Gly Asp Arg Ser Leu
            355                 360                 365

Tyr Gln His Leu Leu Arg Leu Glu Asp Gly Ala Asp Ile Val Lys Gly
    370                 375                 380

Arg Thr Glu Trp Arg Pro Lys Asn Ala Gly Ala Lys Gly Ala Ile Leu
385                 390                 395                 400

Thr Gly Lys Thr Ser Asn Gly Asn Ser Ile Ser
            405                 410

(2) INFORMATION FOR SEQ ID NO: 5:

(i) SEQUENCE CHARACTERISTICS:

(A) LENGTH: 352 residues
(B) TYPE: amino acid
(D) TOPOLOGY: linear (ii) MOLECULE TYPE: protein (xi) SEQUENCE DESCRIPTION: SEQ ID NO: 5:

```
Met Leu Lys Leu Ser Ser Arg Ser Pro Leu Ala Arg Ile Pro Thr
 1               5                  10                 15

Arg Pro Arg Pro Asn Ser Ile Pro Pro Arg Ile Ile Val Val Ser Ser
            20                  25                  30

Ser Ser Ser Lys Val Asn Pro Leu Lys Thr Glu Ala Val Val Ser Ser
        35                  40                  45

Gly Leu Ala Asp Arg Leu Arg Leu Gly Ser Leu Thr Glu Asp Gly Leu
 50                  55                  60

Ser Tyr Lys Glu Lys Phe Ile Val Arg Cys Tyr Glu Val Gly Ile Asn
 65                  70                  75                  80

Lys Thr Ala Thr Val Glu Thr Ile Ala Asn Leu Leu Gln Glu Val Gly
                 85                  90                  95

Cys Asn His Ala Gln Ser Val Gly Tyr Ser Thr Gly Gly Phe Ser Thr
             100                 105                 110

Thr Pro Thr Met Arg Lys Leu Arg Leu Ile Trp Val Thr Ala Arg Met
             115                 120                 125

His Ile Glu Ile Tyr Lys Tyr Pro Ala Trp Ser Asp Val Val Glu Ile
 130                 135                 140

Glu Ser Trp Gly Gln Gly Glu Gly Lys Ile Gly Thr Arg Arg Asp Trp
 145                 150                 155                 160

Ile Leu Arg Asp Tyr Ala Thr Gly Gln Val Ile Gly Arg Ala Thr Ser
                 165                 170                 175

Lys Trp Val Met Met Asn Gln Asp Thr Arg Arg Leu Gln Lys Val Asp
             180                 185                 190

Val Asp Val Arg Asp Glu Tyr Leu Val His Cys Pro Arg Glu Leu Arg
             195                 200                 205

Leu Ala Phe Pro Glu Glu Asn Asn Ser Ser Leu Lys Lys Ile Ser Lys
 210                 215                 220

Leu Glu Asp Pro Ser Gln Tyr Ser Lys Leu Gly Leu Val Pro Arg Arg
225                 230                 235                 240

Ala Asp Leu Asp Met Asn Gln His Val Asn Asn Val Thr Tyr Ile Gly
             245                 250                 255

Trp Val Leu Glu Ser Met Pro Gln Glu Ile Ile Asp Thr His Glu Leu
             260                 265                 270

Gln Thr Ile Thr Leu Asp Tyr Arg Arg Glu Cys Gln His Asp Asp Val
             275                 280                 285

Val Asp Ser Leu Thr Ser Pro Glu Pro Ser Glu Asp Ala Glu Ala Val
 290                 295                 300

Phe Asn His Asn Gly Thr Asn Gly Ser Ala Asn Val Ser Ala Asn Asp
305                 310                 315                 320

His Gly Cys Arg Asn Phe Leu His Leu Leu Arg Leu Ser Gly Asn Gly
             325                 330                 335

Leu Glu Ile Asn Arg Gly Arg Thr Glu Trp Arg Lys Lys Pro Thr Arg
             340                 345                 350
```

(2) INFORMATION FOR SEQ ID NO: 6:

(i) SEQUENCE CHARACTERISTICS:
(A) LENGTH: 362 residues
(B) TYPE: amino acid (D) TOPOLOGY: linear (ii) MOLECULE TYPE: protein (xi) SEQUENCE DESCRIPTION: SEQ ID NO: 6:

```
Met Leu Lys Leu Ser Cys Asn Ala Thr Asp Lys Leu Gln Thr Leu
1               5                  10                  15

Phe Ser His Ser His Gln Pro Asp Pro Ala His Arg Arg Thr Val
               20                  25                  30

Ser Ser Val Ser Cys Ser His Leu Arg Lys Pro Val Leu Asp Pro
               35                  40                  45

Leu Arg Ala Ile Val Ser Ala Asp Gln Gly Ser Val Ile Arg Ala
               50                  55                  60

Glu Gln Gly Leu Gly Ser Leu Ala Asp Gln Leu Arg Leu Gly Ser
               65                  70                  75

Leu Thr Glu Asp Gly Leu Ser Tyr Lys Glu Lys Phe Ile Val Arg
               80                  85                  90

Ser Tyr Glu Val Gly Ser Asn Lys Thr Ala Thr Val Glu Thr Val
               95                 100                 105

Ala Asn Leu Leu Gln Glu Val Gly Cys Asn His Ala Gln Ser Val
              110                 115                 120

Gly Phe Ser Thr Asp Gly Phe Ala Thr Thr Pro Thr Met Arg Lys
              125                 130                 135

Leu His Leu Ile Trp Val Thr Ala Arg Met His Ile Glu Ile Tyr
              140                 145                 150

Lys Tyr Pro Ala Trp Gly Asp Val Val Glu Ile Glu Thr Trp Cys
              155                 160                 165

Gln Ser Glu Gly Arg Ile Gly Thr Arg Arg Asp Trp Ile Leu Lys
              170                 175                 180

Asp Val Ala Thr Gly Glu Val Thr Gly Arg Ala Thr Ser Lys Trp
              185                 190                 195

Val Met Met Asn Gln Asp Thr Arg Arg Leu Gln Lys Val Ser Asp
              200                 205                 210

Asp Val Arg Asp Glu Tyr Leu Val Phe Cys Pro Lys Glu Leu Arg
              215                 220                 225

Leu Ala Phe Pro Glu Glu Asn Asn Arg Ser Leu Lys Lys Ile Pro
              230                 235                 240

Lys Leu Glu Asp Pro Ala Gln Tyr Ser Met Ile Gly Leu Lys Pro
              245                 250                 255

Arg Arg Ala Asp Leu Asp Met Asn Gln His Val Asn Asn Val Thr
              260                 265                 270

Tyr Ile Gly Trp Val Leu Glu Ser Ile Pro Gln Glu Ile Val Asp
              275                 280                 285

Thr His Glu Leu Gln Val Ile Thr Leu Asp Tyr Arg Arg Glu Cys
              290                 295                 300

Gln Gln Asp Asp Val Val Asp Ser Leu Thr Thr Thr Ser Glu
              305                 310                 315

Ile Gly Gly Thr Asn Gly Ser Ala Ser Ser Gly Thr Gln Gly Gln
              320                 325                 330

Asn Asp Ser Gln Phe Leu His Leu Leu Arg Leu Ser Gly Asp Gly
              335                 340                 345

Gln Glu Ile Asn Arg Gly Thr Thr Leu Trp Arg Lys Lys Pro Ser
              350                 355                 360

Asn Leu
362
```

(2) INFORMATION FOR SEQ ID NO: 7:

(i) SEQUENCE CHARACTERISTICS:
        (A) LENGTH: 1157 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO: 7:

```
T CTA GAG TGG AAG CCG AAG CCG AAT CCA CCC CAG TTG CTT GAT GAC CAT        49
  Leu Glu Trp Lys Pro Lys Pro Asn Pro Pro Gln Leu Leu Asp Asp His
  1               5                   10                  15

TTT GGG CCG CAT GGG TTA GTT TTC AGG CGC ACC TTT GCC ATC AGA TCG          97
Phe Gly Pro His Gly Leu Val Phe Arg Arg Thr Phe Ala Ile Arg Ser
                20                  25                  30

TAT GAG GTG GGA CCT GAC CGC TCC ACA TCT ATA GTG GCT GTT ATG AAT         145
Tyr Glu Val Gly Pro Asp Arg Ser Thr Ser Ile Val Ala Val Met Asn
            35                  40                  45

CAC TTG CAG GAG GCT GCA CTT AAT CAT GCG AAG AGT GTG GGA ATT CTA         193
His Leu Gln Glu Ala Ala Leu Asn His Ala Lys Ser Val Gly Ile Leu
    50                  55                  60

GGA GAT GGA TTC GGT ACG ACG CTA GAG ATG AGT AAG AGA GAT CTG ATA         241
Gly Asp Gly Phe Gly Thr Thr Leu Glu Met Ser Lys Arg Asp Leu Ile
65                  70                  75                  80

TGG GTT GTG AAA CGC ACG CAT GTT GCT GTG GAA CGG TAC CCT GCT TGG         289
Trp Val Val Lys Arg Thr His Val Ala Val Glu Arg Tyr Pro Ala Trp
                85                  90                  95

GGT GAT ACT GTT GAA GTA GAG TGC TGG GTT GGT GCA TCG GGA AAT AAT         337
Gly Asp Thr Val Glu Val Glu Cys Trp Val Gly Ala Ser Gly Asn Asn
            100                 105                 110

GGC AGG CGC CAT GAT TTC CTT GTC CGG GAC TGC AAA ACA GGC GAA ATT         385
Gly Arg Arg His Asp Phe Leu Val Arg Asp Cys Lys Thr Gly Glu Ile
        115                 120                 125

CTT ACA AGA TGT ACC AGT CTT TCG GTG ATG ATG AAT ACA AGG ACA AGG         433
Leu Thr Arg Cys Thr Ser Leu Ser Val Met Met Asn Thr Arg Thr Arg
    130                 135                 140

AGG TTG TCC AAA ATC CCT GAA GAA GTT AGA GGG GAG ATA GGG CCT GCA         481
Arg Leu Ser Lys Ile Pro Glu Glu Val Arg Gly Glu Ile Gly Pro Ala
145                 150                 155                 160

TTC ATT GAT AAT GTG GCT GTC AAA GAC GAG GAA ATT AAG AAA CCA CAG         529
Phe Ile Asp Asn Val Ala Val Lys Asp Glu Glu Ile Lys Lys Pro Gln
                165                 170                 175

AAG CTC AAT GAC AGC ACT GCA GAT TAC ATC CAA GGA GGA TTG ACT CCT         577
Lys Leu Asn Asp Ser Thr Ala Asp Tyr Ile Gln Gly Gly Leu Thr Pro
            180                 185                 190

CGA TGG AAT GAT TTG GAT ATC AAT CAG CAC GTT AAC AAC ATC AAA TAC         625
Arg Trp Asn Asp Leu Asp Ile Asn Gln His Val Asn Asn Ile Lys Tyr
        195                 200                 205

GTT GAC TGG ATT CTT GAG ACT GTC CCA GAC TCA ATC TTT GAG AGT CAT         673
Val Asp Trp Ile Leu Glu Thr Val Pro Asp Ser Ile Phe Glu Ser His
    210                 215                 220

CAT ATT TCC AGC TTC ACT ATT GAA TAC AGG AGA GAG TGC ACG AGG GAT         721
His Ile Ser Ser Phe Thr Ile Glu Tyr Arg Arg Glu Cys Thr Arg Asp
225                 230                 235                 240

AGC GTG CTG CAG TCC CTG ACC ACT GTC TCC GGT GGC TCG TCG GAA GCT         769
Ser Val Leu Gln Ser Leu Thr Thr Val Ser Gly Gly Ser Ser Glu Ala
                245                 250                 255
```

```
GGG TTA GTG TGC GAG CAC TTG CTC CAG CTT GAA GGT GGG TCT GAG GTA         817
Gly Leu Val Cys Glu His Leu Leu Gln Leu Glu Gly Gly Ser Glu Val
            260                 265                 270

TTG AGG GCA AAA ACA GAG TGG AGG CCT AAG CTT ACC GAT AGT TTC AGA         865
Leu Arg Ala Lys Thr Glu Trp Arg Pro Lys Leu Thr Asp Ser Phe Arg
            275                 280                 285

GGG ATT AGT GTG ATA CCC GCA GAA TCG AGT GTC TAACTAACGA AAGAAGCATC       918
Gly Ile Ser Val Ile Pro Ala Glu Ser Ser Val
            290                 295

TGATGAAGTT TCTCCTGTGC TGTTGTTCGT GAGGATGCTT TTTAGAAGCT GCAGTTTGCA        978

TTGCTTGTGC AGAATCATGG CCTGTGGTTT TAGATATATA TTCAAAATTG TCCTATAGTC       1038

AAGAAACTTA ATATCAGAAA AATAACTCAA TGAGTCAAGG TTATCGAAGT AGTCATGTAA       1098

GCTTTGAAAT ATGTTGTGTA TTCCTCGGCT TTATGTAATC TGTAAGCTCT TTCTCTTGC        1157

(2) INFORMATION FOR SEQ ID NO: 8:

(i) SEQUENCE CHARACTERISTICS:
        (A) LENGTH: 1300 base pairs
        (B) TYPE:   nucleic acid
        (C) STRANDEDNESS: single
        (D) TOPOLOGY:    linear (ii) MOLECULE TYPE:   cDNA to mRNA (xi) SEQUENCE DESCRIPTION: SEQ ID NO: 8:

CCAAG ATG TTG AAG CTC TCT TCT TCC CGA AGC CCA TTG GCC CGC ATT CCC        50
      Met Leu Lys Leu Ser Ser Ser Arg Ser Pro Leu Ala Arg Ile Pro
                        5                  10                  15

ACC CGG CCC AGG CCC AAC TCC ATT CCT CCC CGG ATA ATT GTG GTT TCC         98
Thr Arg Pro Arg Pro Asn Ser Ile Pro Pro Arg Ile Ile Val Val Ser
            20                  25                  30

TCC TCA TCC AGC AAG GTT AAT CCA CTC AAA ACA GAG GCG GTG GTT TCT        146
Ser Ser Ser Ser Lys Val Asn Pro Leu Lys Thr Glu Ala Val Val Ser
            35                  40                  45

TCG GGG CTG GCT GAC CGG CTC CGG CTG GGC AGC TTG ACC GAG GAC GGG        194
Ser Gly Leu Ala Asp Arg Leu Arg Leu Gly Ser Leu Thr Glu Asp Gly
            50                  55                  60

CTT TCG TAT AAG GAG AAG TTC ATA GTG AGA TGC TAT GAG GTT GGG ATT        242
Leu Ser Tyr Lys Glu Lys Phe Ile Val Arg Cys Tyr Glu Val Gly Ile
            65                  70                  75

AAC AAG ACC GCT ACT GTT GAG ACT ATT GCC AAC CTC TTG CAG GAG GTT        290
Asn Lys Thr Ala Thr Val Glu Thr Ile Ala Asn Leu Leu Gln Glu Val
80                  85                  90                  95

GGA TGC AAT CAC GCC CAA AGC GTT GGA TAT TCG ACG GGT GGG TTT TCG        338
Gly Cys Asn His Ala Gln Ser Val Gly Tyr Ser Thr Gly Gly Phe Ser
            100                 105                 110

ACA ACC CCT ACC ATG AGA AAA TTG CGT CTG ATA TGG GTT ACT GCT CGC        386
Thr Thr Pro Thr Met Arg Lys Leu Arg Leu Ile Trp Val Thr Ala Arg
            115                 120                 125

ATG CAC ATC GAA ATC TAC AAA TAT CCA GCT TGG AGT GAT GTG GTG GAA        434
Met His Ile Glu Ile Tyr Lys Tyr Pro Ala Trp Ser Asp Val Val Glu
            130                 135                 140

ATA GAG TCG TGG GGC CAG GGT GAA GGA AAA ATC GGA ACC AGA CGT GAT        482
Ile Glu Ser Trp Gly Gln Gly Glu Gly Lys Ile Gly Thr Arg Arg Asp
            145                 150                 155

TGG ATT CTG AGA GAC TAT GCC ACT GGT CAA GTT ATT GGC CGA GCT ACT        530
Trp Ile Leu Arg Asp Tyr Ala Thr Gly Gln Val Ile Gly Arg Ala Thr
160                 165                 170                 175

AGC AAG TGG GTA ATG ATG AAC CAA GAC ACC AGG CGA CTT CAA AAA GTC        578
Ser Lys Trp Val Met Met Asn Gln Asp Thr Arg Arg Leu Gln Lys Val
                180                 185                 190
```

```
GAT GTT GAT GTT CGT GAT GAG TAC TTG GTT CAC TGT CCA AGA GAA CTC         626
Asp Val Asp Val Arg Asp Glu Tyr Leu Val His Cys Pro Arg Glu Leu
            195                 200                 205

AGA TTG GCA TTT CCA GAG GAA AAT AAT AGC AGC TTG AAG AAA ATT TCA         674
Arg Leu Ala Phe Pro Glu Glu Asn Asn Ser Ser Leu Lys Lys Ile Ser
        210                 215                 220

AAA CTT GAA GAT CCT TCT CAA TAT TCG AAG CTG GGG CTT GTG CCT AGA         722
Lys Leu Glu Asp Pro Ser Gln Tyr Ser Lys Leu Gly Leu Val Pro Arg
    225                 230                 235

AGA GCA GAT CTG GAC ATG AAT CAA CAT GTT AAT AAT GTC ACC TAT ATT         770
Arg Ala Asp Leu Asp Met Asn Gln His Val Asn Asn Val Thr Tyr Ile
240                 245                 250                 255

GGA TGG GTG TTG GAG AGC ATG CCT CAA GAA ATC ATT GAT ACC CAT GAA         818
Gly Trp Val Leu Glu Ser Met Pro Gln Glu Ile Ile Asp Thr His Glu
            260                 265                 270

CTG CAA ACC ATA ACA TTA GAC TAC AGA CGG GAA TGC CAA CAT GAT GAT         866
Leu Gln Thr Ile Thr Leu Asp Tyr Arg Arg Glu Cys Gln His Asp Asp
        275                 280                 285

GTG GTT GAT TCC TTG ACT AGT CCA GAG CCT TCT GAA GAT GCT GAA GCA         914
Val Val Asp Ser Leu Thr Ser Pro Glu Pro Ser Glu Asp Ala Glu Ala
    290                 295                 300

GTT TTC AAC CAT AAT GGA ACA AAT GGG TCT GCA AAT GTG AGC GCC AAC         962
Val Phe Asn His Asn Gly Thr Asn Gly Ser Ala Asn Val Ser Ala Asn
305                 310                 315

GAC CAT GGA TGC CGC AAC TTT CTG CAT CTA CTA AGA TTG TCG GGC AAT        1010
Asp His Gly Cys Arg Asn Phe Leu His Leu Leu Arg Leu Ser Gly Asn
320                 325                 330                 335

GGA CTT GAA ATC AAC CGT GGT CGT ACT GAG TGG AGA AAG AAA CCT ACA        1058
Gly Leu Glu Ile Asn Arg Gly Arg Thr Glu Trp Arg Lys Lys Pro Thr
            340                 345                 350

AGA TGAGGCAATA AAGTACATTA TGTACTTTAT CGTTGCTTTA GCCGGCTTCT             1111
Arg

GGATGGTGAT TCTTTCTGC ATTCCTTCTT TCCTTTTTGT TTTCCTAGGG TATCCTTCGC       1171

TTCTTGCCTG TAAGAGTATT ATGTTTTCCG TTTGCCCTGA AGTTGTAAAT TTGTCGAGGA      1231

ACTCGAGTCA TTGTTTGAAT CGAGGATGGT GAGAAGTGTA CTTGTTTGTT GTATTCCATT      1291

CTTCCTGAT                                                              1300

(2) INFORMATION FOR SEQ ID NO: 9:

(i) SEQUENCE CHARACTERISTICS:
        (A) LENGTH: 1314 base pairs
        (B) TYPE:   nucleic acid
        (C) STRANDEDNESS: single
        (D) TOPOLOGY:    linear (ii) MOLECULE TYPE:   cDNA to mRNA (xi) SEQUENCE DESCRIPTION: SEQ ID NO: 9:

CACTCAAGAA AAAGGGCACC AATTGAACGC TACAACGGAG TAACCAAAG ATG TTT AAG       58
                                                      Met Phe Lys

ATC TCC TCT TCC CTG AGC CCA GTG GAC CAA ATC CCC CCC ATT TCC CCA        106
Ile Ser Ser Ser Leu Ser Pro Val Asp Gln Ile Pro Pro Ile Ser Pro
    5                   10                  15

CTG CCC AGG CCC AGG CCC AGG CCC ATT ACC CCC CGT GTT TTG GCC GTC        154
Leu Pro Arg Pro Arg Pro Arg Pro Ile Thr Pro Arg Val Leu Ala Val
20                  25                  30                  35

TCT TCT TCC TCT GGA AAG ATC GTT AAT AAT CCC CTT AAA GCG GAG ACT        202
Ser Ser Ser Ser Gly Lys Ile Val Asn Asn Pro Leu Lys Ala Glu Thr
            40                  45                  50
```

| | |
|---|---:|
| ACG GAG GCG GTT TCC GGG GAG TTA GCG CGC CGT TTC CGG CTT GGG AGG<br>Thr Glu Ala Val Ser Gly Glu Leu Ala Arg Arg Phe Arg Leu Gly Arg<br>              55                       60                     65 | 250 |
| TTG GCT GAG GAC GGG TTT TCG TAT AAG GAG AAG TTT ATA GTG AGG TGT<br>Leu Ala Glu Asp Gly Phe Ser Tyr Lys Glu Lys Phe Ile Val Arg Cys<br>70                       75                       80 | 298 |
| TAT GAG GTT GGA ATT AAC AAG ACC GCC ACT GTT GAG ACT CTT GCC AAT<br>Tyr Glu Val Gly Ile Asn Lys Thr Ala Thr Val Glu Thr Leu Ala Asn<br>    85                     90                       95 | 346 |
| CTC TTA CAG GAG GTT GGA GGC AAT CAC GCC CAA AGT GTT GGA TTT TCG<br>Leu Leu Gln Glu Val Gly Gly Asn His Ala Gln Ser Val Gly Phe Ser<br>100                   105                 110              115 | 394 |
| ACG GAT GGG TTT GCG ACA ACC CAT TCC ATG AGA AAG ATG CAT CTG ATA<br>Thr Asp Gly Phe Ala Thr Thr His Ser Met Arg Lys Met His Leu Ile<br>                  120                 125              130 | 442 |
| TGG GTT ACA GCT CGC ATG CAC ATA GAA ATA TAC AAA TAT CCA GCT TGG<br>Trp Val Thr Ala Arg Met His Ile Glu Ile Tyr Lys Tyr Pro Ala Trp<br>              135                 140              145 | 490 |
| AGT GAT GTG ATA GAA GTA GAG ACG TGG ATT GGG GCC GAA GGA AGA ATT<br>Ser Asp Val Ile Glu Val Glu Thr Trp Ile Gly Ala Glu Gly Arg Ile<br>          150                 155              160 | 538 |
| GGA ACT AGA CGT AAT TGG ATT ATT AAG GAC TGT GCC ACT GAT GAA GTT<br>Gly Thr Arg Arg Asn Trp Ile Ile Lys Asp Cys Ala Thr Asp Glu Val<br>165                   170                 175 | 586 |
| ATT GGC CGA GCT ACT AGC AAG TGG GTT ATG ATG AAC CAA GAT ACC AGG<br>Ile Gly Arg Ala Thr Ser Lys Trp Val Met Met Asn Gln Asp Thr Arg<br>180                     185               190             195 | 634 |
| CGA CTT GAA AAG GTT TCA GAT GAT GTT CGT GAG GAG CAC TTG GTT TTC<br>Arg Leu Glu Lys Val Ser Asp Asp Val Arg Glu Glu His Leu Val Phe<br>              200                 205              210 | 682 |
| AGT CCG AGA GAG CCA AGA TTG CCA TTT CCG GAT GAA AAT AAT AGC AGC<br>Ser Pro Arg Glu Pro Arg Leu Pro Phe Pro Asp Glu Asn Asn Ser Ser<br>                 215                 220              225 | 730 |
| TTG AAG AAA ATT TCC AAA CTT GAC GAT CCT GCT CAA TAT TCC AAG CTA<br>Leu Lys Lys Ile Ser Lys Leu Asp Asp Pro Ala Gln Tyr Ser Lys Leu<br>          230                 235                 240 | 778 |
| AGT CTT GAG CCT AGA AGA GGA GAT CTG GAC ATG AAT CAG CAT GTT AAT<br>Ser Leu Glu Pro Arg Arg Gly Asp Leu Asp Met Asn Gln His Val Asn<br>245                   250                 255 | 826 |
| AAC GTC ACC TAT ATT GGA TGG GTG TTG GAG AGC ATG CCT CAA GAA ATC<br>Asn Val Thr Tyr Ile Gly Trp Val Leu Glu Ser Met Pro Gln Glu Ile<br>260                     265               270             275 | 874 |
| ATA GAC ACC CAT GAA CTA CAG ACA ATA ACA TTA GAC TAC CGA AGG GAA<br>Ile Asp Thr His Glu Leu Gln Thr Ile Thr Leu Asp Tyr Arg Arg Glu<br>              280                 285              290 | 922 |
| TGC CAA CAT GAT GAC TTG GTT GAT TCC TTG ACT AGT CCG GAG CCT TCT<br>Cys Gln His Asp Asp Leu Val Asp Ser Leu Thr Ser Pro Glu Pro Ser<br>                 295                 300              305 | 970 |
| GAG TTC TCA GAA ACA ACA AAT GGA TCG GCA AAT GTG AGC CCC AAC GAC<br>Glu Phe Ser Glu Thr Thr Asn Gly Ser Ala Asn Val Ser Pro Asn Asp<br>          310                 315                 320 | 1018 |
| AAT CGA TGC CTC AAC TTT TTG CAT CTA CTG AGA CTG TCA AGT GAT GGG<br>Asn Arg Cys Leu Asn Phe Leu His Leu Leu Arg Leu Ser Ser Asp Gly<br>325                   330                 335 | 1066 |
| AGT GAA ATC AAC CGT GGT CGT ACT GTG TGG AGA AAG AAA CCT GCA AAA<br>Ser Glu Ile Asn Arg Gly Arg Thr Val Trp Arg Lys Lys Pro Ala Lys<br>340                   345                 350              355 | 1114 |
| TGAGGCAATA ATTACACAC TACTTAATTG TTGCTTTTTC CAGCTTCGTG TGGGTGGTGG | 1174 |
| TTTTTTTTGT TGGTTCATTT TTATGGTTTT TGGTTGGCCA TCAATTACGT TGGTGAGAAT | 1234 |

```
AGTGTTATGG ATTTGGTGTG AGATTCTTTT ACATCAAAGA AACGATGTGA GATTCTTTTA    1294

CATCAAATTT TTCATAAACG                                                1314

(2) INFORMATION FOR SEQ ID NO: 10:

(i) SEQUENCE CHARACTERISTICS:
        (A) LENGTH: 1459 base pairs
        (B) TYPE:   nucleic acid
        (C) STRANDEDNESS:  single
        (D) TOPOLOGY:  linear (ii) MOLECULE TYPE:   cDNA to mRNA (xi) SEQUENCE DESCRIPTION: SEQ ID NO: 10:

CCACGCGTCC GTGAGTTTGC TGGATACCAT TTTCCCTGCG AAGAAAC ATG GTG GCT       56
                                                    Met Val Ala
                                                      1

GCT GCA GCA AGT TCT GCA TGC TTC CCT GTT CCA TCC CCA GGA GCC TCC      104
Ala Ala Ala Ser Ser Ala Cys Phe Pro Val Pro Ser Pro Gly Ala Ser
          5                  10                  15

CCT AAA CCT GGG AAG TTA GGC AAC TGG TCA TCG AGT TTG AGC CCT TCC      152
Pro Lys Pro Gly Lys Leu Gly Asn Trp Ser Ser Ser Leu Ser Pro Ser
 20              25                  30                  35

TTG AAG CCC AAG TCA ATC CCC AAT GGA GGA TTT CAG GTT AAG GCA AAT      200
Leu Lys Pro Lys Ser Ile Pro Asn Gly Gly Phe Gln Val Lys Ala Asn
                 40                  45                  50

GCC AGT GCG CAT CCT AAG GCT AAC GGT TCT GCA GTA ACT CTA AAG TCT      248
Ala Ser Ala His Pro Lys Ala Asn Gly Ser Ala Val Thr Leu Lys Ser
             55                  60                  65

GGC AGC CTC AAC ACT CAG GAG GAC ACT TTG TCG TCG TCC CCT CCT CCC      296
Gly Ser Leu Asn Thr Gln Glu Asp Thr Leu Ser Ser Ser Pro Pro Pro
         70                  75                  80

CGG GCT TTT TTT AAC CAG TTG CCT GAT TGG AGT ATG CTT CTG ACT GCA      344
Arg Ala Phe Phe Asn Gln Leu Pro Asp Trp Ser Met Leu Leu Thr Ala
 85                  90                  95

ATC ACA ACC GTC TTC GTG GCA CCA GAG AAG CGG TGG ACT ATG TTT GAT      392
Ile Thr Thr Val Phe Val Ala Pro Glu Lys Arg Trp Thr Met Phe Asp
100                 105                 110                 115

AGG AAA TCT AAG AGG CCT AAC ATG CTC ATG GAC TCG TTT GGG TTG GAG      440
Arg Lys Ser Lys Arg Pro Asn Met Leu Met Asp Ser Phe Gly Leu Glu
                120                 125                 130

AGA GTT GTT CAG GAT GGG CTC GTG TTC AGA CAG AGT TTT TCG ATT AGG      488
Arg Val Val Gln Asp Gly Leu Val Phe Arg Gln Ser Phe Ser Ile Arg
            135                 140                 145

TCT TAT GAA ATA TGC GCT GAT CGA ACA GCC TCT ATA GAG ACG GTG ATG      536
Ser Tyr Glu Ile Cys Ala Asp Arg Thr Ala Ser Ile Glu Thr Val Met
        150                 155                 160

AAC CAC GTC CAG GAA ACA TCA CTC AAT CAA TGT AAG AGT ATA GGT CTT      584
Asn His Val Gln Glu Thr Ser Leu Asn Gln Cys Lys Ser Ile Gly Leu
    165                 170                 175

CTC GAT GAC GGC TTT GGT CGT AGT CCT GAG ATG TGT AAA AGG GAC CTC      632
Leu Asp Asp Gly Phe Gly Arg Ser Pro Glu Met Cys Lys Arg Asp Leu
180                 185                 190                 195

ATT TGG GTG GTT ACA AGA ATG AAG ATA ATG GTG AAT CGC TAT CCA ACT      680
Ile Trp Val Val Thr Arg Met Lys Ile Met Val Asn Arg Tyr Pro Thr
                200                 205                 210

TGG GGC GAT ACT ATC GAG GTC AGT ACC TGG CTC TCT CAA TCG GGG AAA      728
Trp Gly Asp Thr Ile Glu Val Ser Thr Trp Leu Ser Gln Ser Gly Lys
            215                 220                 225

ATC GGT ATG GGT CGC GAT TGG CTA ATA AGT GAT TGC AAC ACA GGA GAA      776
Ile Gly Met Gly Arg Asp Trp Leu Ile Ser Asp Cys Asn Thr Gly Glu
        230                 235                 240
```

```
ATT CTT GTA AGA GCA ACG AGT GTG TAT GCC ATG ATG AAT CAA AAG ACG        824
Ile Leu Val Arg Ala Thr Ser Val Tyr Ala Met Met Asn Gln Lys Thr
    245                 250                 255

AGA AGA TTC TCA AAA CTC CCA CAC GAG GTT CGC CAG GAA TTT GCG CCT        872
Arg Arg Phe Ser Lys Leu Pro His Glu Val Arg Gln Glu Phe Ala Pro
260                 265                 270                 275

CAT TTT CTG GAC TCT CCT CCT GCC ATT GAA GAC AAC GAC GGT AAA TTG        920
His Phe Leu Asp Ser Pro Pro Ala Ile Glu Asp Asn Asp Gly Lys Leu
                280                 285                 290

CAG AAG TTT GAT GTG AAG ACT GGT GAT TCC ATT CGC AAG GGT CTA ACT        968
Gln Lys Phe Asp Val Lys Thr Gly Asp Ser Ile Arg Lys Gly Leu Thr
        295                 300                 305

CCG GGG TGG TAT GAC TTG GAT GTC AAT CAG CAC GTA AGC AAC GTG AAG       1016
Pro Gly Trp Tyr Asp Leu Asp Val Asn Gln His Val Ser Asn Val Lys
            310                 315                 320

TAC ATT GGG TGG ATT CTC GAG AGT ATG CCA ACA GAA GTT TTG GAG ACT       1064
Tyr Ile Gly Trp Ile Leu Glu Ser Met Pro Thr Glu Val Leu Glu Thr
    325                 330                 335

CAG GAG CTA TGT TCT CTC ACC CTT GAA TAT AGG CGG GAA TGC GGA AGG       1112
Gln Glu Leu Cys Ser Leu Thr Leu Glu Tyr Arg Arg Glu Cys Gly Arg
340                 345                 350                 355

GAC AGT GTG CTG GAG TCC GTG ACC TCT ATG GAT CCC TCA AAA GTT GGA       1160
Asp Ser Val Leu Glu Ser Val Thr Ser Met Asp Pro Ser Lys Val Gly
                360                 365                 370

GAC CGG TTT CAG TAC CGG CAC CTT CTG CGG CTT GAG GAT GGG GCT GAT       1208
Asp Arg Phe Gln Tyr Arg His Leu Leu Arg Leu Glu Asp Gly Ala Asp
        375                 380                 385

ATC ATG AAG GGA AGA ACT GAG TGG CGG CCG AAG AAT GCA GGA ACT AAC       1256
Ile Met Lys Gly Arg Thr Glu Trp Arg Pro Lys Asn Ala Gly Thr Asn
            390                 395                 400

GGG GCG ATA TCA ACA GGA AAG ACT TGAAATGAA ACTCTGTCTC TTAGAATAAT       1310
Gly Ala Ile Ser Thr Gly Lys Thr
        405                 410

CTCGGGATTC TTCCGGGATG TGCATTTCTT TTCTCTTTTT CATTTCCTGG TGAGCTGAAA     1370

GAAGAGCATG TGGTTGTGGT TGCAAGCAGT AAACTGTGTA GTTCGTTTGT TCGCTTTGCA     1430

TCGAAACCTT TGTATAATAA TATGATCTG                                      1459

(2) INFORMATION FOR SEQ ID NO: 11:

(i) SEQUENCE CHARACTERISTICS:
        (A) LENGTH: 1408 base pairs
        (B) TYPE:   nucleic acid
        (C) STRANDEDNESS: single
        (D) TOPOLOGY:   linear (ii) MOLECULE TYPE:  cDNA to mRNA (xi) SEQUENCE DESCRIPTION: SEQ ID NO: 11:

CCACGCGTCC GCTGAGTTTG CTGGTTACCA TTTTCCCTGC GAACAAAC ATG GTG GCT        57
                                                    Met Val Ala
                                                     1

GCC GCA GCA AGT GCT GCA TTC TTC TCC GTC GCA ACC CCG CGA ACA AAC        105
Ala Ala Ala Ser Ala Ala Phe Phe Ser Val Ala Thr Pro Arg Thr Asn
    5                   10                  15

ATT TCG CCA TCG AGC TTG AGC GTC CCC TTC AAG CCC AAA TCA AAC CAC        153
Ile Ser Pro Ser Ser Leu Ser Val Pro Phe Lys Pro Lys Ser Asn His
20                  25                  30                  35

AAT GGT GGC TTT CAG GTT AAG GCA AAC GCC AGT GCC CAT CCT AAG GCT        201
Asn Gly Gly Phe Gln Val Lys Ala Asn Ala Ser Ala His Pro Lys Ala
            40                  45                  50
```

-continued

| | |
|---|---|
| AAC GGT TCT GCA GTA AGT CTA AAG TCT GGC AGC CTC GAG ACT CAG GAG<br>Asn Gly Ser Ala Val Ser Leu Lys Ser Gly Ser Leu Glu Thr Gln Glu<br>     55       60       65 | 249 |
| GAC AAA ACT TCA TCG TCG TCC CCT CCT CCT CGG ACT TTC ATT AAC CAG<br>Asp Lys Thr Ser Ser Ser Ser Pro Pro Pro Arg Thr Phe Ile Asn Gln<br>   70       75       80 | 297 |
| TTG CCC GTC TGG AGT ATG CTT CTG TCT GCA GTC ACG ACT GTC TTC GGG<br>Leu Pro Val Trp Ser Met Leu Leu Ser Ala Val Thr Thr Val Phe Gly<br>85       90       95 | 345 |
| GTG GCT GAG AAG CAG TGG CCA ATG CTT GAC CGG AAA TCT AAG AGG CCC<br>Val Ala Glu Lys Gln Trp Pro Met Leu Asp Arg Lys Ser Lys Arg Pro<br>100       105      110      115 | 393 |
| GAC ATG CTT GTG GAA CCG CTT GGG GTT GAC AGG ATT GTT TAT GAT GGG<br>Asp Met Leu Val Glu Pro Leu Gly Val Asp Arg Ile Val Tyr Asp Gly<br>       120      125      130 | 441 |
| GTT AGT TTC AGA CAG AGT TTT TCG ATT AGA TCT TAC GAA ATA GGC GCT<br>Val Ser Phe Arg Gln Ser Phe Ser Ile Arg Ser Tyr Glu Ile Gly Ala<br>     135       140      145 | 489 |
| GAT CGA ACA GCC TCG ATA GAG ACC CTG ATG AAC ATG TTC CAG GAA ACA<br>Asp Arg Thr Ala Ser Ile Glu Thr Leu Met Asn Met Phe Gln Glu Thr<br>150       155      160 | 537 |
| TCT CTT AAT CAT TGT AAG ATT ATC GGT CTT CTC AAT GAC GGC TTT GGT<br>Ser Leu Asn His Cys Lys Ile Ile Gly Leu Leu Asn Asp Gly Phe Gly<br>   165       170      175 | 585 |
| CGA ACT CCT GAG ATG TGT AAG AGG GAC CTC ATT TGG GTG GTC ACG AAA<br>Arg Thr Pro Glu Met Cys Lys Arg Asp Leu Ile Trp Val Val Thr Lys<br>180       185      190      195 | 633 |
| ATG CAG ATC GAG GTG AAT CGC TAT CCT ACT TGG GGT GAT ACT ATA GAG<br>Met Gln Ile Glu Val Asn Arg Tyr Pro Thr Trp Gly Asp Thr Ile Glu<br>       200      205      210 | 681 |
| GTC AAT ACT TGG GTC TCA GCG TCG GGG AAA CAC GGT ATG GGT CGA GAT<br>Val Asn Thr Trp Val Ser Ala Ser Gly Lys His Gly Met Gly Arg Asp<br>     215       220      225 | 729 |
| TGG CTG ATA AGT GAT TGC CAT ACA GGA GAA ATT CTT ATA AGA GCA ACG<br>Trp Leu Ile Ser Asp Cys His Thr Gly Glu Ile Leu Ile Arg Ala Thr<br>   230       235      240 | 777 |
| AGC GTG TGG GCT ATG ATG AAT CAA AAG ACG AGA AGA TTG TCG AAA ATT<br>Ser Val Trp Ala Met Met Asn Gln Lys Thr Arg Arg Leu Ser Lys Ile<br>245       250      255 | 825 |
| CCA TAT GAG GTT CGA CAG GAG ATA GAG CCT CAG TTT GTG GAC TCT GCT<br>Pro Tyr Glu Val Arg Gln Glu Ile Glu Pro Gln Phe Val Asp Ser Ala<br>260       265      270      275 | 873 |
| CCT GTC ATT GTA GAC GAT CGA AAA TTT CAC AAG CTT GAT TTG AAG ACC<br>Pro Val Ile Val Asp Asp Arg Lys Phe His Lys Leu Asp Leu Lys Thr<br>       280      285      290 | 921 |
| GGT GAT TCC ATT TGC AAT GGT CTA ACT CCA AGG TGG ACT GAC TTG GAT<br>Gly Asp Ser Ile Cys Asn Gly Leu Thr Pro Arg Trp Thr Asp Leu Asp<br>     295       300      305 | 969 |
| GTC AAT CAG CAC GTT AAC AAT GTG AAA TAC ATC GGG TGG ATT CTC CAG<br>Val Asn Gln His Val Asn Asn Val Lys Tyr Ile Gly Trp Ile Leu Gln<br>   310       315      320 | 1017 |
| AGT GTT CCC ACA GAA GTT TTC GAG ACG CAG GAG CTA TGT GGC CTC ACC<br>Ser Val Pro Thr Glu Val Phe Glu Thr Gln Glu Leu Cys Gly Leu Thr<br>325       330      335 | 1065 |
| CTT GAG TAT AGG CGA GAA TGC GGA AGG GAC AGT GTG CTG GAG TCC GTG<br>Leu Glu Tyr Arg Arg Glu Cys Gly Arg Asp Ser Val Leu Glu Ser Val<br>340       345      350      355 | 1113 |
| ACC GCT ATG GAT CCA TCA AAA GAG GGA GAC CGG TCT CTT TAC CAG CAC<br>Thr Ala Met Asp Pro Ser Lys Glu Gly Asp Arg Ser Leu Tyr Gln His<br>       360      365      370 | 1161 |

```
CTT CTC CGA CTC GAG GAC GGG GCT GAT ATC GTC AAG GGG AGA ACC GAG    1209
Leu Leu Arg Leu Glu Asp Gly Ala Asp Ile Val Lys Gly Arg Thr Glu
            375                 380                 385

TGG CGG CCG AAG AAT GCA GGA GCC AAG GGA GCA ATA TTA ACC GGA AAG    1257
Trp Arg Pro Lys Asn Ala Gly Ala Lys Gly Ala Ile Leu Thr Gly Lys
            390                 395                 400

ACC TCA AAT GGA AAC TCT ATA TCT TAGAAGGAGG AAGGGACCTT TCCGAGTTGT   1311
Thr Ser Asn Gly Asn Ser Ile Ser
            405             410

GTGTTTATTT GCTTTGCTTT GATTCACTCC ATTGTATAAT AATACTACGG TCAGCCGTCT  1371

TTGTATTTGC TAAGACAAAT AGCACAGTCA TTAAGTT                           1408

(2) INFORMATION FOR SEQ ID NO: 12:

(i) SEQUENCE CHARACTERISTICS:
        (A) LENGTH: 29 base pairs
        (B) TYPE:   nucleic acid
        (C) STRANDEDNESS: single
        (D) TOPOLOGY:    linear (ii) MOLECULE TYPE:   other
        (A) DESCRIPTION: synthetic oligonucleotide (xi) SEQUENCE DESCRIPTION: SEQ ID NO: 12:

CUACUACUAC UASYNTVNGY NATGATGAA                                    29

(2) INFORMATION FOR SEQ ID NO: 13:

(i) SEQUENCE CHARACTERISTICS:
        (A) LENGTH: 30 base pairs
        (B) TYPE:   nucleic acid
        (C) STRANDEDNESS: single
        (D) TOPOLOGY:    linear (ii) MOLECULE TYPE:   other
        (A) DESCRIPTION: synthetic oligonucleotide (xi) SEQUENCE DESCRIPTION: SEQ ID NO: 13:

CAUCAUCAUC AURCAYTCNC KNCKRTANTC                                   30

(2) INFORMATION FOR SEQ ID NO: 14:

(i) SEQUENCE CHARACTERISTICS:
        (A) LENGTH: 35 base pairs
        (B) TYPE:   nucleic acid
        (C) STRANDEDNESS: single
        (D) TOPOLOGY:    linear (ii) MOLECULE TYPE:   other
        (A) DESCRIPTION: synthetic oligonucleotide (xi) SEQUENCE DESCRIPTION: SEQ ID NO: 14:

AUGGAGAUCU CUGAWCRBTA YCCTAMHTGG GGWGA                             35

(2) INFORMATION FOR SEQ ID NO: 15:

(i) SEQUENCE CHARACTERISTICS:
        (A) LENGTH: 29 base pairs
        (B) TYPE:   nucleic acid
        (C) STRANDEDNESS: single
        (D) TOPOLOGY:    linear (ii) MOLECULE TYPE:   other
        (A) DESCRIPTION: synthetic oligonucleotide (xi) SEQUENCE DESCRIPTION: SEQ ID NO: 15:

ACGCGUACUA GUTTNKKNCK CCAYTCNGT                                    29
```

(2) INFORMATION FOR SEQ ID NO: 16:

(i) SEQUENCE CHARACTERISTICS:
        (A) LENGTH: 34 base pairs
        (B) TYPE:   nucleic acid
        (C) STRANDEDNESS:  single
        (D) TOPOLOGY:   linear (ii) MOLECULE TYPE:   other
        (A) DESCRIPTION: synthetic oligonucleotide (xi) SEQUENCE DESCRIPTION: SEQ ID NO: 16:

GGAAATAATG GCCGACGACA TGATTTCCTT GTCC                                    34

(2) INFORMATION FOR SEQ ID NO: 17:

(i) SEQUENCE CHARACTERISTICS:
        (A) LENGTH: 16 base pairs
        (B) TYPE:   nucleic acid
        (C) STRANDEDNESS:  single
        (D) TOPOLOGY:   linear (ii) MOLECULE TYPE:   other
        (A) DESCRIPTION: synthetic oligonucleotide (xi) SEQUENCE DESCRIPTION: SEQ ID NO: 17:

GGTTGTCCAA AATCCC                                                            16

(2) INFORMATION FOR SEQ ID NO: 18:

(i) SEQUENCE CHARACTERISTICS:
        (A) LENGTH: 20 base pairs
        (B) TYPE:   nucleic acid
        (C) STRANDEDNESS:  single
        (D) TOPOLOGY:   linear (ii) MOLECULE TYPE:   other
        (A) DESCRIPTION: synthetic oligonucleotide (xi) SEQUENCE DESCRIPTION: SEQ ID NO: 18:

GCGTGCTGCA GTCCCTGACC                                                     20

(2) INFORMATION FOR SEQ ID NO: 19:

(i) SEQUENCE CHARACTERISTICS:
        (A) LENGTH: 40 base pairs
        (B) TYPE:   nucleic acid
        (C) STRANDEDNESS:  single
        (D) TOPOLOGY:   linear (ii) MOLECULE TYPE:   other
        (A) DESCRIPTION: synthetic oligonucleotide (xi) SEQUENCE DESCRIPTION: SEQ ID NO: 19:

GAGAGAGTGC ACGATGGATA GCGTGCTGCA GTCCCTGACC                       40

(2) INFORMATION FOR SEQ ID NO: 20:

(i) SEQUENCE CHARACTERISTICS:
        (A) LENGTH: 6 amino acids
        (B) TYPE:   amino acid
        (D) TOPOLOGY:   linear (ii) MOLECULE TYPE:   protein (ix) FEATURE:
        (D) OTHER INFORMATION: Xaa 1 = Val, Leu, or Ala
            Xaa 2 = Trp, Ser, or Tyr
            Xaa 3 = Val or Ala (xi) SEQUENCE DESCRIPTION: SEQ ID NO: 20:

```
Xaa Xaa Xaa Met Met Asn
              5                                                    6

(2) INFORMATION FOR SEQ ID NO: 21:

(i) SEQUENCE CHARACTERISTICS:
          (A) LENGTH: 6 amino acids
          (B) TYPE:   amino acid
          (D) TOPOLOGY:  linear (ii) MOLECULE TYPE:   protein (ix) FEATURE:
          (D) OTHER INFORMATION:   Xaa = Asp or Glu (xi) SEQUENCE DESCRIPTION: SEQ ID NO: 21:

Xaa Tyr Arg Arg Glu Cys
              5                                                    6

(2) INFORMATION FOR SEQ ID NO: 22:

(i) SEQUENCE CHARACTERISTICS:
          (A) LENGTH: 8 amino acids
          (B) TYPE:   amino acid
          (D) TOPOLOGY:  linear (ii) MOLECULE TYPE:   protein (ix) FEATURE:
          (D) OTHER INFORMATION:   Xaa 1 = Glu or Asp
              Xaa 2 = His or Arg
              Xaa 3 = Lys or Thr (xi) SEQUENCE DESCRIPTION: SEQ ID NO: 22:

Xaa Xaa Tyr Pro Xaa Trp Gly Asp
              5                                                    8

(2) INFORMATION FOR SEQ ID NO: 23:

(i) SEQUENCE CHARACTERISTICS:
          (A) LENGTH: 6 amino acids
          (B) TYPE:   amino acid
          (D) TOPOLOGY:  linear (ii) MOLECULE TYPE:   protein (ix) FEATURE:
          (D) OTHER INFORMATION:   Xaa = Lys or Pro (xi) SEQUENCE DESCRIPTION: SEQ ID NO: 23:

Thr Glu Trp Arg Xaa Lys
              5                                                    6

(2) INFORMATION FOR SEQ ID NO: 24:

(i) SEQUENCE CHARACTERISTICS:
          (A) LENGTH: 299 residues
          (B) TYPE:   amino acid
          (D) TOPOLOGY:  linear (ii) MOLECULE TYPE:   protein (ix) FEATURE:
          (D) OTHER INFORMATION:   Xaa = Lys or Pro (xi) SEQUENCE DESCRIPTION: SEQ ID NO: 24:

Leu Glu Trp Lys Pro Lys Pro Asn Pro Pro Gln Leu Leu Asp Asp His
 1               5                  10                  15

Phe Gly Pro His Gly Leu Val Phe Arg Arg Thr Phe Ala Ile Arg Ser
            20                  25                  30
```

```
Tyr Glu Val Gly Pro Asp Arg Ser Thr Ser Ile Val Ala Val Met Asn
         35                  40                  45

His Leu Gln Glu Ala Ala Leu Asn His Ala Lys Ser Val Gly Ile Leu
 50                  55                  60

Gly Asp Gly Phe Gly Thr Thr Leu Glu Met Ser Lys Arg Asp Leu Ile
 65                  70                  75                  80

Trp Val Val Lys Arg Thr His Val Ala Val Glu Arg Tyr Pro Ala Trp
             85                  90                  95

Gly Asp Thr Val Glu Val Glu Cys Trp Val Gly Ala Ser Gly Asn Asn
            100                 105                 110

Gly Arg Arg His Asp Phe Leu Val Arg Asp Cys Lys Thr Gly Glu Ile
            115                 120                 125

Leu Thr Arg Cys Thr Ser Leu Ser Val Met Met Asn Thr Arg Thr Arg
130                 135                 140

Arg Leu Ser Lys Ile Pro Glu Glu Val Arg Gly Glu Ile Gly Pro Ala
145                 150                 155                 160

Phe Ile Asp Asn Val Ala Val Lys Asp Glu Glu Ile Lys Lys Pro Gln
                165                 170                 175

Lys Leu Asn Asp Ser Thr Ala Asp Tyr Ile Gln Gly Gly Leu Thr Pro
                180                 185                 190

Arg Trp Asn Asp Leu Asp Ile Asn Gln His Val Asn Asn Ile Lys Tyr
        195                 200                 205

Val Asp Trp Ile Leu Glu Thr Val Pro Asp Ser Ile Phe Glu Ser His
210                 215                 220

His Ile Ser Ser Phe Thr Ile Glu Tyr Arg Arg Glu Cys Thr Arg Asp
225                 230                 235                 240

Ser Val Leu Gln Ser Leu Thr Thr Val Ser Gly Ser Ser Glu Ala
                245                 250                 255

Gly Leu Val Cys Glu His Leu Leu Gln Leu Gly Gly Ser Glu Val
            260                 265                 270

Leu Arg Ala Lys Thr Glu Trp Arg Pro Lys Leu Thr Asp Ser Phe Arg
            275                 280                 285

Gly Ile Ser Val Ile Pro Ala Glu Ser Ser Val
290                 295

(2) INFORMATION FOR SEQ ID NO: 25:

(i) SEQUENCE CHARACTERISTICS:
        (A) LENGTH: 355 residues
        (B) TYPE:   amino acid
        (D) TOPOLOGY:   linear (ii) MOLECULE TYPE:   protein (ix) FEATURE:
        (D) OTHER INFORMATION:   Xaa = Lys or Pro (xi) SEQUENCE DESCRIPTION: SEQ ID NO: 25:

Met Phe Lys
                                            1

Ile Ser Ser Ser Leu Ser Pro Val Asp Gln Ile Pro Pro Ile Ser Pro
  5                  10                  15

Leu Pro Arg Pro Arg Pro Arg Pro Ile Thr Pro Arg Val Leu Ala Val
 20                  25                  30                  35

Ser Ser Ser Ser Gly Lys Ile Val Asn Asn Pro Leu Lys Ala Glu Thr
                 40                  45                  50
```

-continued

```
Thr Glu Ala Val Ser Gly Glu Leu Ala Arg Arg Phe Arg Leu Gly Arg
             55                  60                  65

Leu Ala Glu Asp Gly Phe Ser Tyr Lys Glu Lys Phe Ile Val Arg Cys
             70                  75                  80

Tyr Glu Val Gly Ile Asn Lys Thr Ala Thr Val Glu Thr Leu Ala Asn
     85                  90                  95

Leu Leu Gln Glu Val Gly Gly Asn His Ala Gln Ser Val Gly Phe Ser
100                 105                 110                 115

Thr Asp Gly Phe Ala Thr Thr His Ser Met Arg Lys Met His Leu Ile
                120                 125                 130

Trp Val Thr Ala Arg Met His Ile Glu Ile Tyr Lys Tyr Pro Ala Trp
                135                 140                 145

Ser Asp Val Ile Glu Val Glu Thr Trp Ile Gly Ala Glu Gly Arg Ile
            150                 155                 160

Gly Thr Arg Arg Asn Trp Ile Ile Lys Asp Cys Ala Thr Asp Glu Val
        165                 170                 175

Ile Gly Arg Ala Thr Ser Lys Trp Val Met Met Asn Gln Asp Thr Arg
180                 185                 190                 195

Arg Leu Glu Lys Val Ser Asp Asp Val Arg Glu Glu His Leu Val Phe
                200                 205                 210

Ser Pro Arg Glu Pro Arg Leu Pro Phe Pro Asp Glu Asn Asn Ser Ser
            215                 220                 225

Leu Lys Lys Ile Ser Lys Leu Asp Asp Pro Ala Gln Tyr Ser Lys Leu
        230                 235                 240

Ser Leu Glu Pro Arg Arg Gly Asp Leu Asp Met Asn Gln His Val Asn
    245                 250                 255

Asn Val Thr Tyr Ile Gly Trp Val Leu Glu Ser Met Pro Gln Glu Ile
260                 265                 270                 275

Ile Asp Thr His Glu Leu Gln Thr Ile Thr Leu Asp Tyr Arg Arg Glu
                280                 285                 290

Cys Gln His Asp Asp Leu Val Asp Ser Leu Thr Ser Pro Glu Pro Ser
            295                 300                 305

Glu Phe Ser Glu Thr Thr Asn Gly Ser Ala Asn Val Ser Pro Asn Asp
        310                 315                 320

Asn Arg Cys Leu Asn Phe Leu His Leu Leu Arg Leu Ser Ser Asp Gly
    325                 330                 335

Ser Glu Ile Asn Arg Gly Arg Thr Val Trp Arg Lys Lys Pro Ala Lys
340                 345                 350                 355
```

ENGINEERING PLANT THIOESTERASES FOR ALTERED SUBSTRATE SPECIFICITY

TECHNICAL FIELD

The present invention is directed to proteins, nucleic acid sequences and constructs, and methods related thereto.

INTRODUCTION

BACKGROUND

Fatty acids are organic acids having a hydrocarbon chain of from about 4 to 24 carbons. Many different kinds of fatty acids are known which differ from each other in chain length, and in the presence, number and position of double bonds. In cells, fatty acids typically exist in covalently bound forms, the carboxyl portion being referred to as a fatty acyl group. The chain length and degree of saturation of these molecules is often depicted by the formula CX:Y, where "X" indicates number of carbons and "Y" indicates number of double bands.

The production of fatty acids in plants begins in the plastid with the reaction between acetyl-CoA and malonyl-ACP (aryl carrier proteins) to produce butyryl-ACP catalyzed by the enzyme, β-ketoacyl-ACP synthase III. Elongation of acetyl-ACP to 16- and 18- carbon fatty acids involves the cyclical action of the following sequence of reactions: condensation with a two-carbon unit from malonyl-ACP to form a β-ketoacyl-ACP (β-ketoacyl-ACP synthase), reduction of the keto-function to an alcohol (β-ketoacyl-ACP reductase), dehydration to form an enoyl-ACP (β-hydroxyacyl-ACP dehydrase), and finally reduction of the enoyl-ACP to form the elongated saturated acyl-ACP (enoyl-ACP reductase). β-ketoacyl-ACP synthase I, catalyzes elongation up to palmitoyl-ACP (C16:0), whereas β-ketoacyl-ACP synthase II catalyzes the final elongation to stearoyl-ACP (C18:0). The longest chain fatty acids produced by the FAS are typically 18 carbons long. A further fatty acid biochemical step occurring in the plastid is the desaturation of stearoyl-ACP (C18:0) to form oleoyl-ACP (C18:1) in a reaction catalyzed by a Δ-9 desaturase, also often referred to as a "stearoyl-ACP desaturase" because of its high activity toward stearate the 18 carbon acyl-ACP.

Carbon-chain elongation in the plastids can be terminated by transfer of the acyl group to glycerol 3-phosphate, with the resulting glycerolipid retained in the plastidial, "prokaryotic", lipid biosynthesis pathway. Alternatively, specific thioesterases can intercept the prokaryotic pathway by hydrolyzing the newly produced acyl-ACPs into free fatty acids and ACP.

Subsequently, the free fatty acids are converted to fatty acyl-CoA's in the plastid envelope and exported to the cytoplasm. There, they are incorporated into the "eukaryotic" lipid biosynthesis pathway in the endoplasmic reticulum which is responsible for the formation of phospholipids, triglycerides and other neutral lipids. Following transport of fatty acyl CoA's to the endoplasmic reticulum, subsequent sequential steps for triglyceride production can occur. For example, polyunsaturated fatty acyl groups such as linoleoyl and a-linolenoyl, are produced as the result of sequential desaturation of oleoyl acyl groups by the action of membrane-bound enzymes. Triglycerides are formed by action of the 1-, 2-, and 3-acyl-ACP transferase enzymes glycerol-3-phosphate acyltransferase, lysophosphatidic acid acyltransferase and diacylglycerol acyltransferase. The fatty acid composition of a plant cell is a reflection of the free fatty acid pool and the fatty acids (fatty acyl groups) incorporated into triglycerides as a result of the acyltransferase activities.

The properties of a given triglyceride will depend upon the various combinations of fatty acyl groups in the different positions in the triglyceride molecule. For example, if the fatty acyl groups are mostly saturated fatty acids, then the triglyceride will be solid at room temperature. In general, however, vegetable oils tend to be mixtures of different triglycerides. The triglyceride oil properties are therefore a result of the combination of triglycerides which make up the oil, which are in turn influenced by their respective fatty acyl compositions.

Plant acyl-acyl carrier protein (ACP) thioesterases are of biochemical interest because of their roles in fatty acid synthesis and their utilities in bioengineering of plant oil seeds. A medium-chain acyl-ACP thioesterase from California bay tree, *Umbellularia californica*, has been isolated (Davies et al. (1991) *Arch. Biochem. Biophys.* 290:37–45), and its cDNA cloned and expressed in *E. coli* (Voelker et al. (1994) *J. Bacterial.* 176:7320–7327) and seeds of *Arabidopsis thaliana* and *Brassica napus* (Voelker et al. (1992) *Science* 257:72–74). In both cases, large amounts of laurate (12:0) and small amounts of myristate (14:0) were accumulated. These results demonstrated the role of the TE in determining chain-length during de novo fatty acid biosynthesis in plants and the utility of these enzymes for modifying seed oil compositions in higher plants.

Recently, a number of cDNA encoding different plant acyl-ACP thioesterases have been cloned (Knutzon et al. (1992) *Plant Physiol.* 100:1751–1758; Voelker, et al. (1992) supra; Dormann et al. (1993) *Planta* 189:425–432; Dormann et al. (1994) *Biochim. Biophys. Acta* 1212:134–136; Jones et al. (1995) *The Plant Cell* 7:359–371). Sequence analyses of these thioesterases show high homology, implying similarity in structure and function. Some of these thioesterase cDNAs have been expressed in *E.coli*, and their substrate specificities determined by in vitro assays. The fact that these enzymes share significant sequence homology, yet show different substrate specificities, indicates that subtle changes of amino acids may be sufficient to change substrate selectivity.

Little information is available on structural and functional divergence amongst these plant thioesterases, and the tertiary structure of any plant thioesterase has yet to be determined. Protein engineering may prove to be a powerful tool for understanding the mechanism of thioesterase substrate recognition and catalysis, and thus lead to the rational design of new enzymes with desirable substrate specificities. Such new enzymes would find use in plant bioengineering to provide various modifications of fatty acyl compositions, particularly with respect to production of vegetable oils having significant proportions of desired fatty acyl groups, including medium-chain fatty acyl groups (C8 to C14) and longer chain fatty acyl groups (C16 or C18). In addition, it is desirable to control the relative proportions of various fatty acyl groups that are present in the seed storage oil to provide a variety of oils for a wide range of applications.

Literature

The strategy of using chimeric gene products has been applied to study the structure and function of phosphotransferases in yeast (Hjelmstad et al. (1994) *J. Biol. Chem.* 269: 20995–21002) and restriction endonucleases of Flavobacterium Kim et al. (1994) *Proc. Natl. Acad. Sci. USA.* 91:883–887).

Recently the structure of a myristoyl-ACP thioesterase from Vibrio harveyi has been determined (Lawson et al. (1994) *Biochemistry* 33:9382–9388). This thioesterase, like other bacterial or mammalian thioesterases, shares no sequence homology with plant thioesterases (Voelker et al. (1992) supra).

DESCRIPTION OF THE FIGURES

FIGS. 1A–1C. An amino acid sequence alignment of representative Class I (FatA) and Class II (FatB) thioesterases is provided. UcFatB1 (SEQ ID NO: 1) is a California bay C12 thioesterase. CcFatB1 (SEQ ID NO:2) is a camphor C14 thioesterase. CpFatB1 (SEQ ID NO:3) is a *Cuphea palustris* C8 and C10 thioesterase. CpFatB1 (SEQ ID NO:4) is a *Cuphea palustris* C14 thioesterase. GarmFatA1 (SEQ ID NO:5) is a mangosteen 18:1 thioesterase which also has considerable activity on C18:0 acyl-ACP substrates. BrFatA1 (SEQ ID NO:6) is an 18:1 thioesterase from *Brassica rapa* (aka *Brassica campestris*). Amino acid sequences which are identical in all of the represented thioesterases are indicated by bold shading.

FIGS. 3A–C. Nucleic acid and translated amino acid sequence (SEQ ID NO:24) of a PCR fragment containing the encoding region for the mature protein portion of a camphor Class II acyl-ACP (SEQ ID NO:7) thioesterase is provided.

FIGS. 4A–D. Nucleic acid and translated amino acid sequence of a mangosteen Class I acyl-ACP thioesterase (SEQ ID NO: 8and SEQ ID NO:5, respectively) clone (GarmFatA1) is provided. GarmFatA1 demonstrates primary thioesterase activity on 18:1 acyl-ACP substrate, but also demonstrates considerable activity on 18:0 substrate (approximately 10–20% of 18:1 activity).

FIGS. 5A–D. Nucleic acid and translated amino acid sequence (SEQ ID NO:25) of a mangosteen Class I acyl-ACP thioesterase clone, GarmFatA2, is provided. GarmFatA2 has thioesterase activity primarily on 18:1 acyl-ACP substrate, and equally low activity on 16:0 and 18:0 substrates.

FIGS. 6A–E. Nucleic acid and translated amino acid sequence of a *Cuphea palustris* Class II acyl-ACP thioesterase (SEQ ID NO:10 and SEQ ID NO:3, respectively) clone (CpFatB1) having preferential activity on C8 and C10 acyl-ACP substrates is provided.

FIGS. 7A–D. Nucleic acid and translated amino acid sequence of a *Cuphea palustris* Class II acyl-ACP thioesterase (SEQ ID NO:11 and SEQ ID NO:4, respectively) clone (CpFatB2) having preferential activity on C14 acyl-ACP substrates is provided.

FIG. 11. Substrate specificities of the bay/camphor chimeric enzymes and two bay mutant thioesterases are provided (dark shaded columns). Control (*E. coli* transformed with vector alone) background activities are indicated by the light hatched columns. (A) Ch-1 (B) Ch-2 (C) bay mutant M197R/R199H, and (D) bay mutant M197R/R199H/T231K.

FIG. 13. An amino acid sequence comparison of *B. rapa* BrFatA1 (C18:1) and *Garcinia mangifera* GarmFatA1 (C18:1/C18:0) acyl-ACP thioesterases is provided. Amino acid residues which differ between the thioesterases are indicated by bold shading.

SUMMARY OF THE INVENTION

By this invention, methods of producing engineered plant acyl-ACP thioesterases are provided, wherein said engineered plant acyl-ACP thioesterases demonstrate altered substrate specificity with respect to the acyl-ACP substrates hydrolyzed by the plant thioesterases as compared to the native acyl-ACP thioesterase. Such methods comprise the steps of (1) modifying a gene sequence encoding a plant thioesterase protein targeted for modification to produce one or more modified thioesterase gene sequences, wherein the modified sequences encode engineered acyl-ACP thioesterases having substitutions, insertions or deletions of one or more amino acid residues in the mature portion of the target plant thioesterase, (2) expressing the modified encoding sequences in a host cell, whereby engineered plant thioesterases are produced and, (3) assaying the engineered plant thioesterases to detect those having desirable alterations in substrate specificity.

Figure 1A:
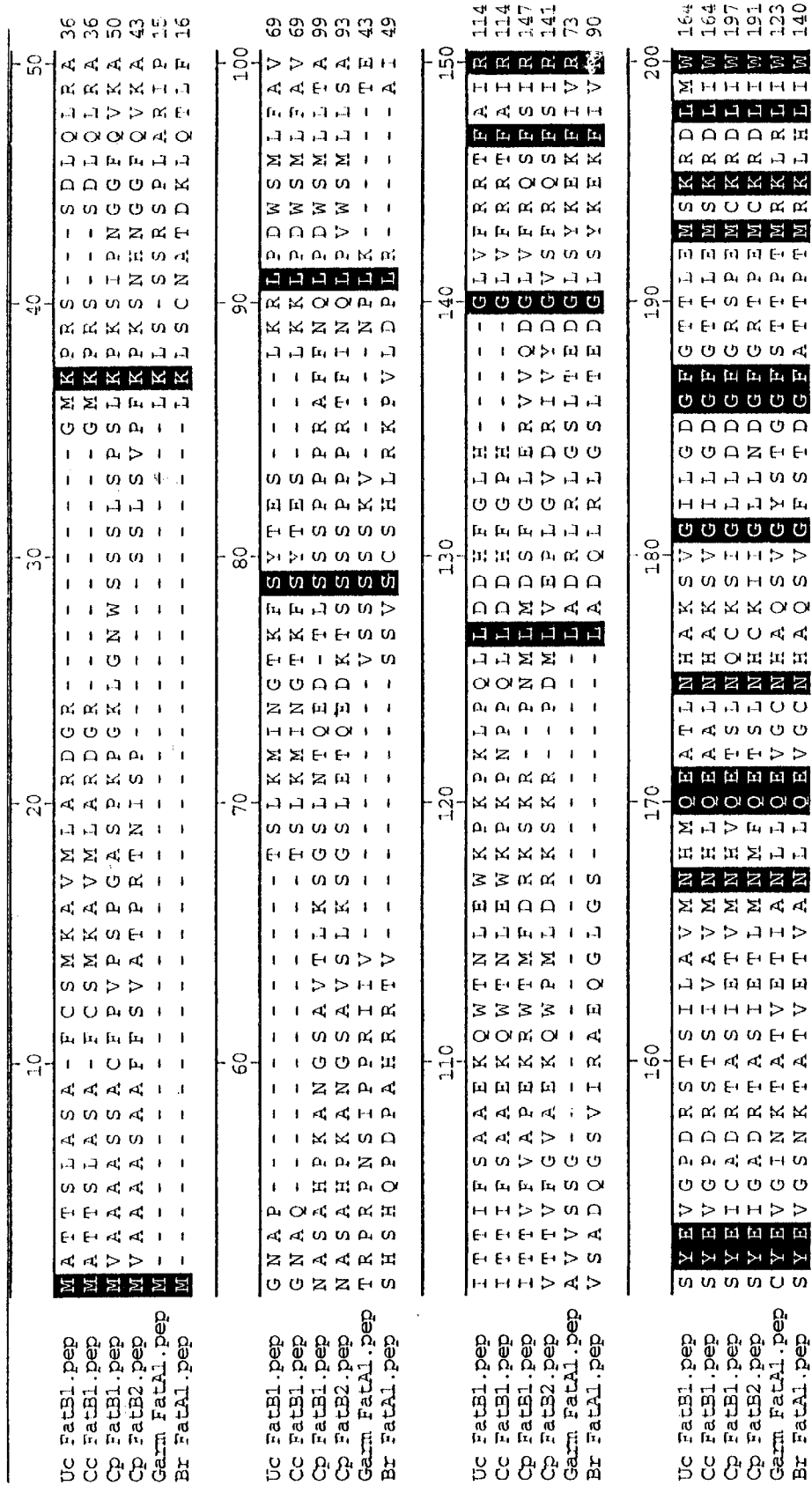
Figure 1B:
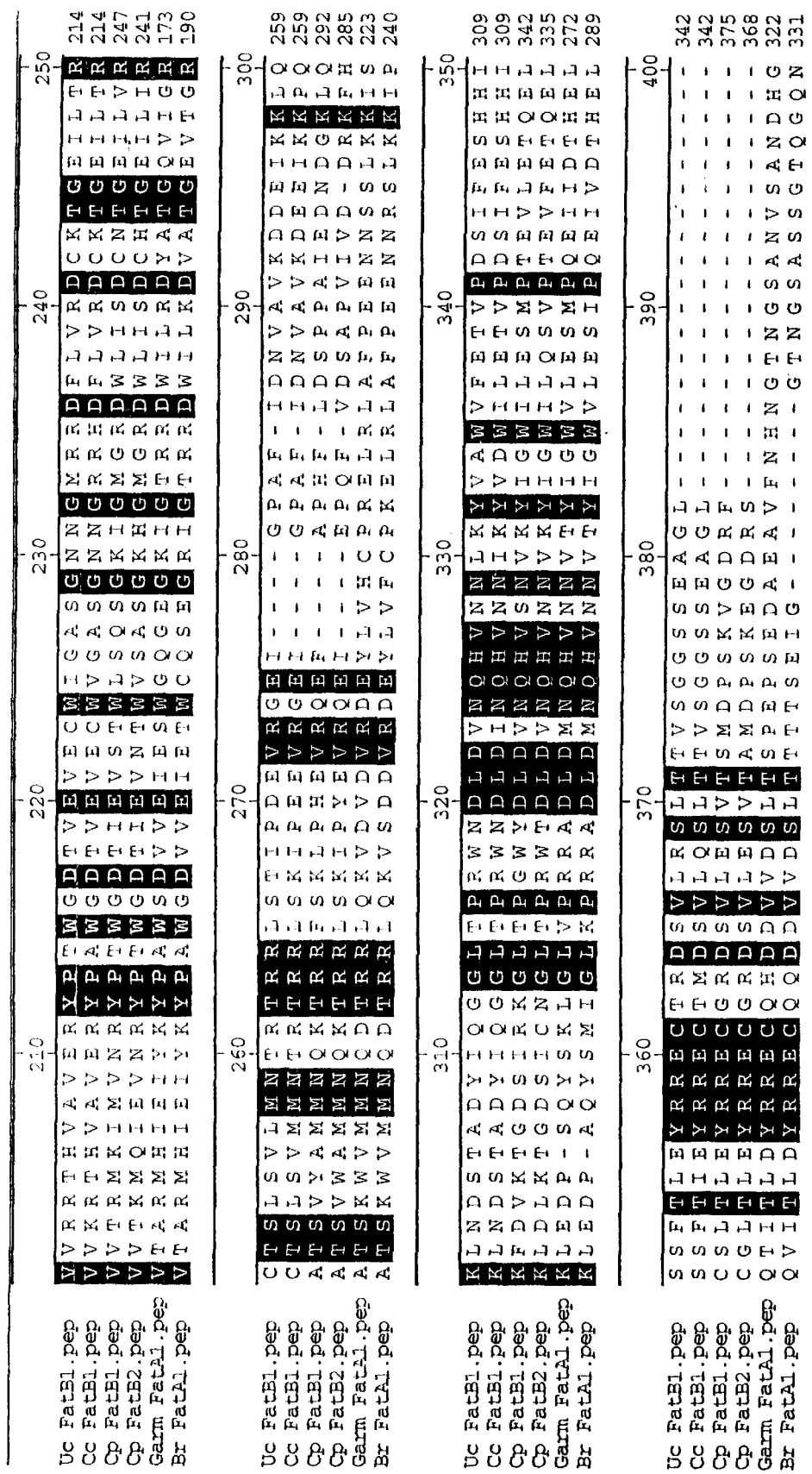
Figure 1C:
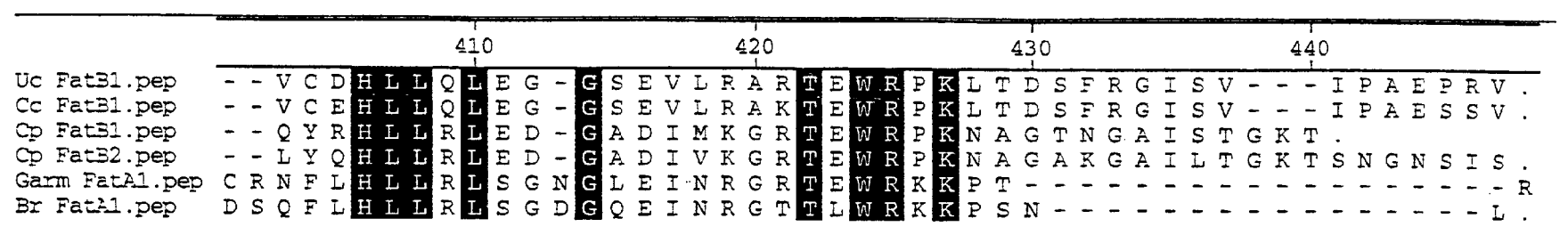

Of particular interest for amino acid alterations is the C-terminal two thirds portion of plant thioesterase, and more particularly, the region corresponding to amino acids 229 to 285 (consensus numbering above sequences) of plant thioesterase sequences as represented in the sequence alignment of FIG. 1. Additionally, the region of from amino acid 285-312 is of interest for modification of thioesterase substrate specificity towards shorter chain fatty acids such as C8 and C10.

Useful information regarding potential modification sites in a targeted thioesterase may be obtained by comparison of related plant acyl-ACP thioesterase amino acid sequences, wherein the compared thioesterases demonstrate different hydrolysis activities. Comparisons of plant thioesterase amino acid sequences having at least 75% sequence identity in the mature protein region are particularly useful in this regard. In this manner, amino acid residues or peptide domains which are different in the related thioesterases may be selected for mutagenesis.

Other methods for selecting amino acids or peptide domains for modification include analysis of thioesterase protein sequences for predicted effects of substitutions, insertions or deletions on flexibility and/or secondary structure of the target thioesterase.

In addition, useful thioesterase gene mutations may be discovered by random mutation of plant acyl-ACP thioesterase encoding sequences, followed by analysis of thioesterase activity or fatty acid composition to detect alterations in substrate specificity.

To produce an engineered thioesterase, a DNA sequence encoding the thioesterase may be altered by domain swapping or mutagenesis, either random or site-directed, to introduce amino acid substitutions, insertions or deletions. The DNA sequences may then be expressed in host cells for production of engineered thioesterases and for analysis of resulting fatty acid compositions. Engineered thioesterases produced in this manner are also assayed to determine effects of the amino acid sequence modifications on the substrate specificity of the thioesterase. In this manner, novel thioesterases may be discovered which demonstrate a variety of profiles with respect to the carbon chain lengths of the acyl-ACP substrates which may be hydrolyzed or with respect to the relative activity of the thioesterase on different carbon chain length acyl-ACP substrates.

Thus, DNA sequences and constructs for expression of engineered thioesterases, as well as the novel thioesterases produced therefrom are also considered within the scope of the invention described herein. Such DNA sequences may be used for expression of the engineered thioesterases in host cells for the modification of fatty acid composition. Of particular interest in the instant invention are DNA constructs for expression of engineered thioesterases in plant cells, especially in plant seed cells of oilseed crop plants. As the result of expression of such constructs, plant triglyceride oil may be produced, wherein the composition of the oil reflects the altered substrate specificity of the engineered thioesterases. Thus, plant cells, seeds and plants comprising the constructs provided herein are all encompassed by the instant invention, as well as novel plant oils that may be harvested from the plant seeds.

For example, a C12 preferring plant acyl-ACP thioesterase described herein may be altered to obtain a plant thioesterase having approximately equal activity on C14 and C12 substrates. Further modification of the C12 enzyme yields a thioesterase having greater activity on C14 as compared to C12 substrates.

Also provided in the instant invention are novel plant acyl-ACP thioesterase sequences from *Cuphea palustris* and mangosteen (*Garcinia mangifera*). The *C. palustris* sequence, CpFatB1, demonstrates substrate specificity towards C8 and C10 fatty acyl-ACPs with higher activity on C8. A mangosteen thioesterase gene, GarmFatA1, demonstrates primary activity on 18:1-ACP substrates, but also demonstrates substantial activity on 18:0-ACP. Importantly, this clone does not demonstrate specificity for 16:0 substrates. Methods of modifying the specificity of these novel C8/C10 and C18:1/C18:0 plant thioesterases are also provided in the instant invention. In particular, mutations which increase the 18:0/18:1 activity ratio of the mangosteen clone are provided.

DETAILED DESCRIPTION OF THE INVENTION

By this invention methods to produce engineered plant thioesterases having altered substrate specificity are provided. An engineered plant thioesterase of this invention may include any sequence of amino acids, such as a protein, polypeptide or peptide fragment obtainable from a plant source which demonstrates the ability to catalyze the production of free fatty acid(s) from fatty acyl-ACP substrates under plant enzyme reactive conditions. By "enzyme reactive conditions" is meant that any necessary conditions are available in an environment (i.e., such factors as temperature, pH, lack of inhibiting substances) which will permit the enzyme to function.

Engineered plant thioesterases may be prepared by random or specific mutagenesis of a thioesterase encoding sequence to provide for one or more amino acid substitutions in the translated amino acid sequence. Alternatively, an engineered plant thioesterase may be prepared by domain swapping between related plant thioesterases, wherein extensive regions of the native thioesterase encoding sequence are replaced with the corresponding region from a different plant thioesterase.

Altered substrate specificities of an engineered thioesterase may be reflected by the presence of hydrolysis activity on an acyl-ACP substrate of a particular chain length which is not hydrolysed by the native thioesterase enzyme. The newly recognized acyl-ACP substrate may differ from native substrates of the enzyme in various ways, such as by having a shorter or longer carbon chain length (usually reflected by the addition or deletion of one or more 2-carbon units), by having a greater or lesser degree of saturation, or by the presence of a methyl group, such as in certain fatty acids which are not commonly present in plant cells, i.e. iso- and anti-iso- fatty acids. Alternatively, altered substrate specificity may be reflected by a modification of the relative hydrolysis activities on two or more acyl-ACP substrates of differing chain length and/or degree of saturation.

DNA and amino acid sequence information for more than thirty plant acyl-ACP thioesterases is now available, and these sequences may be used in the methods of the instant invention to identify desirable regions for modification to produce sequences for expression of engineered thioesterases. Plant thioesterases can be classified into two classes by sequence homology. All of these plant thioesterases contain a transit peptide, of 60 to 80 amino acids in length, for plastid targeting. The transit peptides bear little homology between species while the mature protein regions (minus transit peptide) show significant amino acid sequence identity.

The first class, Class I (or FatA) includes long chain acyl-ACP thioesterases having activity primarily on 18:1-ACP. 18:1-ACP is the immediate precursor of most fatty acids found in phospholipids and tyiglycerides synthesized by the eukaryotic pathway. This class of thioesterase has been found in essentially all plant sources examined to date, and is suggested to be an essential "housekeeping" enzyme (Jones et al. (supra) required for membrane biosynthesis. Examples of Class I thioesterases from safflower, *Cuphea hookeriana* and *Brassica rapa* (*campestris*), which have activity primarily on 18:1-ACP substrate, have been described (WO 92/20236 and WO 94/10288). Other 18:1 thioesterases have been reported in *Arabidopsis thaliana* (Dormann et al. (1995) *Arch. Biochem. Biophys.* 316:612–618), *Brassica napus* (Loader et al. (1993) *Plant Mol. Biol.* 23:769–778) and coriander (Dormann et al. (1994) *Biochem. Biophys. Acta* 1212:134–136). A similar 18:1-ACP specific Class I thioesterase (GarmFatA2) has been discovered in developing embryos from mangosteen (*Garcinia mangifera*), and is described herein. A Class I thioesterase from soybean (WO 92/11373) was reported to provide 10- and 96-fold increases in 16:0-ACP and 18:1-ACP activity upon expression in *E. coli*, and a smaller (3–4 fold) increase in 18:0-ACP activity. The mature protein regions of Class I plant thioesterases are highly homologous, demonstrating greater than 80% sequence identity.

In addition, another mangosteen Class I thioesterase (GarmFatA1), also described herein, has been discovered which demonstrates thioesterase activity primarily on 18:1-ACP substrates (100-fold increase upon expression in *E. coli*), but also demonstrates selective activity on 18:0-ACP versus 16:0-ACP. Additionally, the 18:0 activity of GarmFatA1 is approximately 25% of the 18:1 activity, whereas in most Class I thioesterases analyzed to date, the 18:1 activity is highly predominant, with activity on 16:0 and 18:0 substrates detectable at less than 5% of the 18:1 activity levels. Also, most plant Class I thioesterases demonstrate approximately equal activity on 16:0 and 18:0 substrates, and thus do not exhibit the preferential activity on 18:0 discovered with the mangosteen GarmFatA1 thioesterase. The novel mangosteen wild-type GarmFatA1 clone will thus be useful for production of the 18:1/18:0 thioesterase in host cells, and particularly for expression in plant seed cells for modification of TAG fatty acid composition to provide increased levels of C18:0 fatty acyl groups. In particular, the mangosteen GarmFatA1 clone will be useful in plant genetic engineering application in conjunction with plants containing elevated levels of C18:0 (stearate) fatty acids. Such plants have been obtained by antisense gene regulation of stearoyl-ACP desaturase in Brassica seeds as described by Knutzon et al. (*Proc. Nat. Acad. Sci.* (1992) 89:2624–2628), and may also be obtained by co-suppression using sense expression constructs of the stearoyl-ACP desaturase gene, or by conventional mutation and plant breeding programs.

A second class of plant thioesterases, Class II (or FatB) thioesterases, include enzymes that utilize fatty acids with shorter chain-lengths, from C8:0 to C14:0 (medium chain fatty acids) as well as C16:0. Class II thioesterases preferably catalyze the hydrolysis of substrates containing saturated fatty acids. Class II (or FatB) thioesterases have been isolated from California Bay, elm, *Cuphea hookeriana, Cuphea palustris, Cuphea lanceolata*, nutmeg, *Arabidopsis thaliana*, mango, leek and camphor. The mature protein regions of Class II plant thioesterases are also highly homologous, demonstrating 70–80% sequence identity.

One of the characteristics of Class II thioesterases is the presence of a relatively hydrophobic region of approximately 40 amino acids in the N-terminal region of the mature proteins. This hydrophobic region is not found in 18:1-ACP thioesterases, and has no apparent effect on the enzyme activity. Recombinant expression of a bay Class II thioesterase with or without this region showed identical activity profiles in vitro (Jones et al. (supra)).

As demonstrated more fully in the following examples, the acyl-ACP substrate specificity of plant thioesterases may be modified by various amino acid changes to the protein sequence, such as amino acid substitutions, insertions or deletions in the mature protein portion of the plant thioesterases. Modified substrate specificity can be detected by expression of the engineered plant thioesterases in *E. coli* and assaying to detect enzyme activity.

Modified substrate specificity may be indicated by a shift in acyl-ACP substrate preference such that the engineered thioesterase is newly capable of hydrolysing a substrate not recognized by the native thioesterase. The newly recognized substrate may vary from substrates of the native enzyme by carbon chain length and/or degree of saturation of the fatty acyl portion of the substrate. Alternatively, modified substrate specificity may be reflected by a shift in the relative thioesterase activity on two or more substrates of the native thioesterase such that an engineered thioesterase exhibits a different order of preference for the acyl-ACP substrates.

For example, a plant thioesterase having primary hydrolysis activity on C12 substrate and some minor activity on C14 substrate may be modified to produce an engineered thioesterase which exhibits increased activity on C14, for example so that the engineered thioesterase has approximately equal activity on C12 and C14 substrates. Similarly, such plant C12 thioesterases may be further modified to produce an engineered thioesterase having primary activity on C14 substrates and little or no activity on C12 substrates. Alternatively, a plant thioesterase may be modified so as to alter the relative activity towards a substrate having higher or lesser degree of saturation. For example, a Class I (18:1) thioesterase may be modified to increase the relative activity on C18:0 substrates as compared to activity on other substrates of the enzyme, such as C18:1 and C16:0. Examples of these types of thioesterase modifications are provided in the following examples. Further modification of plant thioesterases are also desirable and may be obtained using the methods and sequences provided herein. For example, plant thioesterases may be modified to shift the enzymatic activity towards hydrolysis of shorter chain fatty acids, such as C8 and C10. Comparison of closely related thioesterase sequences, such as the *C. palustris* C8/10, the *C. palustris* C14 and the *C. hookeriana* C8/10 thioesterase sequences provided herein may be used to identify potential target amino acid residues for alteration of thioesterase specificity.

Additionally, the novel *C. palustris* C8/10 wild-type thioesterase clone provided herein, CpFatB1, will find use for expression of the thioesterase in host cells, particularly for expression in plant seed cells for modification of fatty acid composition. In this manner, plant seed oils having increased proportions of C8 and C10 fatty acids may be obtained. In Brassica oilseeds, the C8 and C10 fatty acids will be present primarily at the sn-1 and sn-3 positions of the TAG and an unsaturated fatty acid, such as 18:1, 18:2 or 18:3 will be present at the sn-2 position.

The TAG and fatty acids produced in this manner may be extracted from the seed oils, purified and further modified according the specific application. Applications for shorter chain fatty acids, particularly C8 and C10 include industrial uses such as for jet engine lubricants or, in the form of methyl esters or TAG, for "biodiesel" fuels. Polyol ester of C8 and C10 fatty acids find application in engine oils, industrial gear box oils, refrigerator or transformer fluids, and compressor and chain oils. Contemplated industrial uses for C8 and C10 fatty acids or triglycerides include any vegetable oil applications where low melting point and high stability are desirable. C8 and C10 fatty acids also find use in food and nutritional applications due to the rapid absorption of TAG having short chain acyl groups, and the low caloric content of C8 and C10 fatty acids. Structured lipids having the C8 and/or C10 at the sn-1 and sn-3 positions will find application in the delivery of the fatty acid at the sn-2 position due to the ease of absorption of such molecules, and find particular nutritional use in a variety of nutritionally impaired target groups. C8 and C10 fatty acids also find use in various cosmetic applications, and as co-solvents for flavors and essential oils in food applications.

For applications where C8 and/or C10 fatty acid molecules are desired in all three TAG positions, plants producing C8 and C10 fatty acids, such as oilseed Brassica plants, may also be altered to express a medium-chain preferring LPAAT to increase the proportion of C8/C10 fatty acids in the sn-2 position. A medium-chain LPAAT from coconut is described in co-pending application Ser. No. 08/327,451 filed on Oct. 21, 1994 and related PCT application PCT/US95/03997 filed on Mar. 31, 1995. Further modifications may also be provided by combination of the C8/C10 fatty acid plants with additional gene traits. For example plants Brassica plants producing oil in which all three positions of a percentage of the TAG contain C8 or C10 fatty acids may be crossed with high erucic acid Brassica plants. In this manner, oil containing erucic acid (C22:1) in the sn-1 or sn-3 position and C8 and/or C10 in the remaining TAG positions may be obtained. Hydrogenation of such a composition will yield TAG molecules having C8 and or C10 saturated fatty acids in two positions, and C22:0 (caprenin) in the sn-1 or sn-2 position. Such TAG molecules find particular application as low calorie oils for food uses.

To investigate the possibility of altering substrate specificity of plant thioesterase enzymes, two highly related Class II thioesterases were studied, a C12 preferring acyl-ACP thioesterase from California bay (*Umbellularia californica*) and a C14 preferring acyl-ACP thioesterase from camphor (*Cinnamomum camphora*). These enzymes demonstrate 90% amino acid sequence identity in the mature protein region yet have different substrate specificities. Constructs for expression of chimeric mature thioesterases were prepared which encoded chimeric thioesterase enzymes containing the N-terminal mature protein region of either the camphor or bay thioesterase and the C-terminal portion of the other thioesterase. The N-terminal thioesterase portion as encoded in these constructs contains approximately one third of the mature thioesterase protein, and the C-terminal portion contains the remaining two thirds of the mature thioesterase region. As described in more detail in the following examples, we have discovered that the C-terminal two thirds portion of these plant thioesterases is critical in determining the substrate specificity. The chimeric enzyme containing the C-terminal portion of the camphor thioesterase (Ch-1) demonstrates the same activity profile as native camphor thioesterase (specific for 14:0), and the chimeric protein with the bay thioesterase C-terminus (Ch-2) demonstrates the same activity profile as native bay thioesterase (12:0 specific).

Figure 8:
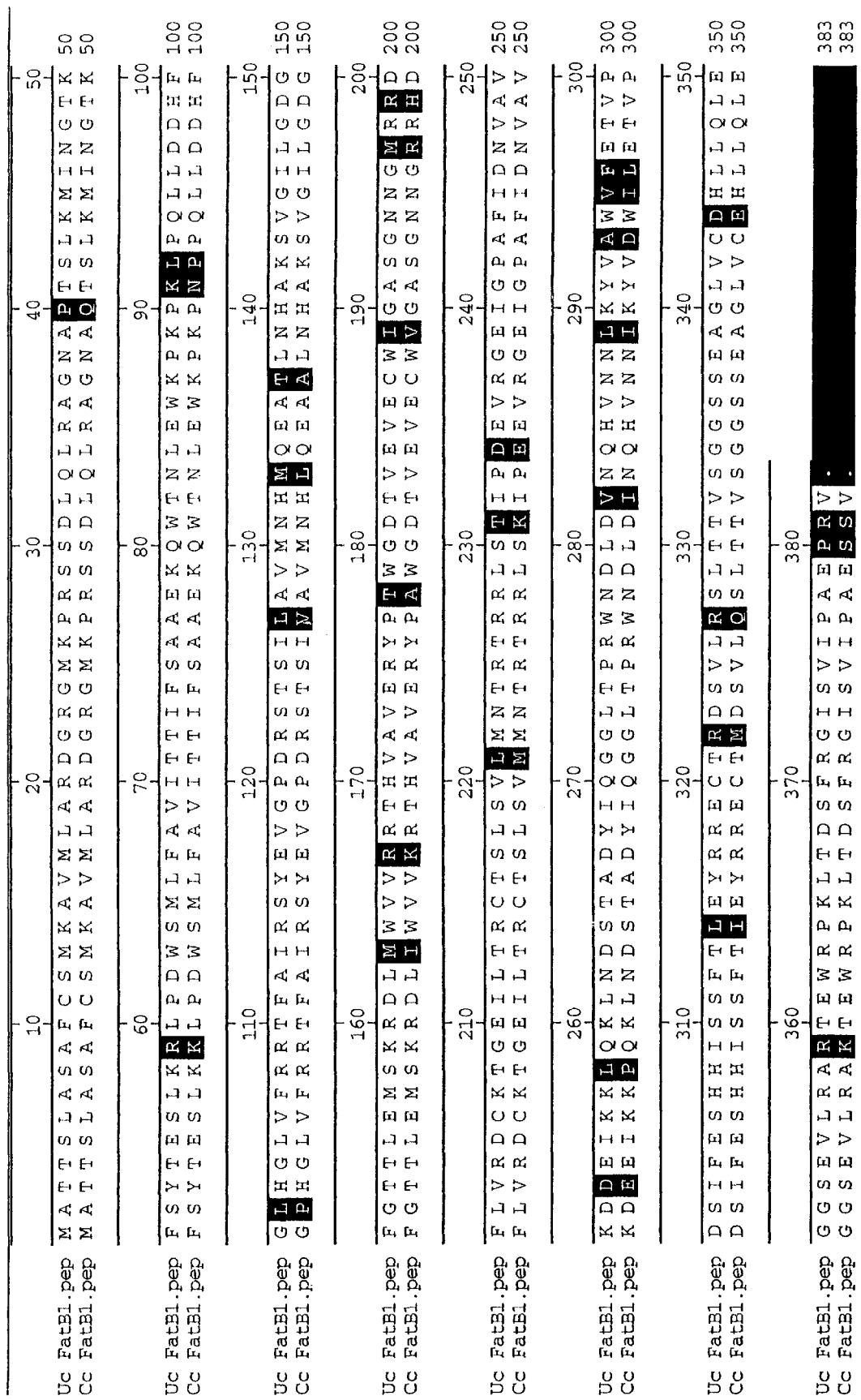
FIG. 8. An amino acid sequence comparison of bay (C12) and camphor (C14) acyl-ACP thioesterases is provided. Amino acid residues which differ between the thioesterases are indicated by bold shading.

Further analysis of the C-terminal two thirds portion of the bay C12 preferring acyl-ACP thioesterase was conducted to further identify the amino acid regions involved in substrate specificity. By examining a sequence alignment of the bay and camphor thioesterases, the least conservative amino acid substitutions between the two thioesterases in the C-terminal two thirds portion of the proteins were identified. Non-conservative amino acid substitutions include those in which the substituted amino acid has a different charge than the native amino acid residue. Amino acids considered as having positively charged side chains at pH 7 are lysine and arginine. Histidine can also have a positively charged side chain under conditions of acidic pH. Amino acids considered as having negatively charged side chains at pH 7 are aspartate and glutamate. Non-conservative amino acid substitutions may also be indicated where the size of the substituted amino acid differs considerably from the size of the amino acid normally located at that position. Examples of non-conserved amino acid differences between the bay and camphor thioesterases are M197→R (Bay TE→Camphor TE), R199→H, T231→K, A293→D, R327→Q, P380→S,and R381→S (amino acid sequence numbering for bay and camphor thioesterases is shown in FIG. 8).

Secondary structure predictions may be used to identify amino acid substitutions likely to have affects on the secondary structure of the thioesterase protein. For example, according to secondary structure predictions using methods of Chou and Fasman, the tripeptide M-R-R amino acids 197–199 of bay and the corresponding tripeptide R-R-H of camphor are located behind a β-sheet and a turn anchored by two highly conserved glycines (G193 and G196). This region of plant thioesterases is highly conserved, and the β-sheet and a turn structure is also predicted in other plant thioesterases.

As described in the following examples, when the bay M-R-R tripeptide is changed to R-R-H, mimicking the sequence in camphor thioesterase, the activity of the mutant towards 12:0, but not 14:0, is reduced about 7 fold compared to the wild type. This results in an engineered thioesterase which has approximately equal specific activity with respect to the 12:0 and 14:0 substrates.

An additional modification of the engineered bay M197R/R199H thioesterase which converts the threonine residue at amino acid 231 to a lysine (T231K) alters the substrate specificity such that the engineered thioesterase M197R/R199H/T231K is highly 14:0-ACP specific. Interestingly, the mutation T231K alone does not affect the bay thioesterase activity. The non-additive, combinatorial effect of the T231K substitution on M197R/R199H engineered thioesterase suggests that the altered amino acid sites are folded close to each other (Sandberg, et al. (1993) *Proc. Natl. Acad. Sci.* 90: 8367–8371).

As described in the following Examples, amino acid substitutions near the active site (YRREC, amino acids 357–361 in FIG. 1 consensus numbering) of the plant acyl-ACP thioesterases may result in large reductions in thioesterase activity. Modification of bay thioesterase to produce R327Q results in no modification of the specificity of the bay enzyme for C12, but results in a 100-fold decrease in the bay thioesterase activity. The decreased activity of R327Q is likely due to the fact that this amino acid position is located very close to the active site cysteine, C320 of the bay thioesterase sequence in FIG. 8.

Expression of engineered thioesterases having altered substrate specificities in host cells and analysis of resulting fatty acid compositions demonstrates that the altered substrate specificities of the engineered thioesterases are reflected in the fatty acid composition profiles of the host cells. This is significant because enzyme activity in vivo might have involved sequential interactions or parameters such as lifetime and folding/unfolding rates which would not be reflected in in vitro activity assays. The major lipid components of *E.coli* membranes are phosphatidylethanolamine and phosphatidylglycerol, which contain predominantly long-chain fatty acyl moieties. Recombinant expression of native bay thioesterase cDNA in fadD cells redirects the bacterial type II fatty acid synthase system from long-chain to medium-chain production, and similar results are obtained upon expression of native bay thioesterase in seeds of transgenic plants (Voelker et al. (1994) supra; Voelker et al. (1992) supra). Thus, *E. coli* in vivo data may be used to predict the effects of expression of engineered thioesterases in transgenic plants.

With native bay thioesterase, *E. coli* fadD cells produce large amounts of 12:0 free fatty acid and small amounts of 14:0 (about 5 to 10% of 12:0 levels) Voelker et al. (1994) Table I). However, as demonstrated in the following examples, following two amino acid substitutions (M197R/R199H), expression of an engineered bay thioesterase enzyme results in accumulation of similar amounts of 12:0 and 14:0 fatty acids. Similarly, expression of the engineered bay thioesterase with three amino acid substitutions (M197R/R199H/T231K) completely reverses the 12:0/14:0 ratio of fatty acids produced as compared to results with native bay thioesterase.

Thus, as the result of modifications to the substrate specificity of plant thioesterases, it can be seen that the relative amounts of the fatty acids produced in a cell where various substrates are available for hydrolysis may be altered. Furthermore, molecules which are formed from available free fatty acids, such as plant seed triglycerides, may also be altered as a result of expression of engineered thioesterases having altered substrate specificities.

In addition to known acyl-ACP thioesterases and encoding sequences, such as provided herein, other acyl-ACP thioesterase sequences may be obtained from a variety of plant species, and such thioesterases and encoding sequences will find use in the methods of this invention. As noted above, plant thioesterase encoding sequences are highly conserved, particularly for those thioesterases which are members of the same class of thioesterase, i.e. Class I or Class II. Thus, for isolation of additional thioesterases, a genomic or other appropriate library prepared from a candidate plant source of interest is probed with conserved sequences from one or more Class I or Class II plant thioesterase sequences to identify homologously related clones. Positive clones are analyzed by restriction enzyme digestion and/or sequencing. Probes can also be considerably shorter than the entire sequence. Oligonucleotides may be used, for example, but should be at least about 10, preferably at least about 15, more preferably at least 20 nucleotides in length. When shorter length regions are used for comparison, a higher degree of sequence identity is required than for longer sequences. Shorter probes are often particularly useful for polymerase chain reactions (PCR) (Gould, et al., *PNAS USA* (1989) 86:1934–1938), especially for isolation of plant thioesterases which contain highly conserved sequences. PCR using oligonucleotides to conserved regions of plant thioesterases may also be used to generate homologous probes for library screening.

When longer nucleic acid fragments are employed (>100 bp) as probes, especially when using complete or large cDNA sequences, one can still screen with moderately high stringencies (for example using 50% formamide at 37° C. with minimal washing) in order to obtain signal from the target sample with 20–50% deviation, i.e., homologous sequences. (For additional information regarding screening techniques see Beltz, et al. *Methods in Enzymology* (1983) 100:266–285.).

The nucleic acid or amino acid sequences encoding an engineered plant acyl-ACP thioesterase of this invention may be combined with other non-native, or "heterologous", sequences in a variety of ways. By "heterologous" sequences is meant any sequence which is not naturally found joined to the plant acyl-ACP thioesterase, including, for example, combinations of nucleic acid sequences from the same plant which are not naturally found joined together.

For expression in host cells, sequence encoding an engineered plant thioesterase is combined in a DNA construct having, in the 5' to 3' direction of transcription, a transcription initiation control region capable of promoting transcription and translation in a host cell, the DNA sequence encoding the engineered plant acyl-ACP thioesterase and a transcription and translation termination region.

DNA constructs may or may not contain pre-processing sequences, such as transit peptide sequences. Transit peptide sequences facilitate the delivery of the protein to a given organelle and are cleaved from the amino acid moiety upon entry into the organelle, releasing the "mature" sequence. The use of the precursor plant acyl-ACP thioesterase DNA sequence is preferred in plant cell expression cassettes. Other plastid transit peptide sequences, such as a transit peptide of seed ACP, may also be employed to translocate plant acyl-ACP thioesterases to various organelles of interest.

Thus, engineered plant thioesterase sequences may be used in various constructs, such as for expression of the thioesterase of interest in a host cell for recovery or study of the enzyme in vitro or in vivo. Potential host cells include both prokaryotic and eukaryotic cells. A host cell may be unicellular or found in a multicellular differentiated or undifferentiated organism depending upon the intended use. Cells of this invention may be distinguished by having an engineered plant acyl-ACP thioesterase present therein.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the engineered plant enzyme and is useful for identifying the particular characteristics of such enzymes. Among transcriptional initiation regions which have been described are regions from bacterial and yeast hosts, such as *E. coli, B. subtilis, Saccharomyces cerevisiae*, including genes such as beta-galactosidase, T7 polymerase, tryptophan E and the like.

For the most part, the constructs will involve regulatory regions functional in plants which provide for expression of the engineered plant acyl-ACP thioesterase, and thus will provide for modification of the fatty acid composition in plant cells. The open reading frame, coding for the engineered plant acyl-ACP thioesterase will be joined at its 5' end to a transcription initiation regulatory region such as the wild-type sequence naturally found 5' upstream to the thioesterase structural gene. Numerous other transcription initiation regions are available which provide for a wide variety of constitutive or regulatable, e.g., inducible, transcription of the structural gene functions. Among transcriptional initiation regions used for plants are such regions associated with the structural genes such as for nopaline and mannopine syntheses, or with napin, ACP promoters and the like. The transcription/translation initiation regions corresponding to such structural genes are found immediately 5' upstream to the respective start codons. In embodiments wherein the expression of the engineered thioesterase protein is desired in a plant host, the use of part of the native plant acyl-ACP thioesterase gene is considered. Namely, all or a portion of the 5' upstream noncoding regions (promoter) together with 3' downstream noncoding regions may be employed. If a different promoter is desired, such as a promoter native to the plant host of interest or a modified promoter, i.e., having transcription initiation regions derived from one gene source and translation initiation regions derived from a different gene source (enhanced promoters), such as double 35S CaMV promoters, the sequences may be joined together using standard techniques.

For such applications when 5' upstream non-coding regions are obtained from other genes regulated during seed maturation, those preferentially expressed in plant embryo tissue, such as ACP and napin-derived transcription initiation control regions, are desired. Such "seed-specific promoters" may be obtained and used in accordance with the teachings of U.S. Ser. No. 07/147,781, filed Jan. 25, 1988 (now U.S. Ser. No. 07/550,804, filed Jul. 9, 1990), and U.S. Ser. No. 07/494,722 filed on or about Mar. 16, 1990 having a title "Novel Sequences Preferentially Expressed In Early Seed Development and Methods Related Thereto," which references are hereby incorporated by reference. Transcription initiation regions which are preferentially expressed in seed tissue, i.e., which are undetectable in other plant parts, are considered desirable for fatty acid modifications in order to minimize any disruptive or adverse effects of the gene product.

Regulatory transcript termination regions may be provided in DNA constructs of this invention as well. Transcript termination regions may be provided by the DNA sequence encoding the engineered plant acyl-ACP thioesterase or a convenient transcription termination region derived from a different gene source, for example, the transcript termination region which is naturally associated with the transcript initiation region. Where the transcript termination region is from a different gene source, it will contain at least about 0.5 kb, preferably about 1–3 kb of sequence 3' to the structural gene from which the termination region is derived.

Plant expression or transcription constructs having an engineered plant acyl-ACP thioesterase as the DNA sequence of interest may be employed with a wide variety of plant life, particularly, plant life involved in the production of vegetable oils for edible and industrial uses. Most especially preferred are temperate oilseed crops. Plants of interest include, but are not limited to, grapeseed (Canola and High Erucic Acid varieties), sunflower, safflower, cotton, Cuphea, soybean, peanut, coconut and oil palms, and corn. Depending on the method for introducing the recombinant constructs into the host cell, other DNA sequences may be required. Importantly, this invention is applicable to dicotyledon and monocotyledon species alike and will be readily applicable to new and/or improved transformation and regulation techniques.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. In addition, techniques of microinjection, DNA particle bombardment, electroporation have been developed which allow for the transformation of various monocot and dicot plant species.

In developing the DNA construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

It is noted that the degeneracy of the DNA code provides that some codon substitutions are permissible of DNA sequences without any corresponding modification of the amino acid sequence.

As mentioned above, the manner in which the DNA construct is introduced into the plant host is not critical to this invention. Any method which provides for efficient transformation may be employed. Various methods for plant cell transformation include the use of Ti- or Ri-plasmids, microinjection, electroporation, DNA particle bombardment, liposome fusion, DNA bombardment or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed Agrobacterium host. The armed plasmid can give a mixture of normal plant cells and gall.

In some instances where Agrobacterium is used as the vehicle for transforming plant cells, the expression construct bordered by the T-DNA border(s) will be inserted into a broad host spectrum vector, there being broad host spectrum vectors described in the literature. Commonly used is pRK2 or derivatives thereof. See, for example, Ditta et al., *PNAS USA*, (1980) 77:7347–7351 and EPA 0 120 515, which are incorporated herein by reference. Included with the expression construct and the T-DNA will be one or more markers, which allow for selection of transformed Agrobacterium and transformed plant cells. A number of markers have been developed for use with plant cells, such as resistance to chloramphenicol, the aminoglycoside G418, hygromycin, or the like. The particular marker employed is not essential to this invention, one or another marker being preferred depending on the particular host and the manner of construction.

Once a transgenic plant is obtained which is capable of producing seed having a modified fatty acid composition, traditional plant breeding techniques, including methods of mutagenesis, may be employed to further manipulate the fatty acid composition. Alternatively, additional foreign fatty acid modifying DNA sequence may be introduced via genetic engineering to further manipulate the fatty acid composition. It is noted that the method of transformation is not critical to this invention. However, the use of genetic engineering plant transformation methods, i.e., the power to insert a single desired DNA sequence, is critical. Heretofore, the ability to modify the fatty acid composition of plant oils was limited to the introduction of traits that could be sexually transferred during plant crosses or viable traits generated through mutagenesis. Through the use of genetic engineering techniques which permits the introduction of inter-species genetic information and the means to regulate the tissue-specific expression of endogenous genes, a new method is available for the production of plant seed oils with modified fatty acid compositions. In addition, there is the potential for the development of novel plant seed oils upon application of the tools described herein.

One may choose to provide for the transcription or transcription and translation of one or more other sequences of interest in concert with the expression of an engineered plant acyl-ACP thioesterase in a plant host cell. In particular, the expression of a plant LPAAT protein having activity on medium-chain or very long-chain fatty acids in combination with expression of an engineered plant acyl-ACP thioesterase may be preferred in some applications. See co-pending application U.S. Ser. No. 08/327,451 filed Oct. 21, 1994 for plant LPAAT encoding sequences.

When one wishes to provide a plant transformed for the combined effect of more than one nucleic acid sequence of interest, typically a separate nucleic acid construct will be provided for each. The constructs, as described above contain transcriptional or transcriptional or transcriptional and translational regulatory control regions. One skilled in the art will be able to determine regulatory sequences to provide for a desired timing and tissue specificity appropriate to the final product in accord with the above principles set forth as to the respective expression or anti-sense constructs. When two or more constructs are to be employed, whether they are both related to the same fatty acid modifying sequence or a different fatty acid modifying sequence, it may be desired that different regulatory sequences be employed in each cassette to reduce spontaneous homologous recombination between sequences. The constructs may be introduced into the host cells by the same or different methods, including the introduction of such a trait by crossing transgenic plants via traditional plant breeding methods, so long as the resulting product is a plant having both characteristics integrated into its genome.

The invention now being generally described, it will be more readily understood by reference to the following examples which are included for purposes of illustration only and are not intended to limit the present invention.

EXAMPLES

Example 1

Sequences of Plant Acyl-ACP Thioesterases

A. California Bay (*Umbellularia californica*)

DNA sequence and translated amino acid sequence of California bay Class II thioesterase clone pCGN3822 is provided in FIG. 1 of WO 92/20236. Expression of the mature portion of the bay thioesterase protein in *E. coli* and analysis of thioesterase activity reveals a strong specificity of the bay thioesterase for 12:0-ACP substrate, although some activity towards 14:0-ACP is also observed (Voelker et al. (1994) supra, and FIG. 2A herein). Furthermore, when bay thioesterase is expressed in *E. coli* fadD cells, large amounts of laurate (more than 500-fold above control background) and small amounts of myristate (about 10% of that of laurate) are produced. Production of similar ratios of laurate and myristate are also observed upon expression of the bay thioesterase in seeds of Brassica napus or *Arabidopsis thaliana* (Voelker et al. (1992) supra).

B. Camphor (*Cinnamomum camphora*)

DNA sequence and translated amino acid sequence of a Class II camphor thioesterase encoding region generated by PCR is provided in FIG. 5B of WO 92/20236. Sequence of a DNA fragment obtained by PCR from reverse transcribed cDNA and containing the mature protein region of the camphor clone is provided in FIG. 3 (SEQ ID NO:7 and 24). The sequence begins at the XbaI site located at the beginning of the presumed mature protein encoding region of the camphor thioesterase.

Figure 2:
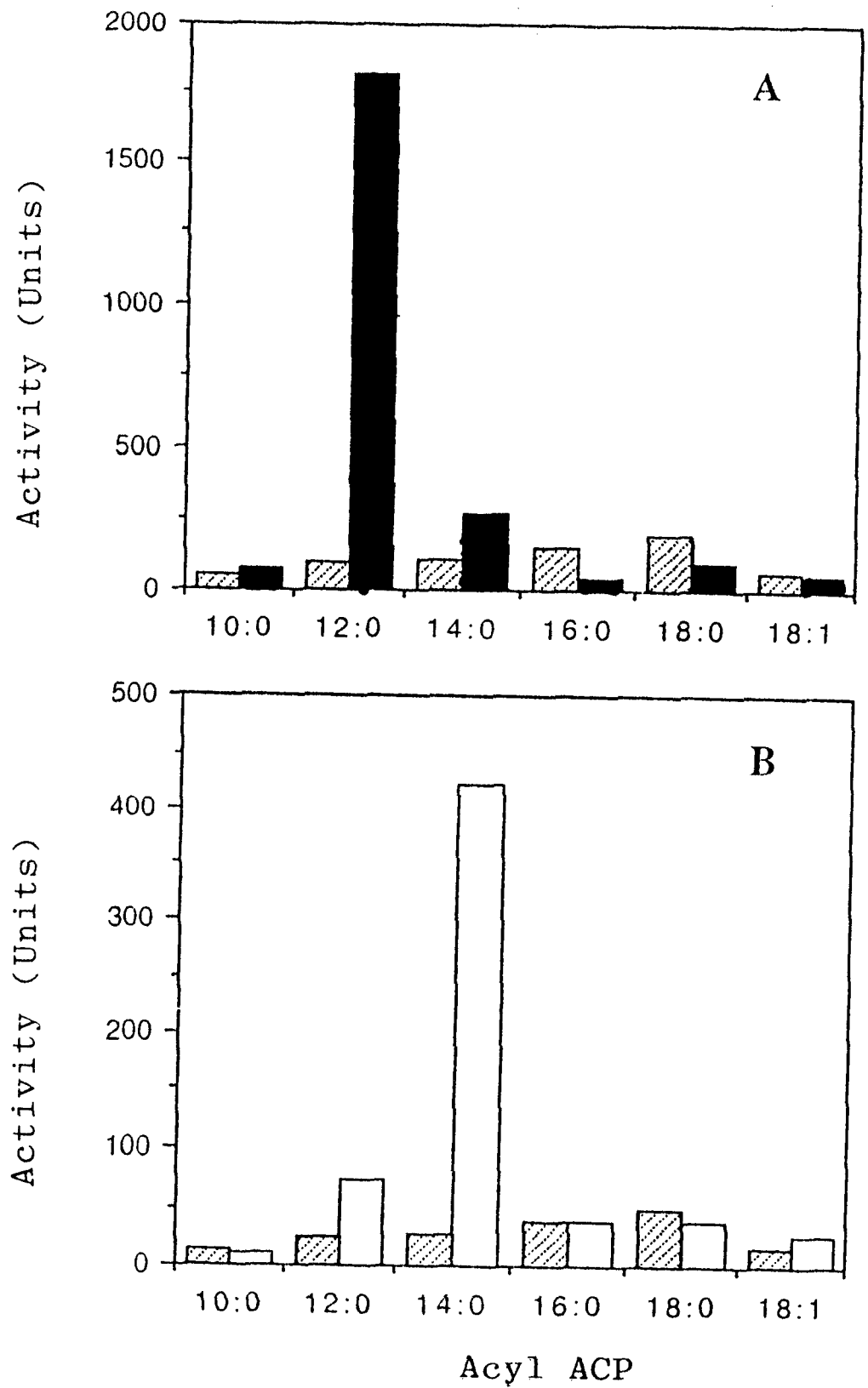
FIG. 2. Results of thioesterase activity assays of wild-type bay (FIG. 2A) and wild-type camphor (FIG. 2B) thioesterases upon expression in *E. coli* is presented.

The camphor PCR fragment described above is cloned into a pAMP vector resulting in pCGN5219. pCGN5219 is digested with XbaI and SalI and the resulting camphor thioesterase fragment is cloned into XbaI and SalI digested pBCSK+ (Stratagene), resulting in pCGN5220. pCGN5220 is used to transform *E. coli* fadD for analysis of acyl-ACP thioesterase activity as described in Pollard et al. (*Arch. Biochem & Biophys.* (1991) 281:306–312). Results of thioesterase activity assays on camphor thioesterase clones using 8:0, 10:0, 12:0, 14:0, 16:0, 18:0 and 18:1 acyl-ACP substrates demonstrate substrate specificity mainly on 14:0 substrates, although a lesser increase in 12:0 hydrolysis activity is also observed (FIG. 2B).

C. Mangosteen (*Garcinia mangifera*)

A cDNA bank is prepared from seeds extracted from mature mangosteen fruit using the methods as described in Stratagene Zap cDNA synthesis kit (Stratagene; La Jolla, Calif.). Oil analysis of the mangosteen tissues used for RNA isolation reveals 18:0 levels of approximately 50%. Oil analysis of seeds from less mature mangosteen fruit reveals 18:0 levels of 20–40%. Total RNA is isolated from the mangosteen seeds by modifying the CTAB (hexadecyltrimethylammoniumbromide) DNA isolation method of Webb and Knapp (*Plant Mol. Biol. Reporter* (1990) 8:180–195). Buffers include:

REC: 50 mM TrisCl pH 9, 0.7M NaCl, 10 mM EDTA pH8, 0.5% CTAB.

REC+: Add B-mercaptoethanol to 1% immediately prior to use.

RECP: 50 mM TrisCl pH9, 10 mM EDTA pH8, and 0.5% CTAB.

RECP+: Add B-mercaptoethanol to 1% immediately prior to use.

For extraction of 1 g of tissue, 10 ml of REC+ and 0.5 g of PVPP (polyvinylpolypyrrolidone) is added to tissue that has been ground in liquid nitrogen and homogenized. The homogenized material is centrifuged for 10 min at 1200 rpm. The supernatant is poured through miracloth onto 3 ml cold chloroform and homogenized again. After centrifugation, 12,000 RPM for 10 min, the upper phase is taken and its volume determined. An equal volume of RECP+ is added and the mixture is allowed to stand for 20 min. at room temperature. The material is centrifuged for 20 min. at 10,000 rpm twice and the supernatant is discarded after each spin. The pellet is dissolved in 0.4 ml of 1M NaCl (DEPC) and extracted with an equal volume of phenol/chloroform. Following ethanol precipitation, the pellet is dissolved in 1 ml of DEPC (diethylpyrocarbonate) water.

Briefly, the cloning method for cDNA synthesis is as follows. First strand cDNA synthesis is according to Stratagene Instruction Manual with some modifications according to Robinson, et al. (*Methods in Molecular and Cellular Biology* (1992) 3:118–127). In particular, approximately 57 µg of LiCl precipitated total RNA was used instead of 5 µg of poly(A)+ RNA and the reaction was incubated at 45° C. rather than 37° C. for 1 hour.

Probes for library screening are prepared by PCR from mangosteen cDNA using oligonucleotides to conserved plant acyl-ACP thioesterase regions. Probe Garm 2 and Garm 106 are prepared using the following oligonucleotides. The nucleotide base codes for the below oligonucleotides are as follows:

| | |
|---|---|
| A = adenine | C = cytosine |
| T = thymine | U = uracil |
| G = guanine | S = guanine or cytosine |
| K = guanine or thymine | W = adenine or thymine |
| M = adenine or cytosine | R = adenine or guanine |
| Y = cytosine or thymine | |
| B = guanine, cytosine or thymine | |
| H = adenine, cytosine or thymine | |
| N = adenine, cytosine, guanine or thymine | |

Garm 2

4874: 5' CUACUACUACUASYNTVNGYNATGAT-GAA 3' (SEQ ID NO:12)

4875: 5' CAUCAUCAUCAURCAYTCNCKNCK-RTANTC 3' (SEQ ID NO:13)

Primer 4874 is a sense primer designed to correspond to possible encoding sequences for conserved peptide V/L/A W/S/Y V/A M M N (SEQ ID NO:20), where the one letter amino acid code is used and a slash between amino acids indicates more than one amino acid is possible for that position. Primer 4875 is an antisense primer designed to correspond to possible encoding sequences for peptide D/E Y R R E C (SEQ ID NO:20).

Garm 106

5424: 5' AUGGAGAUCUCUGAWCRBTAYCCTAM-HTGGGGWGA 3' (SEQ ID NO:14)

5577: 5' ACGCGUACUAGUTTNKKNCKCCAYTC-NGT 3' (SEQ ID NO:15)

Primer 5424 is a sense primer designed to correspond to possible encoding sequences for peptide E/D H/R Y P K/T W G D (SEQ ID NO:22). Primer 5577 is an antisense primer designed to correspond to possible encoding sequences for peptide T E W R K/P K (SEQ ID NO:23).

The DNA fragments resulting from the above reactions are amplified for use as probes by cloning or by further PCR and radiolabeled by random or specific priming.

Approximately 800,000 plaques are plated according to manufacturer's directions. For screening, plaque filters are prehybridized at room temperature in 50% formamide, 5× SSC, 10× Denhardt's, 0.1% (w/v) SDS, 5 mM $Na_2$EDTA, 0.1 mg/ml denatured salmon sperm DNA. Hybridization with a mixture of the Garm 2 and Garm 106 probes is conducted at room temperature in the same buffer as above with added 10%(w/v) dextran sulfate and probe. Plaque purification and phagemid excision were conducted as described in Stratagene Zap cDNA Synthesis Kit instructions.

Approximately 90 acyl-ACP thioesterase clones were identified and sorted as to thioesterase type by DNA sequencing and/or PCR analysis. Of the analyzed clones, at least 28 were Class I (FatA) types, and 59 were Class II (FatB) types. Two subclasses of FatA type clones were observed, the most prominent type is termed GarmFatA1 and the single clone of the second subclass is termed GarmFatA2. DNA and translated amino acid sequence of GarmFatA1 clone C14-4 is presented in FIG. 4. DNA sequence and translated amino acid sequence (SEQ ID NO:9 and 25) of the FatA2 clone C14-3 is presented in FIG. 5.

Results of thioesterase activity assays on mangosteen Class I thioesterase clone GarmFatA1 using 16:0, 18:0 and 18:1 acyl-ACP substrates are shown below.

| Acyl-ACP Thioesterase activity (cpm/min) | | | |
| --- | --- | --- | --- |
| | 16:0 | 18:0 | 18:1 |
| Control | 1400 | 3100 | 1733 |
| GarmFatA1 | 4366 | 23916 | 87366 |

The GarmFatA1 cone demonstrates preferential activity on C18:1 acyl-ACP substrate, and also demonstrates substantial activity (approximately 25% of the 18:1 activity) on C18:0 acyl-ACP substrates. Only a small increase in C16:0 activity over activity in control cells is observed, and the 16:0 activity represents only approximately 3% of the 18:1 activity.

Expression of GarmFatA1 thioesterase in *E. coli* and assay of the resultant thioesterase activity demonstrates that C18:1 is highly preferred as the acyl-ACP substrate. The thioesterase activity on 16:0 and 18:0 acyl-ACP substrates are approximately equal and represent less than 5% of the observed 18:1 activity.

D. *Brassica campestris* (rapa)

DNA sequence and translated amino acid sequence of a *Brassica campestris* Class I acyl-ACP thioesterase are provided in WO 92/20236 (FIG. 6).

E. *Cuphea palustris* C8/C10

Total RNA is isolated from developing seeds of *C. palustris* using the modified CTAB procedure described above. A lambda ZipLox (BRL; Gaithersburg, Md.) cDNA library containing approximately $6 \times 10^6$ pfu is constructed from total RNA. Approximately 500,000 plaques from the unamplified library are screened using a mixed probe containing the thioesterase coding regions from *Cuphea hookeriana* Class II thioesterase clones CUPH-1 (CMT-9), CUPH-2 (CMT-7) and CUPH-5 (CMT-10). (DNA sequences of these clones are provided in WO 94/10288). Low stringency hybridization conditions are used as follows: hybridization is conducted at room temperature in a solution of 30% formamide and 2× SSC (1× SSC=0.15M NaCl; 0.015M Na citrate). Eighty two putative positive clones were identified, thirty of which were plaque purified. The nucleic acid sequence and translated amino acid sequence of a clone designated as MCT29 (CpFatB1 is provided in FIG. 6. The translated amino acid sequence of this clone is approximately 83% identical to the sequence of a *Cuphea hookeriana* CUPH-2 clone (CMT-7 in FIG. 7 of WO 94/10288) having primary thioesterase activity on C8:0 and C10:0 fatty acyl-ACP substrates.

Constructs for expression of MCT29 in *E. coli* are prepared. SphI and StuI sites are inserted 5' to the presumed mature protein N-terminus located at amino acid 114 by PCR. Mature N-terminus predicted by correspondence to Leu 84 originally identified as bay thioesterase mature protein N-terminus. The mature protein encoding region is cloned as a StuI/XbaI fragment into pUC118, resulting in clone MCT29LZ, to provide for expression of the *C. palustris* thioesterase in *E. coli* as a lacZ fusion protein. Lysates of transformed *E. coli* cells expressing the MCT29 thioesterase protein are assayed for acyl-ACP thioesterase activity. The results demonstrate that CpFatB1 encodes a thioesterase enzyme having activity primarily on C8- and C10-ACP substrates, with 50% higher activity on C8-ACP than on C10-ACP. Low activity on C14-ACP substrate is also observed at levels of approximately 10% of the C8-ACP activity.

MCT29LZ is also transformed into *E. coli* fadD, an *E. coli* mutant which lacks medium-chain specific acyl-CoA synthetase (Overath et al., *Eur. J. Biochem* (1969) 7:559–574) for analysis of lipid composition. Results of these analyses demonstrate a substantial increase in the production of 8:0 and 10:0 fatty acids in cells transformed with the *C. palustris* MCT29LZ clone.

The closely related *C. hookeriana* ChFatB2 clone also demonstrates preferential activity on C8:0 and C10:0 acyl-ACP substrates, with 50% higher activity on C10:0 as opposed to C8:0 substrates. Expression of the ChFatB2 clone in seeds of transgenic Brassica plants results in increased production of C8 and C10 fatty acids in the seeds, with C10 levels higher than C8 levels. (See co-pending application Ser. No. 08/261,695 filed Jun. 16, 1994.)

F. *Cuphea palustris* C14

The nucleic acid sequence and translated amino acid sequence of an additional *C. palustris* Class II thioesterase clone, MCT34 (CpFatB2), is provided in FIG. 7. The translated amino acid sequence of this clone is approximately 80% identical to the sequence of a *Cuphea hookeriana* CUPH-4 clone (CMT-13 in FIG. 8 of WO 94/10288).

Constructs for expression of MCT34 in *E. coli* are prepared. SphI and StuI sites are inserted 5' to the presumed mature protein N-terminus located at amino acid 108 by PCR. The mature protein encoding region is cloned as a StuI/XbaI fragment into pUC118, resulting in clone MCT34LZ, to provide for expression of the *C. palustris* thioesterase in *E. coli* as a lacZ fusion protein. Lysates of transformed *E. coli* cells expressing the MCT34 thioesterase protein are assayed for acyl-ACP thioesterase activity. The results demonstrate that CpFatB2 encodes a thioesterase enzyme having activity primarily on C14-ACP substrate. Activity on C16-ACP substrate is also observed at levels of approximately 30% of the C14-ACP activity.

MCT34LZ is also transformed into *E. coli* fadD, an *E. coli* mutant which lacks medium-chain specific acyl-CoA synthetase (Overath et al., *Eur. J. Biochem* (1969) 7:559–574) for analysis of lipid composition. Results of these analyses demonstrate a substantial increase in the production of 14:0 and 14:1 fatty acids in cells transformed with the *C. palustris* MCT34LZ clone.

Example 2

Chimeric Thioesterase Constructs

Both cDNA's of the bay and camphor thioesterases contain open reading frames encoding 382 amino acids. Only 31 amino acids are different, among them more than half are conservative substitutions (FIG. 8). The codon usage is highly conserved between the two genes, suggesting their the common origin.

Plasmid pCGN3823 (WO 92/20236 and Voelker et al. (1994) supra) contains a 1.2-kb XbaI fragment of a bay C12 preferring thioesterase cDNA in a pBS- (Stratagene; La Jolla, Calif.) plasmid backbone and encodes the mature bay thioesterase protein beginning at amino acid 84 (as numbered in Voelker et al. (1992) supra). Amino acid 84 of the bay thioesterase was initially identified as the amino terminus for the mature protein based on amino acid sequence analysis of the purified protein. Comparison to translated amino acid sequences of other cloned plant medium-chain acyl-ACP thioesterases, however, indicates that the amino terminus may be located further upstream of the leu 84 residue Jones et al. (1995) supra). Plasmid pCGN5220, described above, contains an XbaI/XhoI fragment of a camphor C14 preferring thioesterase cDNA inserted into pBC+ plasmid (Stratagene). The XbaI site in the camphor cDNA is present at amino acid residue 84, a leucine, as in the bay thioesterase encoding region.

Figure 9:
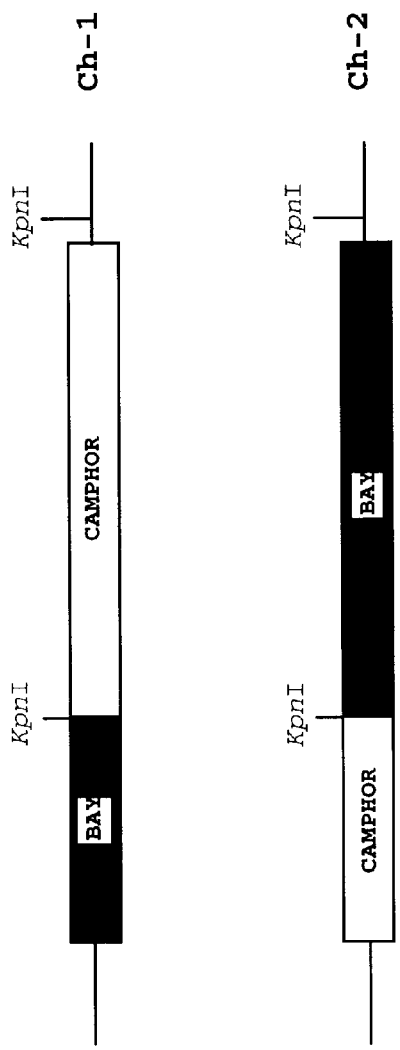
FIG. 9. Bay/camphor chimeric constructs, Ch-1 and Ch-2, are shown as in-frame fusions of N- and C-terminal portions of the thioesterases (from left to right). The KpnI site used in constructing the chimeric constructs is shown.

There is a conserved, unique Kpn I site in both the bay and camphor cDNA clones at amino acid residue 177 of the encoding sequence for the precursor bay and camphor thioesterases (FIG. 9). A second Kpn I site is located within the polylinkers of the plasmids 3' to the stop codons of the thioesterase sequences. The interchange of the two KpnI fragments between pCGN3823 and pCGN5220 allows the fusion of the N-terminal region of one thioesterase to the C-terminal region of the other, forming two chimeric enzymes.

To prepare the chimeric constructs, pCGN3823 and pCGN5220 were digested with KpnI and the resulting fragments gel-purified and ligated into the backbone plasmid from the opposite origin. DNA mini-preparations and restriction digestions were used to identify the correct fusion constructs. The chimeric constructs used for expression and enzyme assays were also confirmed by DNA sequencing.

The resulting chimeric enzymes contain 92 amino acids from the N-terminal of one thioesterase and 207 amino acids from the C-terminal portion of the other. The fusion protein containing the C-terminal portion of the camphor thioesterase is referred to as Chimeric 1 (Ch-1), and the other fusion protein is called Chimeric 2 (Ch-2) (FIG. 9).

Example 3

Flexibility and Secondary Structure Analyses

Predicted secondary structures of plant acyl-ACP thioesterases are determined by computer analysis. Secondary structure predictions are based on methods of Chou and Fasman (Chou et al. (1974) *Biochem.* 13:222–245; Prevelige et al. (1989) in *Prediction of Portein Structure and the Principles of Protein Conformation* (Fasman, G. D. ed.), pp 391–416, Plenum, New York); and Garnier et al. (1978) J. Mol. Biol. 120:97–120).

Flexibility of various regions of plant acyl-ACP thioesterase regions are predicted by computer analysis using MacVector (International Biotechnologies, Inc.), based on flexibility prediction methods of Karplus and Schulz (*Naturwiss.* (1985) 72:212–213).

Example 4

Engineering FatB Thioesterases

A. Bay C12 Thioesterase

PCR site-directed mutagenesis (Higuchi et al. (1988) *Nucl. Acids Res.* 16:7351–7367) is used for amino acid replacements. The sense mutant primers used for the mutagenesis are as follows:

| | | |
|---|---|---|
| M197R/R199H | 5'-GGAAATAATGGCCGACGACATGATTTCCTTGTCC | (SEQ ID NO: 16) |
| T231K | 5'-GGTTGTCCAAAATCCC | (SEQ ID NO: 17) |
| R327Q | 5'-GCGTGCTGCAGTCCCTGACC | (SEQ ID NO: 18) |
| R322M/R327Q | 5'-GAGAGAGTGCACGATGGATAGCGTGCTGCAGTCCCTGACC | (SEQ ID NO: 19) | where bold letters M, R, H, T, K and Q are one-letter abbreviations for amino acids methionine, arginine, histidine, threonine, lysine and glutamine respectively, and the mutated nucleotides are underlined.

PCR conditions were as follows: five cycles of the PCR were programmed with denaturation for 1 min at 94° C., renaturation for 30 seconds at 48° C., and elongation for 2 min at 72° C. These first five cycles were followed by 30 cycles with renaturation for 30 seconds at 60° C. The amplified DNA was recovered by ethanol precipitation, and examined by gel electrophoresis. The DNA was then digested with XbaI and BamHI, ethanol precipitated and ligated into XbaI/BamHI cut pBC plasmid. The ligation mixture was used to transform Sure cells (Stratagene) by electroporation, and the transformed cells were plated on LB medium containing 50 mg/l of chloramphenicol. Constructs containing the correct inserts were identified by mini-DNA preparation and restriction digestion. The inserted DNA was sequenced to confirm the mutations.

The same designations noted above for the PCR primers were used for the mutant clones. As an example, M197R/R199H refers to a clone in which the methionine at residue 197 (of precursor bay thioesterase) was changed to an arginine, and where the arginine at residue 199 was changed to a histidine. Similarly, T231K indicates a mutant in which the threonine at residue 231 was changed to a lysine.

B. *Cuphea palustris* C14 Thioesterase

Figure 10:
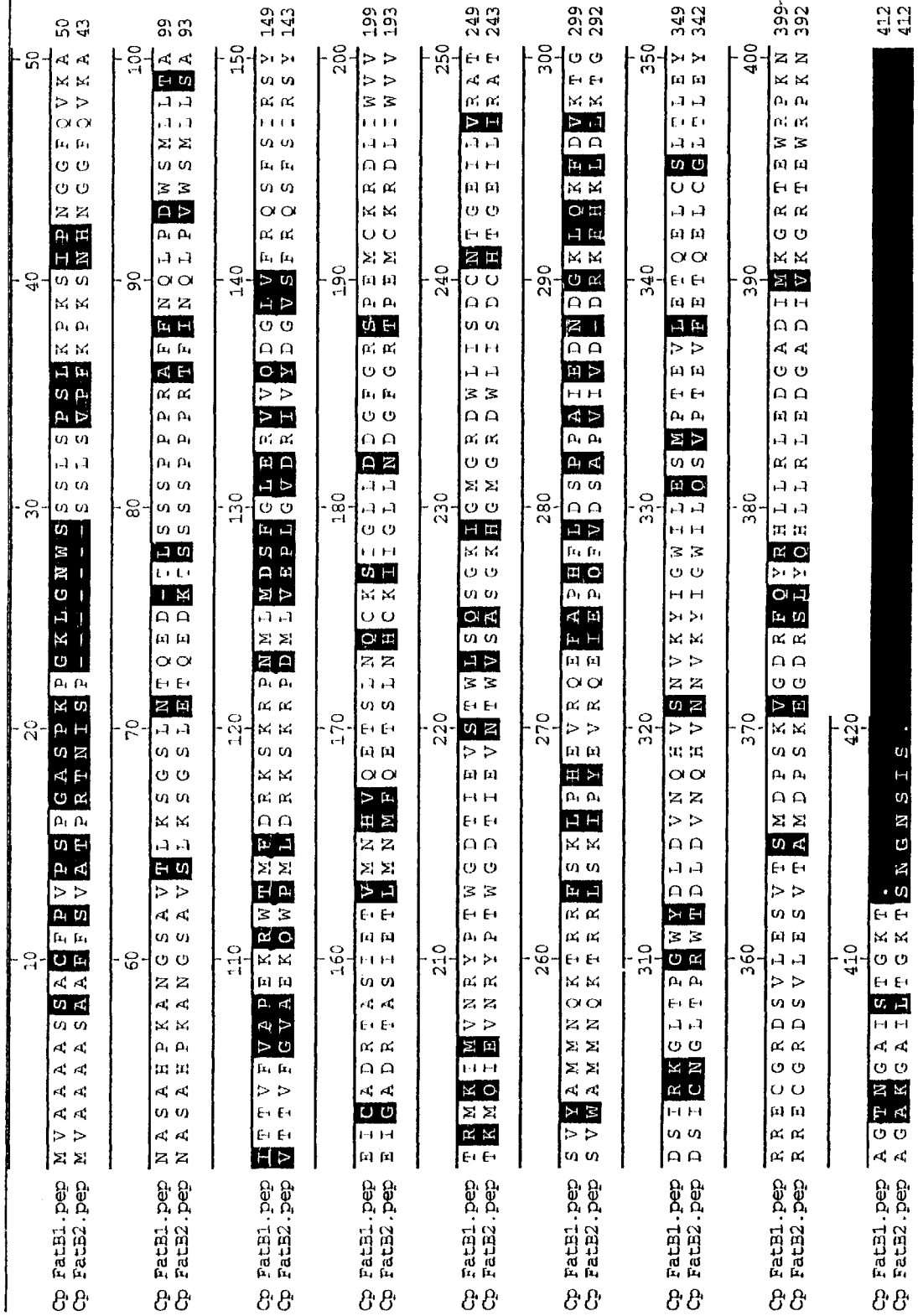
FIG. 10. An amino acid sequence comparison of *C. palustris* CpFatB1 (C8/C10) and *C. palustris* CpFatB2 (C14) acyl-ACP thioesterases is provided. Amino acid residues which differ between the thioesterases are indicated by bold shading.

To determine possible amino acid modifications for alteration of thioesterase substrate specificity towards shorter chain length fatty acyl-ACPs, sequences for C14:0 preferring thioesterases may be compared to sequences for C8:0 and C10:0 preferring thioesterases. A comparison of amino acid sequences of thioesterase CpFatB2 (C14) to CpFatB1 (C8/C10) is shown in FIG. 10. The most striking differences in these thioesterase sequences is found in amino acids 230 to 312. Substitutions, such as H229I, H241N, W253Y, E275A, R290G, F292L, L295F, and C304R, can be made in single- and combinatory-form. Alternatively, domain swapping clones may be prepared which provided for switching of portions of the C8/10 and C14 sequences. Of particular interest in this regard are sequences IEPQFV starting at amino acid 274, and DRKFHKL starting at amino acid 289.

Example 5

Specificity of Chimeric Enzymes and Bay Mutants

Transformed *E. coli* cells in lacZ expression constructs are grown to 0.6 O.D.$_{600}$ at 30° C., followed by addition of 1 mM IPTG (isopropylthiogalactopyranoside) and continuous growth at 30° C. for 2 hours. The sedimented cells were resuspended in the assay buffer, and acyl-ACP hydrolysis is measured as previously described (Davies, H. M. (1993) *Phytochemistzy* 33, 1353–1356). Sure cells transformed with pCGN3823 and pBC served as positive and negative controls, respectively.

FIG. 11 shows the thioesterase specific activities of the chimeric bay/camphor enzymes when *E.coli* cells transformed with Ch-1 and Ch-2 were induced and assayed. For Ch-1 (FIG. 11A) the preferred substrate is 14:0-ACP, whereas for Ch-2 (FIG. 11B) it is 12:0-ACP. These results indicate that the C-terminal portion of the thioesterase protein determines the substrate specificity.

The enzyme specificities of two of the bay mutants are shown in FIGS. 11C and 11D. A mutant in which Met197 becomes an arginine and Arg199 becomes a histidine (M197R/R199H) results in altered specificity of the bay thioesterase such that the enzyme is equally specific towards both 12:0-ACP and 14:0-ACP substrates (FIG. 11C). Another mutant, T231K, gives an identical activity profile as the wild type (data not shown). However, the triple mutant M197R/R199H/T231K, which combines the three mutations, demonstrates 14:0-ACP specific thioesterase activity (FIG. 11D). When this triple mutant enzyme is assayed at high concentration, very low levels of 12:0-ACP activity are detectable.

Two more mutants (R327Q and R322M/R327Q) were also tested for thioesterase activity. Both mutants show identical activity profiles, and their specific activities toward 12:0-ACP and 14:0-ACP decrease about 100- and 30-fold, respectively, compared to the wild type bay thioesterase. These data indicate that the mutation R327Q is responsible for the decreased activity. Decreased activity of R327Q is likely due to the fact that this amino acid position is located very close to the active site cysteine, C320. Studies which demonstrated the catalytic activity of C320 were conducted as follows. C320 was changed by site-directed mutagenesis to either serine or alanine. The mutant C320A completely lost thioesterase activity, while C320S retained approximately 80% of the wild-type activity. Interchange of cysteine and serine in the active site has also been demonstrated for animal thioesterases (Witkowski et al. (1992) *J. Biol. Chem.* 267:18488–18492). In animals, the active site is a serine, and the change thus was from serine to cysteine.

Example 6

Expression of Bay Mutants in *E. coli* fadD Cells

The *E. coli* fatty acid-degradation mutant strain K27 (fadD88), a strain lacking acyl-coenzyme A synthetase, is unable to utilize free fatty acids when they are supplied in the medium (Klein et al. (1971) *Eur. J. Biochem.* 19:442–450). Thus, it is an ideal host for observing the impact of recombinant thioesterases on the bacterial fatty acid synthase without interference from fatty acid degradation. *E. coli* fadD was obtained from the *E. coli* Genetic Stock Center, Yale University (CGSC 5478). The fadD cells were transformed with either the pBC or the mutant constructs, and grown overnight at 30° C. in LB medium containing 50 mg/l chloramphenicol and 1 mM IPTG. Total lipids were analyzed as described previously (Voelker et al. (1994) supra). Results of these analyses are presented in Table I below.

TABLE I

| Strain | Free Fatty Acid Accumulation (nmole/ml culture) | |
| --- | --- | --- |
| | 12:0 | 14:0 |
| Control* | 0.3 | 1.6 |
| Bay Thioesterase | 505.5 | 39.0 |
| M197R/R199H | 123.5 | 181.1 |
| M197R/R199H/T231K | 35.4 | 352.9 |

*fadD cells transformed with the pBC vector only.

When bay thioesterase is expressed in fadD cells, large amounts of laurate (more than 500-fold above control background) and small amounts of myristate (about 10% of that of laurate) are produced (Table I). This result is consistent with the previous report (Voelker et al. (1994) supra). When mutant M197R/R199H is expressed in fadD cells, the ratio of 12:0 to 14:0 accumulation changes to 1:1.5 (Table I), reflecting the thioesterase specificity of this mutant (FIG. 11C). When mutant M197R/R199H/T231K is expressed in fadD cells, the ratio of 12:0 to 14:0 is completely reversed from that seen with the wild-type bay thioesterase. This result is also consistent with enzyme specificity of the mutant (FIG. 11D).

Example 7

Kinetic Analysis

In order to gain insight into the impact of the mutations to the bay thioesterase, basic kinetics and inhibition studies were performed. Progress curves of thioesterase activity were obtained by scaling up the assay volume and sampling 100 $\mu$l at 5 minute intervals into 0.5 ml stop solution. Kinetic assays were performed at 30° C. in buffer containing 100 mM Tris-HCl, pH 8.0, 0.01% Triton X-100, 1 mM DTT, 10% glycerol. After extraction of each reaction mixture with 2.0 ml dimethyl ether, the radioactivity in 900 $\mu$l of the organic fraction was determined by liquid scintillation counting. This procedure allows accurate measurement of the total extractable free fatty acid ($^{14}$C-labeled) without the interference of interphase between the organic and aqueous fractions. Production of laurate and myristate in this assay was linear with respect to time for at least 30 min, and with respect to enzyme concentrations up to 1 mU. All assays were done in duplicate. Initial rate data were fitted to the following equations using kinetics software from Bio-Metallics, Inc. (K CAT): for competitive inhibition $v=V_{max}S/[K_{m,app}(1+I/K_{is})+S]$; for noncompetitive inhibition $v=V_{max}S/[K_{m,app}(1+I/K_{is})+S(1+I/K_{ii})]$; and for uncompetitive inhibition $v=V_{max}S/[K_{m,app}+S(1+I/K_{ii})]$; where v is velocity; $V_{max}$ is maximum velocity; S is substrate concentration; $K_{m,app}$ is apparent Michaelis constant; $K_{is}$ and $K_{ii}$ are slope and intercept inhibition constants, respectively; I is inhibitor concentration. Results of these analyses are presented in Table II below.

TABLE II

Kinetic Constants of Wild-type Bay TE and Triple Mutant M197R/R199H/T231K

| Enzyme | $K_{m,app}$ (μM) | | $K_i$ (μM)* |
|---|---|---|---|
| | 14:0-ACP | 12:0-ACP | 12:0-ACP |
| Bay TE | 6.4 ± 1.9 | 1.9 ± 0.5 | 10.2 ± 1.2 (competitive)** |
| Mutant | 2.3 ± 0.4 | ND | 11.6 ± 0.2 (competitive) |

*slope inhibition constants of 12:0-ACP with 14:0-ACP as varied substrates
**competitive inhibition with respect to 14:0-ACP.
ND — not determined.

Under the same experimental conditions, both bay thioesterase and the triple mutant M197R/R199H/T231K have similar values of $K_{m,app}$ with respect to 14:0-ACP. The specific activity of the mutant towards 12:0-ACP is too low to obtain any meaningful kinetic parameters under our assaying system. Nevertheless, these results indicate that the mutations do not significantly increase the substrate (14:0-ACP) binding affinity to the mutant enzyme.

Inhibition assays were conducted under the conditions described above using cold 12:0-ACP to compete with the substrate ($^{14}$C labeled 14:0-ACP). Results of these assays are presented in Table III below.

TABLE III

Inhibition of 14:0-ACP Thioesterase Activity by 12:0-ACP

| Enzyme | Substrate (14:0-ACP) Concentration (μM) | Inhibitor (12:0-ACP) Concentration (μM) | Inhibition (%) |
|---|---|---|---|
| Bay TE | 5 | 5 | 53 |
| | 5 | 25 | 78 |
| Mutant | 5 | 5 | 48 |
| | 5 | 25 | 76 |

In these inhibition assays, a very similar result is seen with the wild-type and the mutant enzymes. When equal amounts of inhibitor (12:0-ACP) and substrate (14:0-ACP) are present in the assay, the 14:0-ACP TE activity is reduced approximately 50%. If the amount of 12:0-ACP is 5 times that of 14:0-ACP, the 14:0-ACP TE activity is reduced more than 75%. Consistent with what has been observed before (Pollard et al., supra), a similar kinetic mechanism is used by the wild-type bay TE, i.e. both 12:0- and 14:0-ACP have similar $K_m$'s, but $V_{max}$ is highly favorable for 12:0-ACP. These data suggest that the specificity of the mutant enzyme is determined in the acyl hydrolysis step, that is both 12:0- and 14:0-ACP can bind to the mutant enzyme with similar affinity, however 14:0-ACP is cleaved at a much higher rate. This conclusion is further supported by inhibition kinetics, which show that 12:0-ACP is a competitive inhibitor with respect to 14:0-ACP ($K_i$ values are 10.2+1.2 μM and 11.6+ 0.2 μM for the wild-type and mutant enzymes, respectively (Table II).

Thus, the amino acid substitutions described for the bay thioesterase apparently do not directly impact the substrate binding site, as 12:0-ACP is a good competitive inhibitor to 14:0-ACP in both the wild type and the mutant enzymes. In fact, the Michaelis constants are similar and independent of substrate length for bay thioesterase and the engineered bay enzyme, suggesting that specificity must be largely determined in the acyl hydrolytic step. Because the substrates (acyl-ACP) are relatively large molecules ($M_r$ of ACP is about 9 Kd), it is likely that plant thioesterases have very relaxed binding pockets. However, the enzymes have high selectivities with respect to fatty acid chain length or structure (i.e. the presence or absence of double bonds).

Furthermore, the tripeptide Met-Arg-Arg of native bay thioesterase is not the sole the determining factor for selectivity towards 12:0-ACP, as this tripeptide is commonly found at the same location in other medium chain specific thioesterases. Therefore, the changes in the engineered bay thioesterases may only slightly alter certain secondary structures, similar to what was observed when surface loops of *Bacillus stearothermophilus* lactate dehydrogenease were modified (El Hawrani et al. (1994) *Trends in Biotech.* 12:207–211). Changing the tripeptide from M-R-R to R-R-H apparently reduced the flexibility of the β-structure immediately following this tri-peptide, according to the predictions of chain flexibility in proteins (Karplus et al. (1985) *Naturwiss.* 77, 212–213). This may lead to reduction of the flexibility of the substrate binding pocket and active site.

Example 8

Engineering FatA Thioesterases

Alteration of thioesterase enzyme specificity of a mangosteen Garm FatA1 clone is provided as an example of modification of FatA or Class I type thioesterases. Desirable modifications with respect to FatA thioesterases include alteration in the substrate specificity such that activity on C18:0 fatty acyl-ACP is increased relative to activity on C18:1 or C16:0 fatty acyl-ACP substrates.

For example, in order to increase the relative activity on saturated fatty acids, such as C18:0, mutations in regions of Class I thioesterases which differ from the corresponding regions in Class II thioesterases, which act primarily on saturated fatty acids, may be useful. The data from bay thioesterase engineering experiments indicate that the region from amino acids 229 to 285 (as numbered in the top line consensus sequence on FIG. 1) is important in thioesterase substrate binding. Amino acid sequence comparison of this region indicates that in the highly conserved region from amino acids 250–265, several charged amino acids are different in FatA as compared to FatB thioesterases. In FatA thioesterases, amino acid 261 is negatively charged with a few exceptions, whereas in FatB clones analyzed to date, amino acid 261 is in most cases positively charged. Also, in FatA thioesterases, amino acid 254 is positively charged in all FatA thioesterases studied to date, whereas in FatB clones analyzed to date, amino acid 254 is in all cases an amino acid having no charge. Thus, alteration of the amino acid charge at these positions may lead to alteration of substrate preference.

Figure 12:
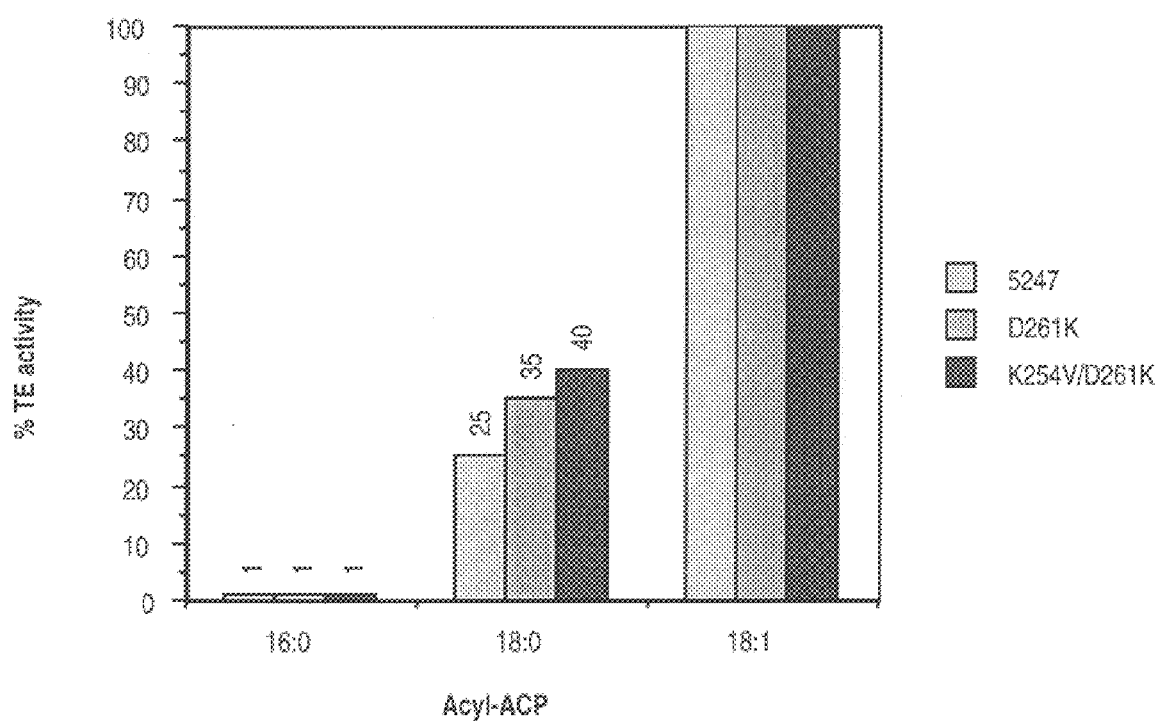
FIG. 12. Relative thioesterase activity of wild-type (5247) and mutant *Garcinia mangifera* thioesterases (GarmFatA1) on 18:1, 18:0 and 16:0 acyl-ACP substrates are provided.

A FatA TE mutant in amino acid 261 (FIG. 1 concensus numbering), D261K of mangosteen FatA1, is generated using PCR site-directed mutagenesis similar to the methods described for modification of bay thioesterase sequences. Mutant D261K is measured for thioesterase activity as described above (Davies, H. M. (1993) supra). Results of these analyses (FIG. 12) demonstrate that the preference for 18:0 versus 18:1 was 35% (18:0/18:1) in mutant D261K, as compared to 25% in the wild-type Garm FatA1. Both the wild-type and mutant Garm FatA1 clone demonstrate very low activity on 16:0 and no activity on medium-chain length substrates such as C10:0 through C14:0. This result once again supports the bay evidence which indicates that modification of this region can change the enzyme activity and specificity.

Figure 13:
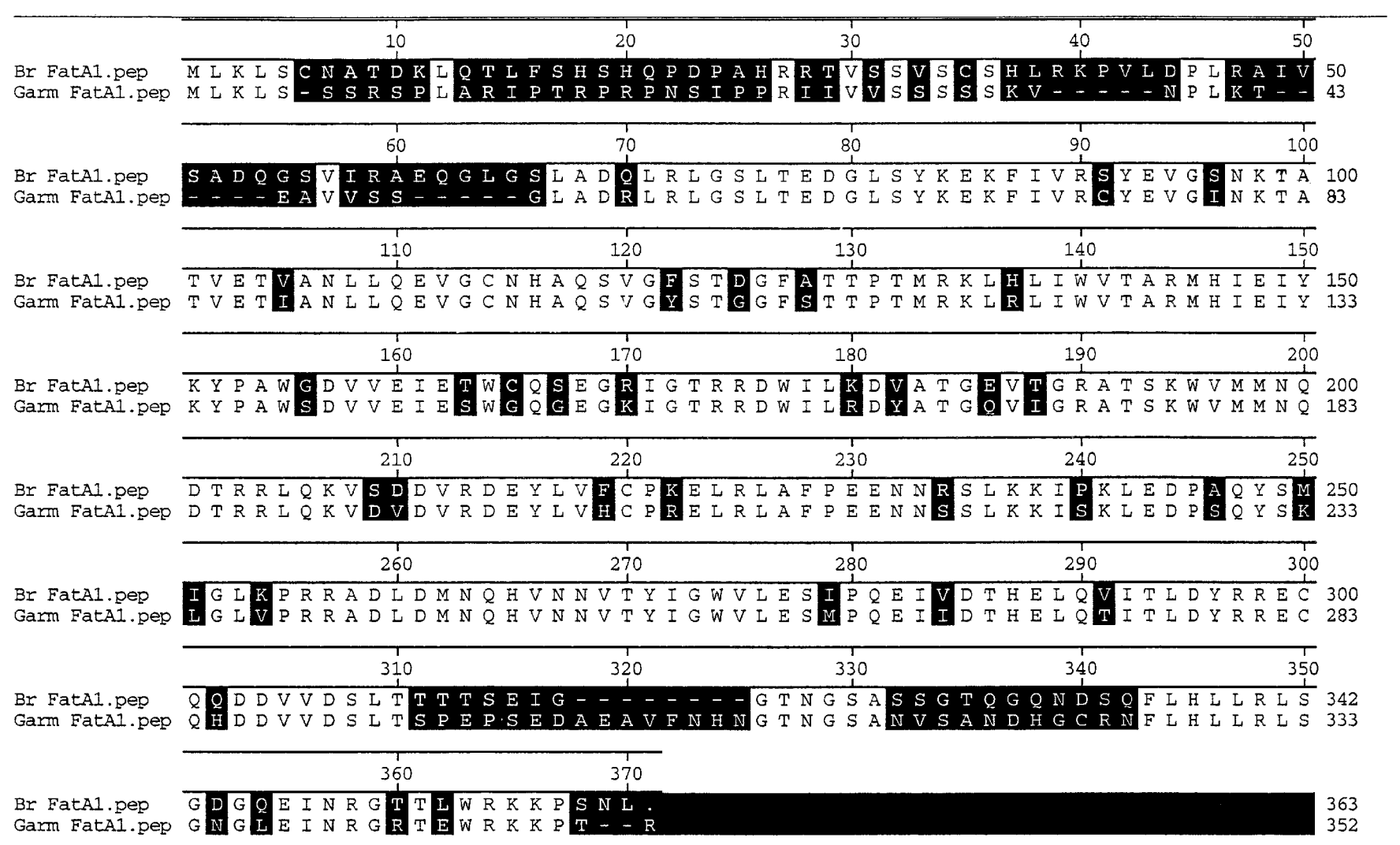

Further desirable amino acid modifications of mangosteen Garm FatA1 clones may be selected by comparison of the 18:0 enriched Garm FatA1 thioesterase amino acid sequence to the amino acid sequence for a FatA clone having activity primarily on 18:1 substrates, with little or no activity on 18:0 substrates. A comparison of the amino acid sequences of Garm FatA1 and an 18:1 preferring thioesterase clone from *Brassica campestris* (rapa), Br FatA1, is provided in FIG. 13. In view of the binding substrate alterations demonstrated for the bay thioesterase in the region following the predicted β-sheet and turn (anchored by amino acids G169 and G172 of the FIG. 13 mangosteen and Brassica thioesterase comparison), this region is also a target for substrate specificity alteration of mangosteen thioesterase clone Garm-FatA1. Secondary structure analysis and amino acid sequence comparison of the mangosteen and *Brassica rapa* Class I thioesterases result in identification of several target mutations for further altering the substrate specificity of the mangosteen thioesterase, GarmFatAl. Target amino acids include Y182V, Q186E, D209S, V210D and H219F.

The above results demonstrate the ability to modify plant acyl-ACP thioesterase sequences such that engineered thioesterases having altered substrate specificity may be produced. Such thioesterases may be expressed in host cells to provide a supply of the engineered thioesterase and to modify the existing pathway of fatty acid synthesis such that novel compositions of fatty acids are obtained. In particular, the engineered thioesterases may be expressed in the seeds of oilseed plants to provide a natural source of desirable TAG molecules.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A method for obtaining an engineered plant acyl-ACP thioesterase having an altered substrate specificity with respect to the acyl-ACP substrates hydrolyzed by said thioesterase, wherein said method comprises:

(a) modifying a gene sequence encoding a first plant thioesterase protein to produce one or more modified thioesterase gene sequences, wherein said modified sequences encode engineered acyl-ACP thioesterases having substitutions, insertions or deletions of one or more amino acid residues in the region corresponding to amino acids 230 to 285 of the consensus numbering of thioesterase amino acid sequences shown in FIG. 1, wherein said region corresponds to residues 194 to 244 of SEQ ID NO: 1, residues 194 to 244 of SEQ ID NO: 2 residues 227 to 277 of SEQ ID NO: 3 residues 221 to 271 of SEQ TD NO: 4 residues 153 to 207 of SEQ ID NO: 5 and residues 170 to 224 of SEQ ID NO: 6, (b) expressing said modified gene sequences in a host cell, whereby said engineered plant thioesterases are produced and, (c) assaying said engineered plant thioesterases to detect altered substrate specificity.

2. A method according to claim 1 wherein one or more amino acid residues of said first plant thioesterase are substituted with the corresponding amino acids of a second plant thioesterase, wherein the preferential acyl-ACP substrates for said first and second plant thioesterases are different with respect to carbon chain length and/or degree of saturation.

3. A method according to claim 2 wherein said second plant thioesterase demonstrates at least 75% amino acid sequence identity with said first plant thioesterase.

4. A method according to claim 2 wherein said one or more amino acids are selected on the basis of differences in charge between the corresponding amino acids in said first and second plant thioesterases.

5. A method according to claim 1 wherein said first plant thioesterase has preferential activity on C12 acyl-ACP substrates, and wherein the activity of said engineered plant thioesterase on C14 acyl-ACP substrates is higher than the activity of said wild-type thioestrase on C14 acyl-ACP substrates.

6. A method according to claim 1 wherein said first plant thioesterase is a C12 preferring acyl-ACP thioesterase, and wherein said engineered plant thioesterase has approximately equal activity on C12 and C14 acyl-ACP substrates.

7. A method according to claim 1 wherein said first plant thioesterase is a C12 preferring acyl-ACP thioesterase, and wherein said engineered plant thioesterase is a C14 preferring acyl-ACP thioestrase.

8. A method according to claim 2 wherein said first thioesterase is modified by substitution of a peptide domain from said second thioesterase.

9. A method according to claim 1 wherein said first plant thioesterase is a Class I thioesterase.

10. A method according to claim 1 wherein said first plant thioesterase is a Class II thioesterase.

11. A method according to claim 2 wherein said first and second plant thioesterases are Class I thioesterases.

12. A method according to claim 2 wherein said first and second plant thioesterases are Class II thioesterases.

13. A method according to claim 1 wherein said first plant thioesterase has preferential activity on C18:1 acyl-ACP substrates, and wherein the activity of said engineered plant thioesterase on C18:0 acyl-ACP substrates is higher than the activity of said wild-type thioesterase C18:0 acyl-ACP substrates.

14. A DNA sequence encoding an engineered plant acyl-ACP thioesterase, wherein said engineered thioesterase demonstrates an altered substrate specificity with respect to the acyl-ACP substrates hydrolyzed by said thioesterase as compared to the wild-type plant acyl-ACP thioesterase, and wherein said engineered thioesterase has been engineered through substitutions, insertions or deletions of one or more amino acid residues in the region corresponding to amino acids 230 to 285 or the consensus of thioesterase amino acid sequences shown in FIG. 1, wherein said region corresponds to residues 194 to 244 of SEQ ID NO: 1, residues 194 to 244 of SEQ ID NO: 2, residues 227 to 277 of SEQ ID NO: 3, residues 221 to 271 of SEQ ID NO: 4, residues 153 to 207 of SEQ ID NO: 5, and residues 170 to 224 of SEQ ID NO: 6.

15. A DNA sequence of claim 14, wherein said wild-type thioesterase is a Class II thioesterase.

16. A DNA sequence thioesterase of claim 14, wherein said wild-type thioesterase is a Class I thioesterase.

17. A DNA sequence of claim 14 wherein said wild-type thioesterase is a California bay C12 preferring thioesterase, and wherein said engineered thioesterase has approximately equal activity on C12 and C14 acyl-ACP substrates.

18. A DNA sequence of claim 14 wherein said wild-type thioesterase is a California bay C12 preferring thioesterase, and wherein said engineered thioesterase is a C14 preferring thioesterase.

19. A DNA sequence of claim 14 wherein said wild-type thioesterase is a mangosteen C18:1 thioesterase, and wherein the activity of said engineered thioesterase on C18:0 acyl-ACP substrates is higher than the activity of said wild-type thioesterase on C18:0 acyl-ACP substates.

20. A recombinant DNA construct comprising a DNA sequence encoding a mangosteen Class I acyl-ACP thioesterase, wherein said acyl-ACP thioesterase has activity on C18:1 and C18:0 acyl-ACP substrates, and little or no activity on C16:0 acyl-ACP substrates.

21. A recombinant DNA construct according to claim 20 wherein said DNA sequence encodes the mangosteen Garm-FatA1 thioesterase represented by the translated amino acid sequence shown in SEQ ID NO: 5.

22. A recombinant DNA construct comprising a DNA sequence encoding a *Cuphea palustris* Class II acyl-ACP thioesterase having activity on C8:0 and C10;0 acyl-ACP substrates, wherein said activity on C8:0 acyl-ACP substrates is greater than said activity on C10:0 acyl-ACP substrates.

23. A recombinant DNA construct according to claim 22 wherein said DNA sequence encodes the *C. palustris* CpFatB1 thioesterase represented by the translated amino acid sequence shown in SEQ ID NO: 3.

24. A DNA sequence of claim 19 wherein said activity of said engineered thioesterase on C18:0 acyl-ACP substrates is at least about 10% higher than the activity of said wild-type thioesterase on C18:0 acyl-ACP substrates.

* * * * *